United States Patent
Patel et al.

(10) Patent No.: US 7,725,026 B2
(45) Date of Patent: May 25, 2010

(54) PHASE RESPONSIVE OPTICAL FIBER SENSOR

(75) Inventors: Jayantilal S. Patel, Newtown, PA (US); Zhizhong Zhuang, Bensalem, PA (US); Yuri Zadorozhny, Morrisville, PA (US)

(73) Assignee: Optellios, Inc., Langhorne, PA (US)

( * ) Notice: Subject to any disclaimer, the term of this patent is extended or adjusted under 35 U.S.C. 154(b) by 695 days.

(21) Appl. No.: 11/570,481

(22) PCT Filed: Apr. 1, 2005

(86) PCT No.: PCT/US2005/011045

§ 371 (c)(1),
(2), (4) Date: Dec. 12, 2006

(87) PCT Pub. No.: WO2006/001868

PCT Pub. Date: Jan. 5, 2006

(65) Prior Publication Data

US 2007/0253662 A1    Nov. 1, 2007

Related U.S. Application Data

(63) Continuation-in-part of application No. 10/911,326, filed on Aug. 4, 2004, now Pat. No. 7,139,476.

(60) Provisional application No. 60/580,005, filed on Jun. 15, 2004, provisional application No. 60/587,484, filed on Jul. 13, 2004, provisional application No. 60/599,006, filed on Aug. 5, 2004, provisional application No. 60/650,836, filed on Feb. 7, 2005.

(51) Int. Cl.
*H04B 10/08* (2006.01)

(52) U.S. Cl. .............. 398/16; 398/32; 398/33

(58) Field of Classification Search ............ 398/9, 398/12–13, 16, 19, 32–33, 196–197
See application file for complete search history.

(56) References Cited

U.S. PATENT DOCUMENTS

| | | | |
|---|---|---|---|
| 4,885,462 A | 12/1989 | Dakin | |
| 5,206,923 A | 4/1993 | Karlsson | |
| 5,475,298 A * | 12/1995 | Rogers | 324/96 |
| 5,694,114 A * | 12/1997 | Udd | 340/506 |
| 5,886,802 A | 3/1999 | Majima | |
| 6,211,962 B1 * | 4/2001 | Nolan | 356/450 |
| 6,493,140 B1 * | 12/2002 | Li et al. | 359/495 |
| 6,600,586 B1 * | 7/2003 | Hall | 398/207 |

FOREIGN PATENT DOCUMENTS

| GB | 02204204 A | 11/1998 |
|---|---|---|
| JP | 10160635 A | 6/1998 |

* cited by examiner

*Primary Examiner*—Dzung D Tran
(74) *Attorney, Agent, or Firm*—Duane Morris LLP

(57) ABSTRACT

The location of a physical disturbance along an optical waveguide is determined by measuring different propagation times for the resulting phase variation to propagate to phase responsive receivers at ends of bidirectional signal paths. Each receiver can have a coupler that functions as a beam combiner and as a beam splitter inserting the opposite signal. On each receiving end, the coupler provides one or more detectors with signals from which phase related independent variable values are taken, processed and mapped to phase angles. Relative phase angle versus time is derived for each opposite signal pair and correlated at a time difference, i.e., a difference in propagation time from which the location of the disturbance is resolved. Polarization sensitive and polarization insensitive examples are discussed with various optical fiber arrangements.

60 Claims, 39 Drawing Sheets

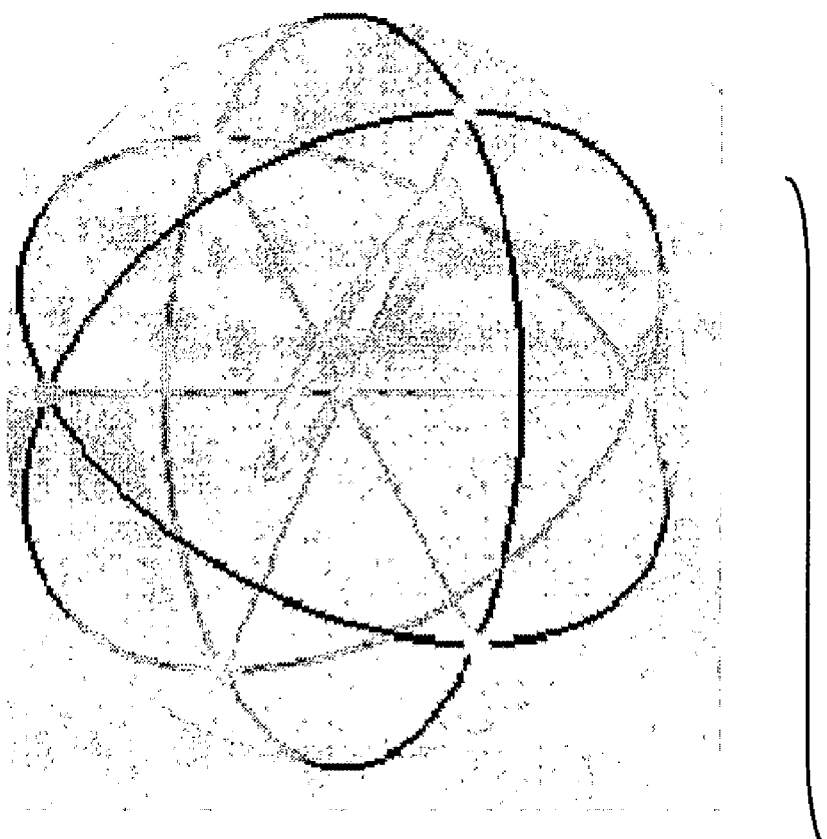
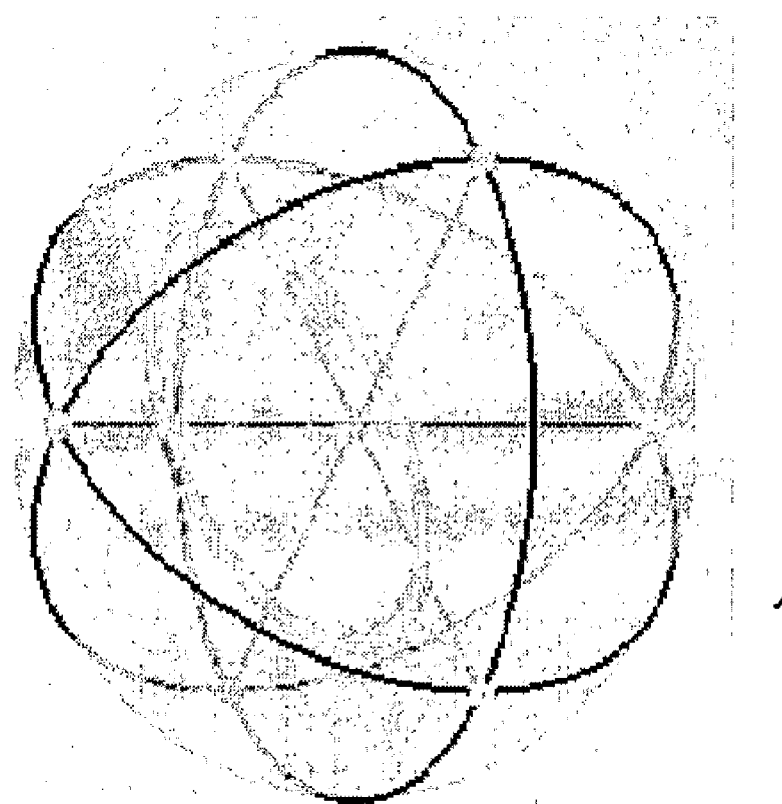
FIG 6

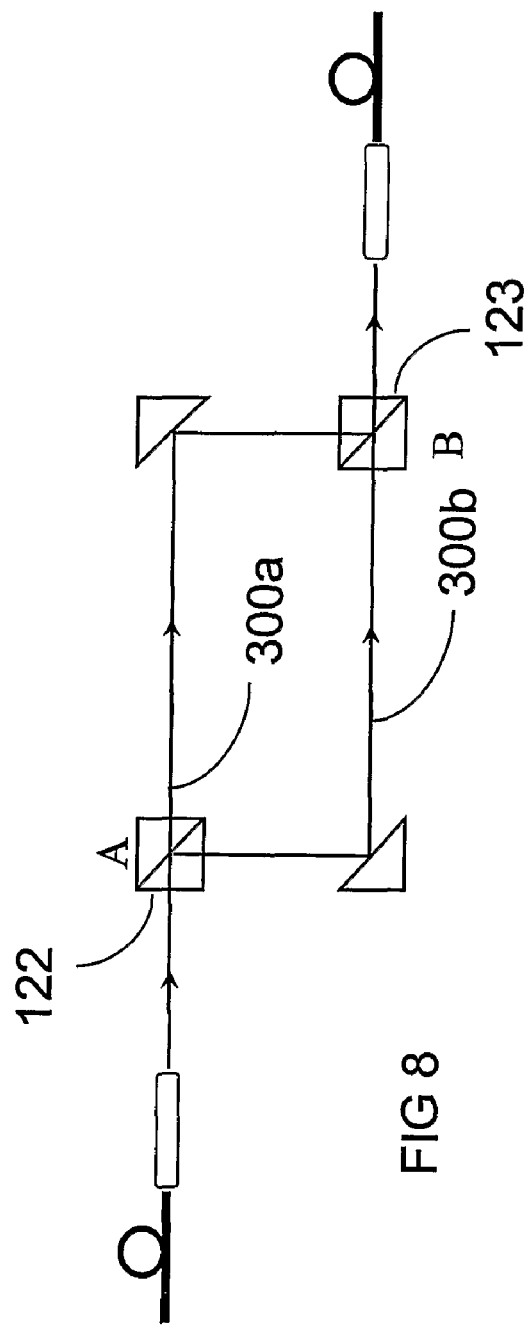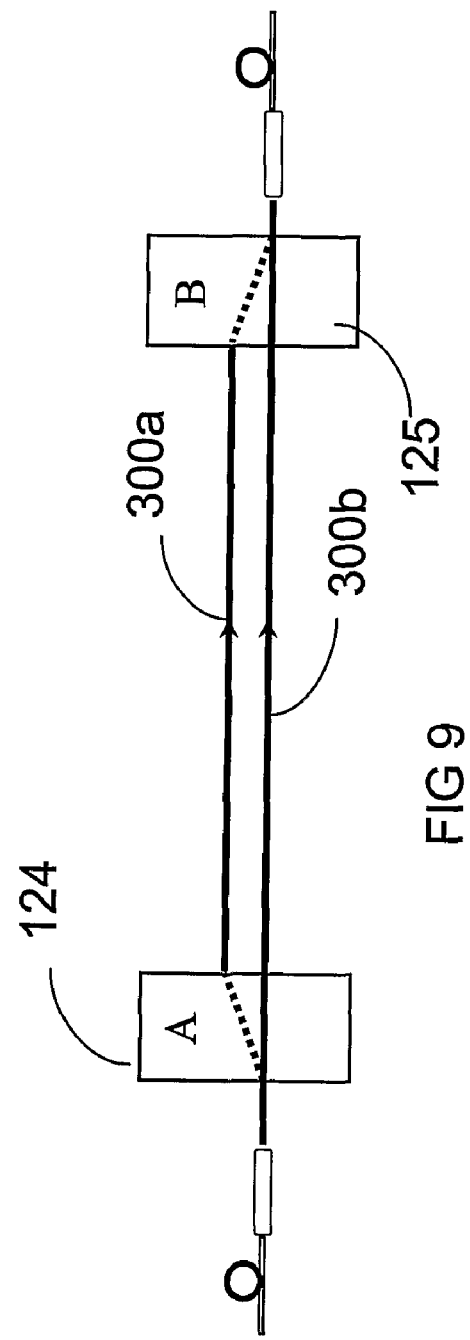
FIG 8
FIG 9

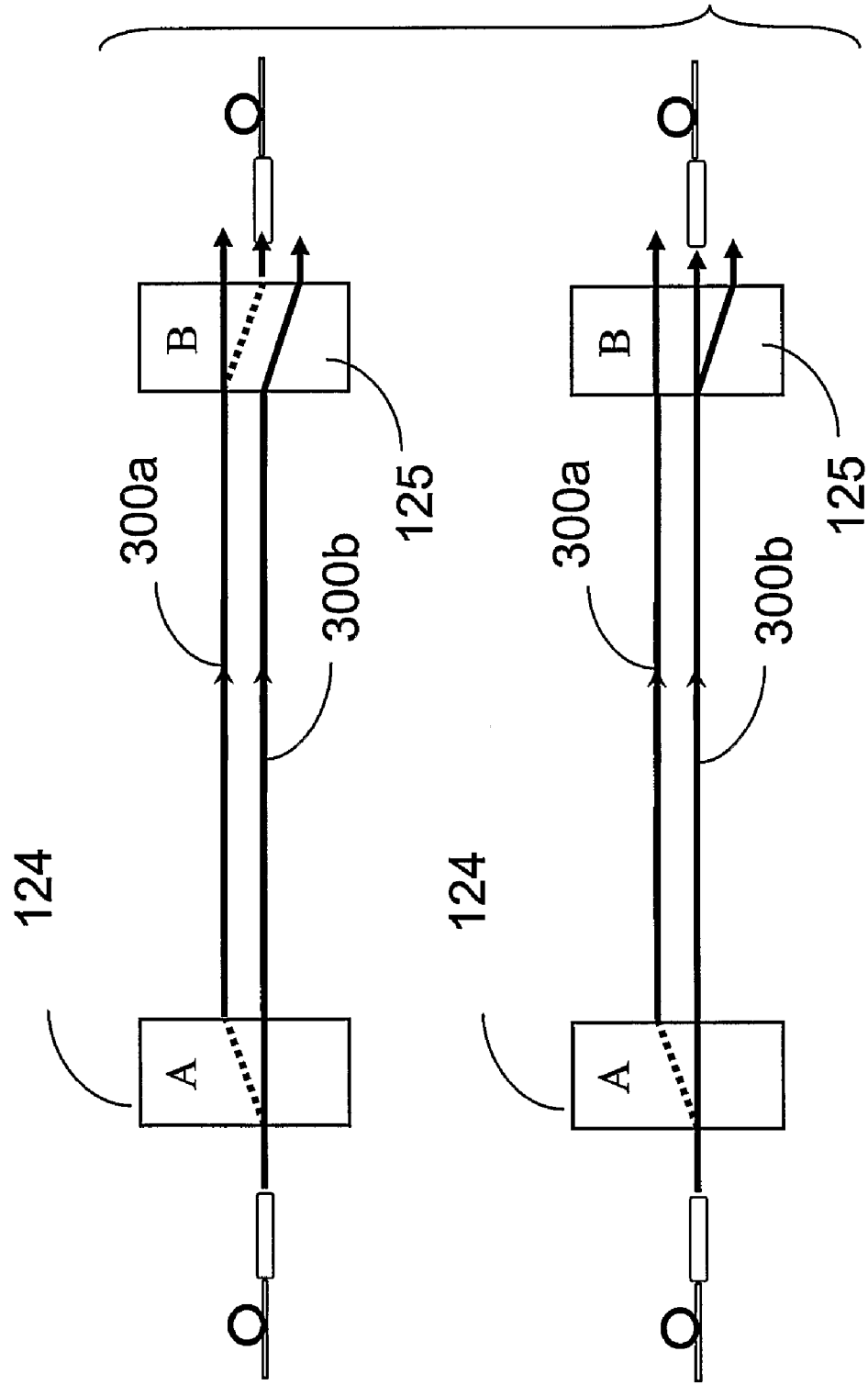

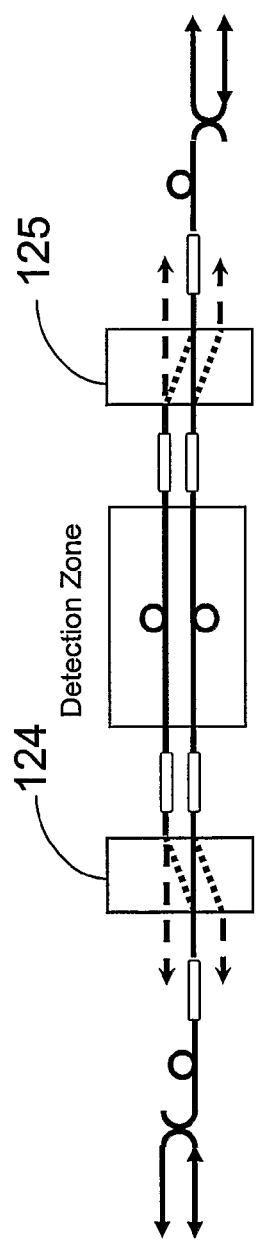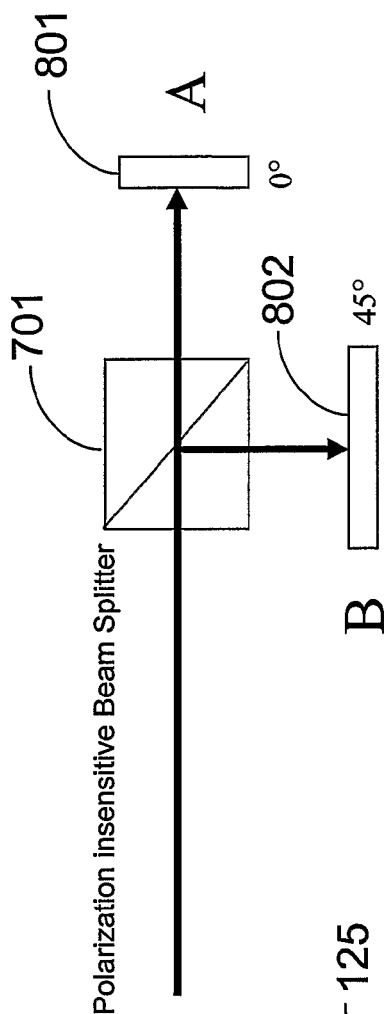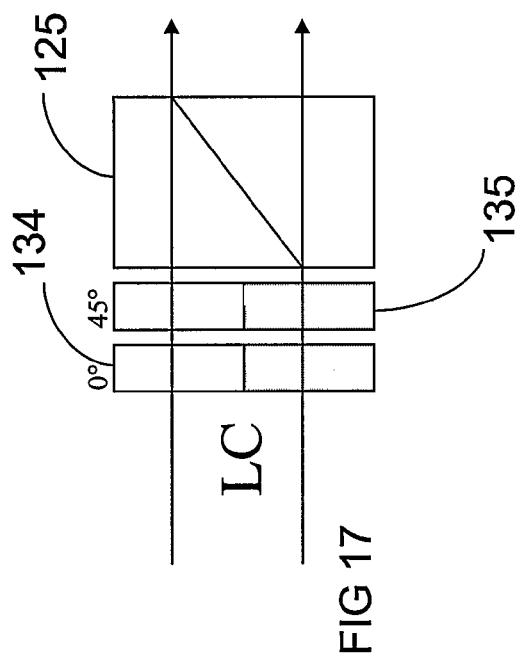

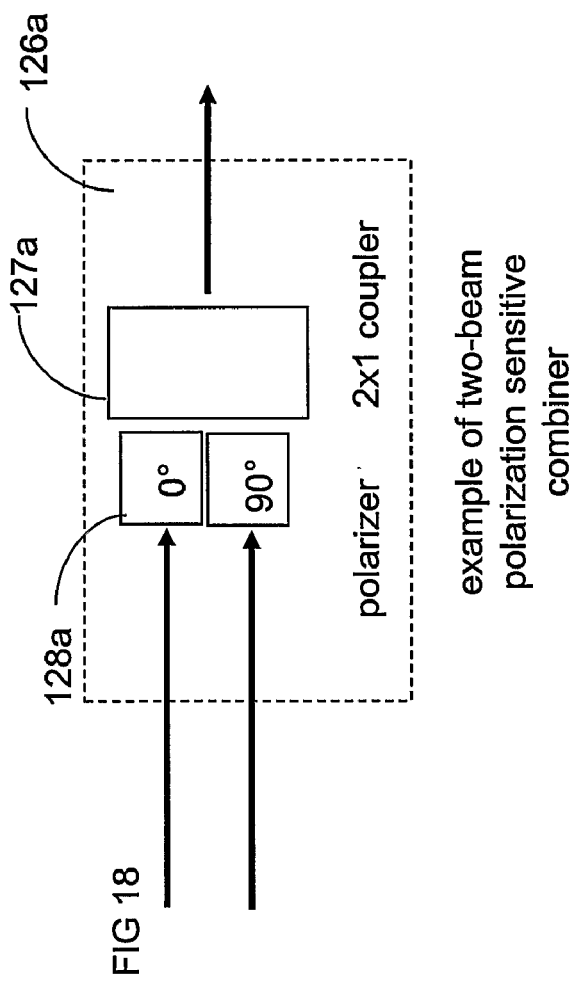
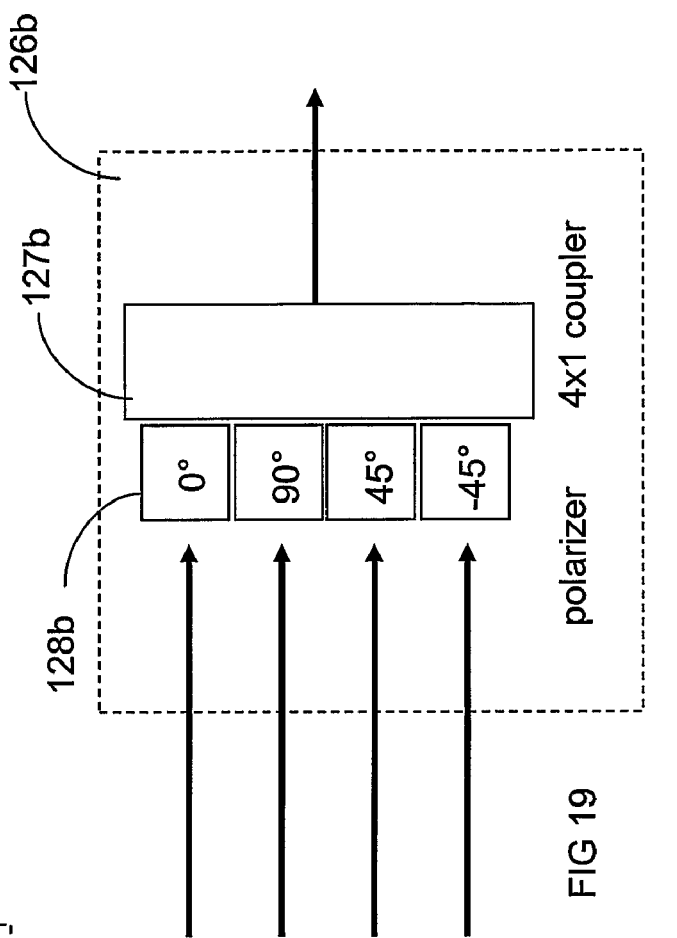

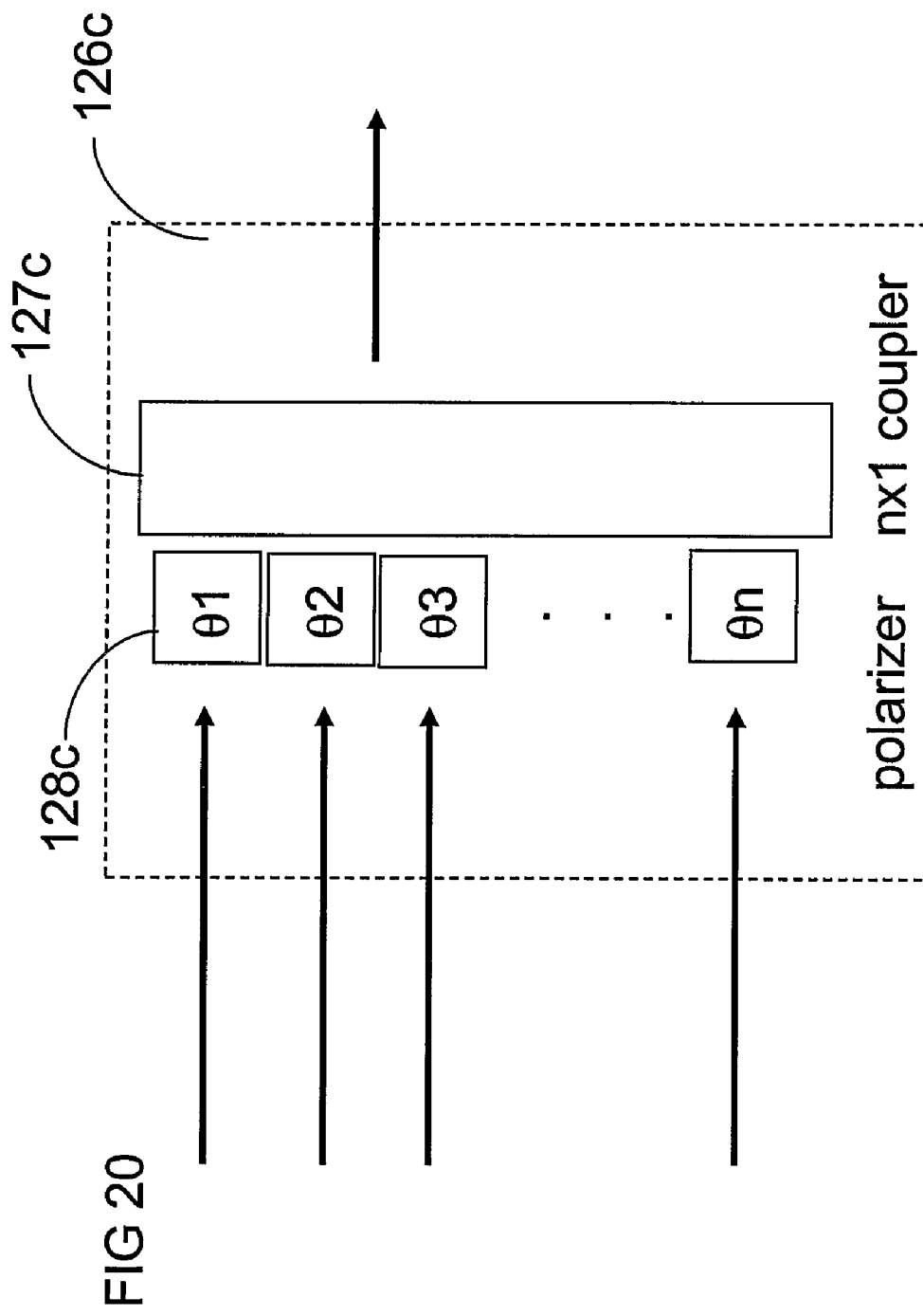

PHASE RESPONSIVE OPTICAL FIBER SENSOR

This application is a continuation-in-part of application Ser. No. 10/911,326, filed Aug. 4, 2004, now U.S. Pat. No. 7,139,476. This application claims the priority of U.S. provisional applications Ser. No. 60/580,005, filed Jun. 15, 2004; Ser. No. 60/587,484, filed Jul. 13, 2004; Ser. No. 60/599,006, filed Aug. 5, 2004; and Ser. No. 60/650,836, filed Feb. 7, 2005.

BACKGROUND OF THE INVENTION

1. Field of the Invention

The invention concerns techniques for detecting and accurately determining the location of a physical disturbance. Input signals are coupled in two opposite directions along a waveguide, through multiple signal paths, at least one such path traversing a detection zone. The waveguide, for example, can consist of one or more optical fibers. Multiple signal paths can be provided by distinct signals traveling in different fibers, and/or multiple signal paths can be provided using different modes of signal propagation in one or more of the same fibers.

In exemplary applications of the inventive techniques, optical fibers are routed around a security perimeter, along or across a road or path, coextensively with a power or signal transmission line, on or near a pipeline, etc. A disturbance such as sound or vibration from nearby activity changes the propagation conditions of the light signals carried in the multiple signal paths, simultaneously locally affecting the signal paths in both opposite directions. A phase relationship change occurs for the signals carried along the multiple signal paths in each of the two opposite directions. The change is carried along in the signals propagating away from the point of the disturbance in both directions. The propagation time difference, between appearances of the corresponding changes in the phase relationship at each end, is determined and used to resolve the location.

According to an inventive aspect, the disturbance is detected and located from a time variation in phase relationship between the signals carried along different signal paths and for each of the counter-propagating signal directions. A phase responsive receiver is used to obtain the phase relationship between signals on different signal paths. The phase responsive receiver comprises at least one beam combiner and at least two detectors to mix and to detect the signals from at least two signal paths, respectively.

Preferably, the beam combiner, such as a bidirectional coupler, functions as a beam splitter for producing multiple input signals paths in one direction and also forms an optical interference node at the receiving end for the signals propagating in the opposite direction. The arrangement can be symmetrical, with couplers at each of the ends splitting signals into multiple paths directed toward the opposite ends, while receiving and interfering the signals from the opposite end. Through the beam combiner, the received-and-interfered signals produce at least two phase-related intensity responses for each of the phase responsive receivers. The two intensity responses provide independent phase-related variable values when applied to detectors. These values can be used to obtain the phase relationship between signals carried along different signal paths. Two phase relationship signals are obtained, preferably as successions of data samples representing phase versus time, for the signals in each of the opposite directions, as affected by the disturbance.

The beam combiner can be a three-by-three fused fiber coupler, or an n-by-m coupler, a two-by-two coupler with polarization dependent elements, or multiple cascaded couplers. The light levels at the detectors are sampled and processed by techniques involving at least two independent phase-related variables, modeled and preferably normalized and reoriented using multi-dimensional data analysis techniques as described herein. The techniques discriminate for disturbance-induced variations in phase relationship, as a function of time, for each of the counter-propagating directions. A correlation function then matches the corresponding variations of phase versus time for the opposite directions, deriving a differential propagation delay. The differential delay enables accurate resolution of the location of the physical disturbance.

2. Prior Art

A security system should detect and provide information about any intrusion into a protected area or facility. An advantageous system should discreetly detect even modest physical disturbances, and report the location of the disturbance so as to permit corrective action to ensue promptly.

One technique for locating a disturbance is by determining the difference in timing between the arrivals of effects of the disturbance, in two counter-propagating signals that are both affected by the disturbance. A relative delay in arrival of the disturbance induced effects in the signal propagating in one direction versus the other direction indicates a longer propagation distance from the disturbance to the receiver, where the signal is detected. Measuring the delay can permit one to calculate an apparent location of the disturbance. This technique is described for example, in British Patent GB 1,497,995—Ramsay, entitled "Fiber Optic Acoustic Monitoring Arrangement."

Optical fiber has inherent advantages as a waveguide, such as low loss, immunity to electromagnetic noise and other characteristics, which are useful in remote sensing. The measurement of the disturbance effects in Ramsay utilizes an interferometer or interference sensor. An example of an interference sensor is the Mach-Zehnder interferometer, which has been applied to acoustic sensing, magnetic sensing, temperature sensing, pressure sensing, structure monitoring, etc, including using optical fibers, as described in "Overview of Mach-Zehnder Sensor Technology and Applications" by Anthony Dandridge and Alan D. Kersey, Fiber Optic and Laser Sensors VI, Proc. SPIE Vol. 985, pp. 34-52 (1988).

In addition to GB 1,497,995—Ramsay, cited above, the publication "Fiber Optic Distributed Sensor in Mach-Zehnder Interferometer Configuration" by Bogdan Kizlik, TCSET'2002 Lviv-Slavsko, Ukraine, proposes a similar location resolving technique. Recent U.S. Pat. Nos. 6,621,947 and 6,778,717 describe a perimeter defense system also based on this principle.

These prior art teachings produce an interference intensity signal versus time for each of two opposite signal paths, and seek to determine the location of the disturbance from the difference in propagation time over two counter-propagating signal paths, between the appearances of corresponding time variations at receiving ends for the opposite signal paths. There are problems, however, when attempting to use optical fiber waveguides and the like for location detection in this way. Polarization induced effects can reduce or defeat the usefulness of these prior techniques for discerning the location of the disturbance.

Light waves interfere only when there is some correspondence in the state of polarization, permitting the beams to interfere. Two light waves that are orthogonally polarized cannot interfere. Over plural paths between a light source and two or more detectors, the birefringence of the fibers forming an optical path can change the state of polarization and phase characteristics of the light beams. The birefringence of an optical fiber may be small compared to its refractive index. Nevertheless, an accumulated polarization effect arises, particularly over a long distance. Prior art systems cannot perform consistently, and in some circumstances do not perform at all, because the interfering optical beams vary from time to time between more or less parallel and more or less orthogonal states.

Variable beam interference conditions caused by polarization state changes are recognized as a problem in single light path interferometers, the problem being known as polarization-induced fading. The problem is described, for example, in "Polarization-Induced Fading in Fiber-Optic Sensor Arrays" (Moshe Tur, Yuval S. Boger, and H. J. Shaw, Journal of Lightwave Technology, Vol. 13, No. 7, p 1269, 1995). This publication seeks to enhance the visibility of the interference beam in a single-channel fiber based interferometer, where the light travels along a single direction.

Polarization induced phase shift, which is caused by the mismatch of the polarization of the interfering beams, is a somewhat different effect from polarization induced fading, but causes measurement problems, because polarization induced phase shift can be difficult to distinguish from other factors. If there is a polarization induced phase shift, the interference intensity signals at the detectors for the two counter propagating signals may not correlate closely. The technique of calculating a location for the disturbance relies on identifying two corresponding variations in amplitude over time, and then measuring the difference in time of arrival between the two counter-propagating signals. Such a measurement is difficult and potentially inaccurate, if variations in the two signals cannot be properly matched.

In the prior art interferometer system, signal phase conditions are varied by the disturbance to produce variations in interference amplitude. But the swing in the interference output signal is not exclusively or linearly related to the change in relative phase caused by the disturbance. The interference amplitude is affected by changes in polarization states which generally are different for the two signal directions because of differences in the polarization effects in the two counter propagating directions. The interference amplitude is not uniquely related to the relative phase relationship between interfering beam along different paths. For these reasons, a disturbance locating security system as in GB 1,497,995—Ramsay may be undependable or may need regular polarization adjustment. Measurement failure from polarization induced effects is an imminent danger. The correlation of time varying interference signal signatures for a given disturbance for the two opposite signal paths produces uncertain location measurements due to unpredictable polarization effects. For all these reasons, the system dependability and accuracy are less than might be desired for security purposes.

In terms of structure, the prior art technique for coupling signals typically employs two-by-two optical couplers, such as fused fiber junctions, for splitting and/or for combining light signals.

It would be advantageous for the location detection purposes discussed, to enable an accurate determination of phase variations between two received signals applied as two inputs to a coupler, and to do so free of complications from polarization fading and phase shift. What is needed is additional independent variable information whereby the two independent output variables can be derived to permit the effects of phase to be discriminated from the effects of polarization.

The present invention avoids detrimental effects of polarization induced fading and phase shift. Conditions are established that provide a robust response notwithstanding time changing polarization transformation characteristics such as birefringence. In certain embodiments, these conditions are established by providing coupler outputs that are characterized by a phase difference, permitting an analysis with the benefit of at least two and optionally additional independent variables by which phase effects are discriminated from polarization effects. A multi-dimensional data analysis technique is used, as illustrated by optional techniques in the disclosure, demonstrating how independent variables are translated substantially exclusively to phase angle as a function of time. The adverse effects caused by polarization are reduced to signal to noise ratio effects and can be readily avoided. The invention is practical, dependable and effective in perimeter security systems, as well as in other distributed sensing purposes.

SUMMARY OF THE INVENTION

In one arrangement, a distributed location resolving sensor system according to the invention comprises four major parts: a waveguide, a light source, a phase responsive receiver, and a signal processor.

The waveguide includes at least two signal paths, which in different configurations can be distinct signals traveling in different fibers, different modes of signal traveling in the same fiber, etc. The waveguide supports two counter-propagating signal directions. The waveguide is arranged such that at least one signal path in each direction is affected by a disturbance in the detection zone. The effects of the disturbance include a phase variation effect that propagates in both directions beyond the disturbance and is sensed at a phase responsive receiver for each of the counter-propagating signal directions. The input signals producing the input or carrier signals for the two counter-propagating signal directions can be derived from different light sources, or can be derived from the same light source by the use of one or more beam splitters.

The phase responsive receiver is capable of determining the phase relationship between the signals on different signal paths. The phase responsive receiver has a beam combiner operative to combine different signal paths, and at least two detectors. An important aspect of the phase responsive receiver is that the phase responsive receiver can generate and detect at least two independent variables that both concern phase-related intensity responses. From these at least two variables, information can be derived from which the phase relationship is resolved unambiguously.

The processor is coupled to sample data from the at least two detectors of the phase responsive receiver, and for each of the opposite directions. The two independent intensity responses can be processed according to a novel multi-variable data analysis technique, usefully modeled using corresponding multiple dimensions of a coordinate system, to obtain the time varying phase relationship as explained in detail hereinafter.

In the event of a disturbance, a phase variation occurs due to acoustic effects, vibration and the like in a detection zone. The disturbance can be detected and the location can be obtained through correlation techniques to match corresponding time variations in the phase relationships between signals along different paths for each of two counter-propagating signal directions, at different times. The differential delay is resolved to identify a location in the detection zone, namely that location at which the difference in propagation delay times for arrival of correlated phase variations at the phase responsive receivers for the two opposite directions is attributable to a difference in propagation path lengths.

The perturbation in signal propagation from the disturbance occurs in the phase relationship between the at least two signals carried on different paths propagating in each opposite direction. Thus at least one signal path in each direction traverses the detection zone. In respective embodiments, one or both paths in each opposite direction can traverse the detection zone to be subjected to a disturbance that produces a time variation in phase relationship for each opposite direction, originating at the location of the disturbance. By using phase responsive receivers as described, and deriving two independent phase related variables for each end, the inventive technique derives the phase relationship for the signals carried on different paths in both opposite directions, in a manner that is virtually free of confounding influences arising from the mismatch of the state of polarization of the signals carried on different paths for respective light signals directions.

One example of the phase responsive receiver uses changing polarization characteristics of the combined beam as a parameter that is sensed and from which the phase relationships are determined and hence the location of the disturbance is resolved. This is one example of an effect that involves a time variation in phase relationship.

In an example that actually uses polarization, the mutually orthogonal components of a light signal can be regarded as two beams and the polarization state can be regarded as a measure of the phase relationship between two beams, namely the orthogonal components that vary in phase relationship to define different polarization states. Techniques are disclosed herein for extracting the phase relationship between the members of the pair, without complications resulting from the use of polarization state as a variable that is related to relative phase.

The change in polarization characteristics of the combined beam is directly related to the change in phase relationship of the combining beams. Polarization can be a confounding factor in interference intensity sensing systems. However, the invention solves potential difficulty with polarization induced signal fading and polarization induced phase shift by reliably detecting phase relationships independent of polarization state.

In another example, the phase responsive receiver has couplers, preferably arranged symmetrically with respect to the detection zone, each coupler having two or more outputs and the detector responding to the polarization attribute of the output light so as to derive the at least two independent output signals from which two independent phase variable values are available.

In yet another example, the phase responsive receiver has couplers, preferably arranged symmetrically with respect to the detection zone, each coupler having three or more outputs and the detector responding to at least two of the outputs so as to derive the at least two independent output signals from which two independent phase variable values are available.

Another example of the phase responsive receiver employs two or more cascaded 2×2 couplers. Although this example uses 2×2 couplers, the cascading of the couplers produces the desired two independently-varying intensities, both of which are related to phase, in a manner similar to employing two of three outputs from a 3×3 coupler. Other coupler arrangements also can be used to obtain two independent variable values related to phase, from which the phase relationship of the two signals can be computed or otherwise derived for each opposite signal path. Accordingly, additional examples of phase responsive receiver embodiments operative as described herein and within the scope of the invention will become apparent to those skilled in the art in view of this disclosure.

An inventive aspect is the characteristic of the phase responsive receiver to generate at least two independent variables values applied to two detectors for each opposite signal direction. The two independent variables have phase related intensity responses but are useful as demonstrated by solutions to simultaneous equations, to produce a variable that is proportional to phase. An exemplary and nonlimiting technique to achieve this result, which is exemplified by 3×3 couplers as well as by cascaded 2×2 couplers and other similar arrangements, is to provide structures wherein the outputs have inherent phase relationships, as described herein.

The invention bidirectionally uses a change in phase relationship between two signals, instead of an intensity response from interfering two signals, as the parameter sensed from a disturbance occurring in the detection zone. Detecting and timing the difference between corresponding variations in phase relationship can be accomplished more dependably than attempting to make corresponding use of an interference signal, the amplitude of which does not uniquely correspond to a phase angle, and in any event consists of only a single variable value that may be adversely affected by polarization effects.

A time variation in an interference intensity response (as in the prior art) occurs when there is a change in the phase relationship between two interfering input signals. The interference intensity response and the phase relationship do not have a one to one correspondence. Thus even assuming that a disturbance produces an identical time-change phase signature for signals in both signal directions, variations in interference intensity provided by interfering signals for each direction cannot be expected to have the same time-change amplitude signatures because of confounding polarization issues. According to the inventive technique, on the other hand, an object is to derive the time-change phase relationship per se, thus benefiting from substantially identical temporal signatures in the operative parameter, namely phase.

In the inventive technique described, the signal levels from which phase relationships are derived contain polarization effects. In the inventive technique, polarization variations affect an offset level between the two phase responses. As an offset, the effects are readily subtracted away in data processing. A comparable polarization related effect in prior art interference intensity measurements may produce different intensity responses for the counter-propagating signal directions because of the nonlinear and non-monotonic relationship between phase relationship and the intensity response.

According to the inventive technique, the at least two independent intensity responses are processed mathematically to produce the phase relationship using multiple independent variable (multi-dimensional) data analysis techniques. At least two independent variables are derived respecting phase and together the variables permit the phase angle itself to be derived. Polarization mismatch affects the phase relationship as an offset. Even polarization state variation over time in many instances is a low frequency effect compared to the time scale of most forms of disturbance to be detected (e.g., acoustic noise), and can be treated much the same as a steady state offset. The time signatures of the changing phase relationships for the counter-propagating directions are substantially identical in shape by this technique. The signatures correlate strongly between the two counter-propagating directions.

Several exemplary configurations of the phase responsive receiver are described herein, each useful in measuring a phase relationship by deriving plural independent values that together permit a resolution of phase. One technique is to measure the intensity response of different polarization components. The signal paths can be combined using a polarization sensitive combiner (e.g., a walk-off crystal), or a polarization insensitive combiner (e.g., a fused fiber coupler). The two independent intensity signals can be two polarization components from the same output port, and/or two polarization components from different output ports.

Another example is to use a coupler with three or more output ports, or cascaded multiple two-by-two couplers. For this purpose, the three-way couplers can comprise fused fiber couplers dimensioned or similarly configured so that although the sum of all three output intensities is constant, any two output intensities are independent from each other. The distribution of the power between the three output ports is determined by the phase relationship of the two signals along two different paths. Differences in phase displacement through the coupler to the detectors and the independence of said two of three coupler outputs, produces the information needed for deriving the phase relationship between two signals coupled to two of the three inputs of a 3×3 coupler, or both inputs of a cascaded 2×2 coupler.

The inventive technique can be applicable in test measurement apparatus for making direct phase measurements. The inventive technique is useful for sensing movement, acoustic noise, shock or vibration, variations in pressure, and similar physical phenomena that may occur at distributed points along a waveguide carrying two signals in one direction, and as applied to counter-propagating directions allows the location of such phenomena to be determined.

The "line" through the detection zone could be, without limitation, a straight line, a sinuous arrangement, a full loop or partial perimeter, an arbitrary pattern that passes successively through points of interest, a member of an array such as a zigzag or raster pattern, etc. The waveguide can be continuous or a succession of serial segments. The waveguide can be a permanent or temporary installation, placed to establish a detection path or to monitor an existing path such as a fence line, a road, a pipeline, a power or signal transmission line, a building perimeter or building component, a succession of monitored portals such as windows or doors, etc. The path can cross or run parallel to the path or to the expected movement of a person or item to be detected. The occurrences produce detectable local changes in physical properties in an optical waveguide, such as an optical fiber.

Short term changes in physical conditions (generally termed a disturbance) of a character that produces a change in signal propagation conditions, result in similar short term deflection in the phase relationship of the signals carried on different paths of the counter-propagating signal directions. The short term nature of the conditions to be detected can permit longer term changes and drift to be treated as offsets that can be substantially eliminated in a differential calculation relying on the time changing signature of a brief disturbance. Disturbances to be detected in a security system, for example, are normally associated with physical events associated with persons or animals or things (e.g., vehicles) moving and producing vibration in the vicinity of the waveguide carrying the counter-propagating pairs of signals. Only one path or multiple paths of each signal direction might be affected, the disturbance nevertheless producing a time variation of phase relationship signature between two signals carried on different paths from which a phase relationship signal is derived.

A number of alternative configurations are possible and several examples are discussed in detail herein. These may advantageously include or involve polarization sensitive or insensitive detection, tuning of the input signal wavelength, using one or more fibers or fiber transmission modes to carry the beams, splitting beams from one or more coherent laser sources or one or more other light sources, splitting and recombining beams using various coupler configurations, such as 3×3 couplers, cascaded couplers, and other variations.

Although the disclosed technology can be applied to various applications including position sensing situations, this disclosure uses the example of optical fiber based perimeter security as a non-limiting example of a particularly effective use. Inasmuch as an optical waveguide is easily placed to follow various paths, the same technique can be used to extend a detection path between arbitrary zones, to provide a two or three dimensional detection area, etc.

These and other objects will be made apparent by the following discussion of exemplary embodiments and variations, from which further variations within the scope of the claimed invention can be inferred.

BRIEF DESCRIPTION OF THE DRAWINGS

Shown in the drawings are exemplary embodiments to illustrate the invention as presently preferred. The invention is capable of these and other embodiments, and it should be appreciated that the scope of the invention is defined by the claims as opposed to this description of illustrative examples. In the drawings.

FIG. 6 is a time plot of typical Stokes parameter traces shown in the Poincaré sphere using a polarization insensitive beam combiner for each counter-propagating direction, demonstrating typically different polarization parameter trajectories for the two directions.

FIG. 8 shows a schematic interferometer, employing a free space polarization sensitive beam combination device, using a polarizing beam splitter.

FIG. 9 shows an interferometer based on polarization sensitive beam combination using a polarization beam displacer.

FIG. 12 schematically compares two special situations when only one beam is coupled into the detector.

FIG. 15 schematically illustrates a bidirectional polarization based fiber distributed sensor.

FIG. 16 shows a technique for detection of phase using two polarization sensitive detectors and a polarization insensitive beam splitter.

FIG. 17 illustrates use of a patterned liquid crystal cell as a polarization controller.

FIG. 18 is an example showing a two-beam polarization sensitive beam combiner.

FIG. 19 is an example showing a four-beam polarization sensitive beam combiner.

FIG. 20 is an example showing an n-beam polarization sensitive beam combiner.

DETAILED DESCRIPTION

The invention provides a technique for collecting signals representing the time variation of the phase relationship between the multiple signals carried on different paths for counter-propagating light signals, useful for determining the location along a waveguide at which a detectable occurrence has disturbed light propagation conditions locally. The disturbance locally affects both counter-propagating optical signals simultaneously. The disturbance is detected after the affected light beams have propagated away from the disturbance to receivers at opposite ends of the counter-propagating signal paths. Such propagation occurs along paths of potentially different length, based on whether the disturbance occurs closer to one receiver or the other. The rate of signal propagation is known. The difference in propagation distance results in a difference between the times at which the disturbance arrives at the receivers disposed along the paths of different length.

Figure 1:
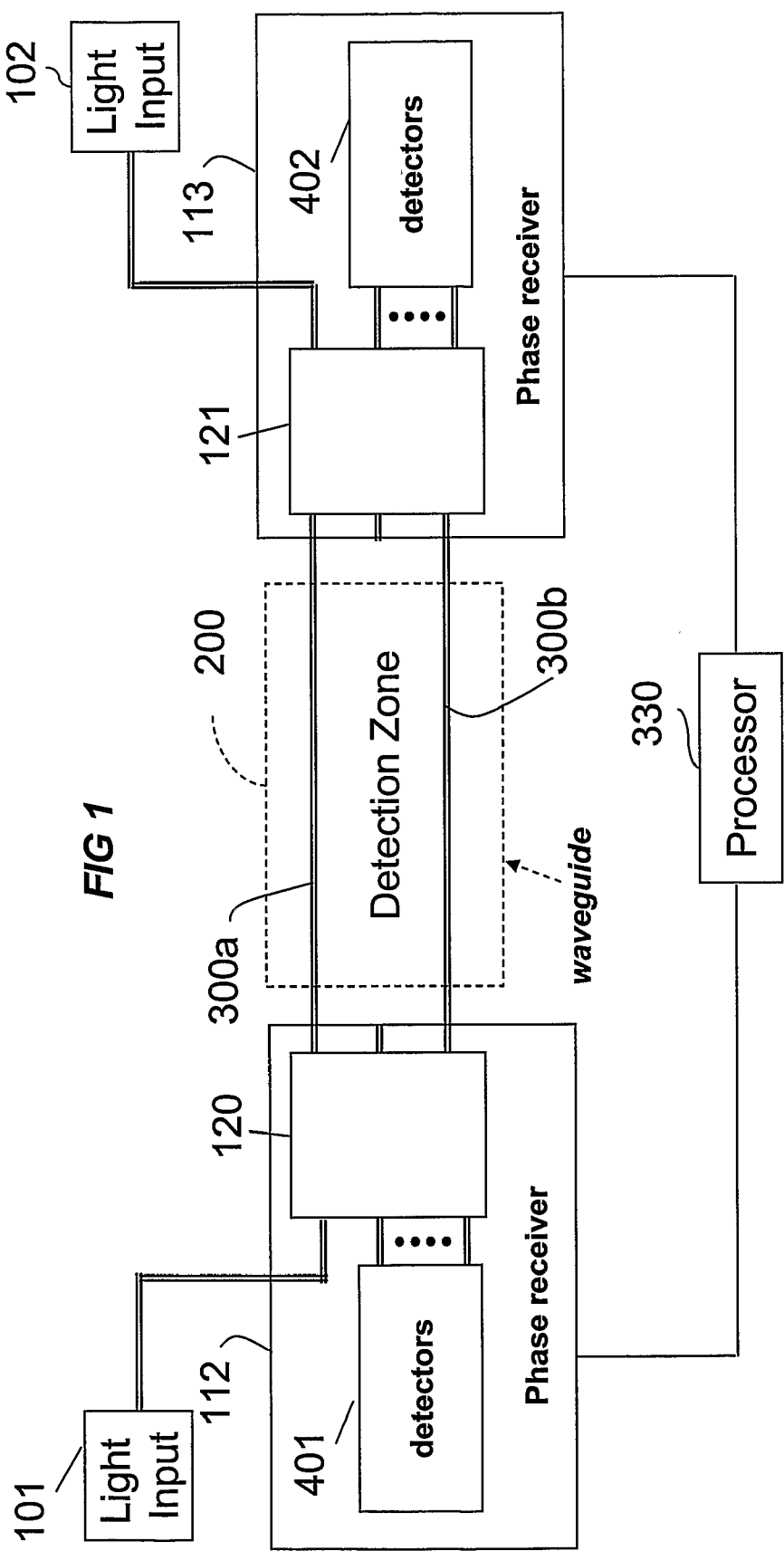
FIG. 1 is a block diagram of a distributed fiber sensor according to the invention.

Referring to FIG. 1, the disclosed system contains four major parts: the waveguide, the light source, the phase responsive receiver, and the processor. The waveguide comprises at least two signal paths 300$a$ and 300$b$, and supports counter-propagating signal directions. In this example, preferably the counter-propagating signals share the same paths in both directions. At least one beam for each counter-propagating optical channel passes through the detection zone 200 in opposite directions. Thus at least that one beam for each direction is affected by the disturbance, and a phase variation occurs over time. Each direction has at least two signal paths, one or both of which can pass through zone 200. The waveguide can have more numerous paths as well, provided that there is a phase variation signature produced. The light source can be separate light sources 101 and 102, or two or more signals can be split from the same light source.

In order to work most effectively, it is necessary to obtain substantially identical but time-shifted signatures of the disturbance signal in two counter-propagating signals, with high correlation so as to permit sure, fast and accurate measurement of the lead/lag time (differential delay) in receiving the signatures. This is accomplished according to the invention by using a phase responsive receiver, 112 and 113, one disposed on each end of the waveguide (at least functionally at each end if not also physically placed there). The detected signals are further processed to obtain the location of the disturbance. For this purpose, a processor preferably employs a multi-dimensional data analysis technique using independent variable data derived from the manner in which the signature signals are received and processed.

According to different aspects of the invention, the phase responsive receiver can be accomplished in exemplary embodiments using polarization sensitive intensity detection arrangements, optical couplers that have three or more output ports, and/or cascaded multiple couplers. These and similar techniques are used for determining the phase relationship of the two (or more) signals in each counter-propagating direction.

The phase responsive receiver detects at least two independent but phase related intensity responses for each counter-propagating signal direction. The measured intensities are then processed and analyzed by the processor using a multiple variable data analysis technique (illustrated herein as a multi-dimensional technique for plotting circular trajectories) to resolve the phase relationship between multiple signals along different paths.

The invention uses the time variation of phase relationship as opposed to the time variation of intensity responses as in the prior art. The prior art cited above typically uses interference intensities between two paired signals traversing a detection zone, or between a signal traversing a detection zone and a reference signal, as the parameters of disturbance detection and location. By reliance instead on a phase variable, preferably derived according to particular inventive techniques, the invention represents a substantial improvement over known location-discerning techniques using optical waveguides, as described in the cited prior art. For example, the interference intensity technique described in GB 1,497,995—Ramsay is implemented by adjusting delays to match the shape of interference intensity signals for two counter-propagating directions. Phase variation effects are likely inherently to produce the same or similar phase variation signature shape for counter-propagating directions. Intensity variations in opposite directions are not likely to provide similar or easily correlated time signatures, due to the various polarization induced effects which are generally different for the two counter-propagating directions. Polarization typically affects phase variation measurements by adding a constant offset, which is can be subtracted away and removed, particularly in a differential data process.

According to one inventive aspect, the waveguide can be structured in such a way that the extent of the polarization change caused by the disturbance is substantially smaller than the corresponding phase relationship change, as the beams in each direction are combined. On the time scale applicable to acquiring data representing a typical disturbance, the polarization states for each of the combining beams remain more or less constant. On the other hand, the relative phase relationship changes to produce a distinctive signature of changing phase versus time. The extent of polarization mismatch changes, but over a long period of time. Difference in polarization induced phase shift from time to time does not impose a problem in the present invention, because the polarization induced contribution to phase shift will not change the shape of time varying phase relationship response.

One advantageous embodiment of the invention uses a 2×2 coupler with at least two detectors that are configured to detect the intensity response of two polarization components for each of the two counter-propagating directions of the waveguide. The coupler in that embodiment can be polarization sensitive (e.g., a walk-off crystal) or polarization insensitive (e.g., a fused fiber coupler). The two polarization components can be different polarization components derived from the same output port of the coupler, and/or two polarization components obtained one from each of the output ports. A change in polarization properties produces a related change in the phase relationship between the combining beams. The change in polarization properties can be measured by the use of a polarimeter and/or other polarization sensitive detection scheme, as one technique for sensing a changing phase relationship produced by a disturbance in the detection zone.

Another advantageous embodiment of the invention uses one or more couplers configured to provide three or more output ports. One example of such a configuration comprises a fused fiber 3×3 coupler. Another example is a series of cascaded couplers, such as two cascaded 2×2 couplers wherein the outputs are selected from output ports of the cascaded couplers. Various such arrangements are possible and will provide at least two independently varying values that both are related to phase. At least two detectors for each of the oppositely propagating signals are coupled to measure these at least two independent but phase related intensity outputs from two output ports. The detectors can be photodetectors whose outputs are repetitively sampled and digitized.

Preferably, the 3×3 coupler is a fused fiber coupler characterized by an equal intensity splitting ratio for the three ports. Any two of the intensities can be further processed to reveal the phase relationship of the two beams along different paths before interference.

In the following, both embodiments are discussed in detail for illustration purposes. It should be understood that other embodiments will be apparent to those skilled in the art and are encompassed according to the appended claims.

EXAMPLE

Phase Detection Based on Polarization Sensitive Detection

In this example of certain representative embodiments, methods and apparatus are provided to manage, and moreover to exploit, variations in polarization aspects of two counter-propagating light signals, in discerning the location along an extended waveguide at which a detectable occurrence has locally disturbed light propagation conditions. According to an aspect of the invention, a polarization-based exemplary system is provided that uses polarization effects in the counter-propagating optical signals, as the operative parameter detected and employed to calculate the location of the disturbance. The inventive system is constructed so that the two counter-propagating polarization signals are processed to obtain an intrinsically matched temporal variation of the signal, which is significantly different from an intensity-only system that might otherwise behave similarly, but only in the special case where it is assured that the relative polarization relationships of the two interfering beams, prior to interfering, are substantially identical for the two counter-propagating directions.

The output state of polarization of interfered beams is a parameter that is related to the phase difference between these two beams. According to an aspect of the invention, this effect is used to discern and to locate a phase disturbing event in a counter-propagating configuration, without difficulties caused by polarization related fading and polarization-induced phase shift.

Figure 2:
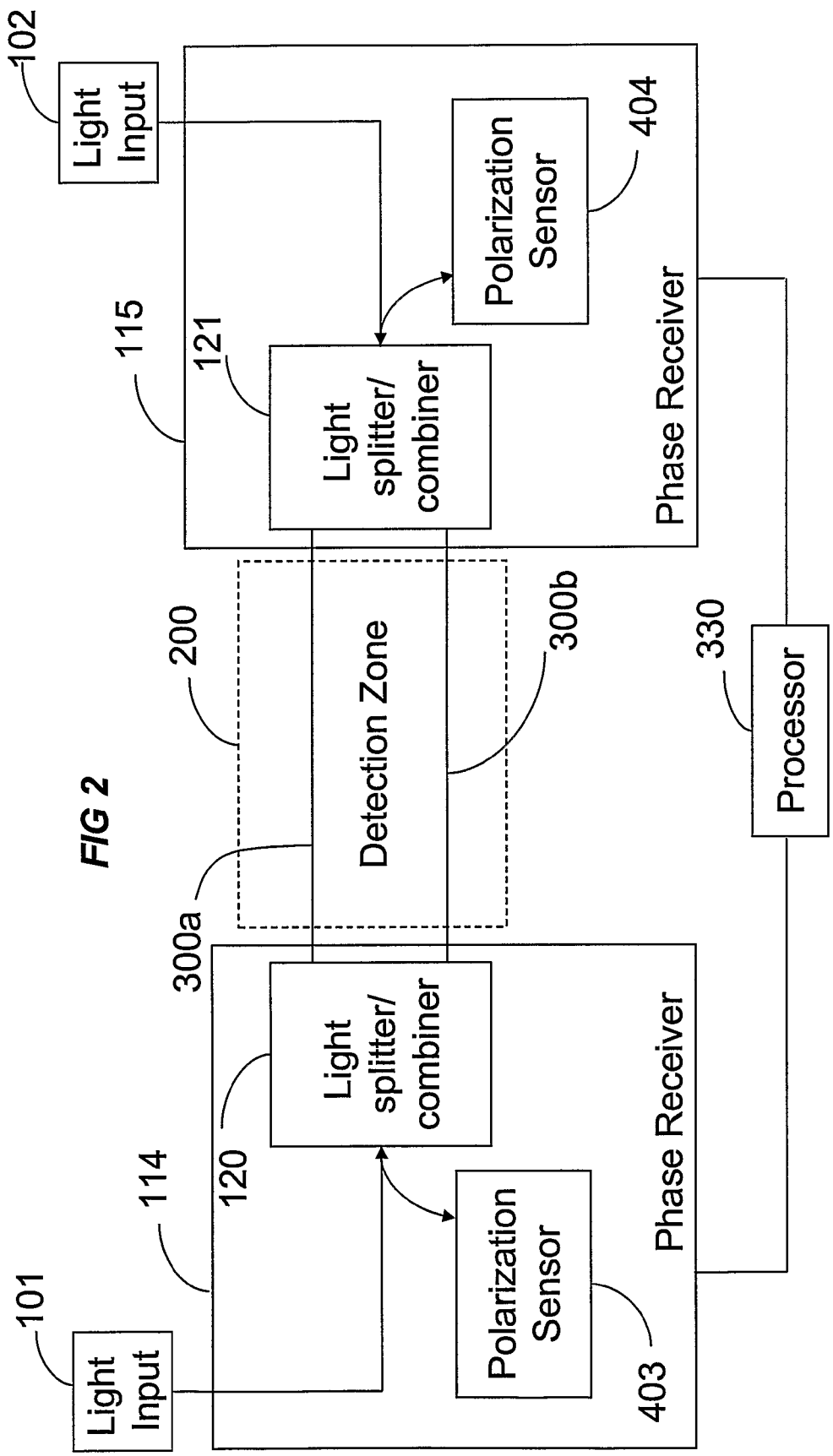
FIG. 2 is a block diagram of another arrangement of the distributed fiber sensor, using polarization-based phase responsive receiver.

Referring specifically to FIG. 2, a block diagram shows an inventive polarization-based distributed sensing system, wherein an object is to determine the location of a physical event causing a disturbance at some point along an optical fiber waveguide passing through a detection zone 200. Light sources 101 and 102 can be derived from different sources or from the same light source using a power splitter. The signal from the respective source 101 or 102 in each case is separated by a phase receiver 114 and 115, which includes beam splitter/combiner 120, 121 and polarization sensitive sensors 403, 404. Each phase receiver 114 and 115 is a polarization sensitive measurement unit, which comprises at least one beam splitter/combiner and at least two polarization sensitive sensors. The beam splitter (120, 121) can be a polarization sensitive component or a polarization insensitive component. The beams are recombined by beam combiners 121, 120, respectively. In this arrangement, the same beam splitter/combiners 120 and 121 work in one direction leading toward associated receivers to join the multiple incoming beams, and work in a second or opposite direction to separate one beam from the respective source 101 or 102 into multiple beams that propagate through the detection zone toward the receiver at the other end.

In the receiving (combining) direction, the optical signals from the combined optical channels are detected by polarization sensitive sensors 403, 404 functioning as the phase receivers. The receivers extract at least some information with respect to the state of polarization of the combined beams. The polarization receivers are coupled to a data processing unit 330, which determines the time difference between the first and second emergences of a corresponding change in the state of polarization, for the beams in the respective counter-propagating directions. This time difference can be used to determine the location of the disturbance along the length of the detection zone. In the case of a disturbance due to a physical intrusion, for example, the location of the intrusion can be determined and reported by a variety of means including but not limited to a display, internet protocols, cell phones etc.

Figure 3:
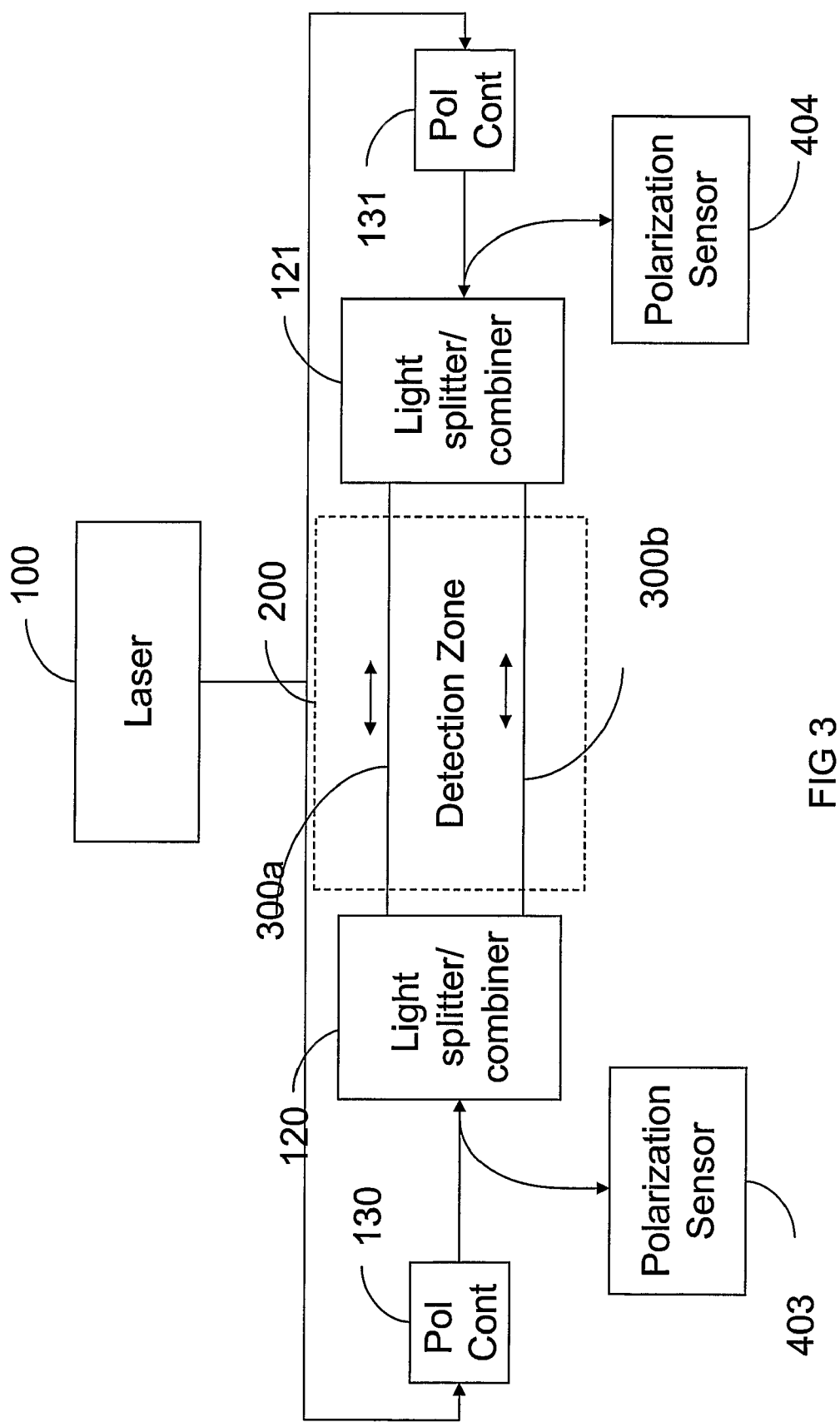
FIG. 3 is a block diagram of another arrangement of the distributed fiber sensor using polarization dependent phase responsive receiver, wherein a single light source is used to generate the counter-propagating signals. Polarization controllers are advantageously included.

FIG. 3 is a block diagram showing another exemplary arrangement of a polarization based remote fiber distributed sensing system embodiment according to the invention. In this arrangement, the light signals for the two counter-propagating directions or channels can be derived from the same light source 100. Throughout the drawings, the same reference numbers and labels have been used where possible to identify the same or functionally similar elements. Therefore, the description shall rely where possible on the previous descriptions of the same functional blocks instead of describing them anew in each figure or instance.

The embodiment of FIG. 2 has a plurality of polarization controllers 130, 131, placed so as to advantageously control the optical signals from the laser source 100 into the light splitter/combiners 120, 121 and as emerging from the splitter/combiners 121, 120 (operating oppositely splitters and as combiners) into the respective polarization sensors 403, 404. Alternative specific arrangements for polarization controllers also exist and can be used, the alternatives being apparent to persons skilled in the art.

According to an inventive aspect, the phase relationship between the combining beams along different paths is determined by measuring the change in polarization properties of the combined beam. A change in the phase difference between the two beams in the detection zone causes the output polarization properties of the combined beam to change.

A disturbance in the detection zone produces a change in polarization properties for the two beams in both counter-propagating directions. However, the changing polarization states of the beams typically are not equal for both directions. The change in polarization properties for the combined beams thus is not a matter of, the same beam states occurring in both directions, changing in the same way, and producing the same changing output polarization state. An aspect of the invention is to detect and to correlate changes in both beam directions that are accountable to the same disturbance, specifically to respond to phase variations that occur in both signals, but to do so without adverse polarization effects and in a manner that discriminates specifically for corresponding changes in phase.

Polarization state changes can be characterized as changes in the values of Stokes parameters that can define a unique polarization state. Stokes parameters are defined as a set of four numbers: S0, S1, S2 and S3. S0 is defined as the total intensity. S1, S2 and S3 encode the respective intensity differences between orthogonal states of polarization in three ways, namely: 0° and 90° linearly polarized states; +45° and −45° linearly polarized states; and right-handed and left-handed circularly polarized states, respectively.

In order to characterize the state of polarization of light in a manner that is intensity independent, the Stokes Parameters are often normalized such that the S0=1. This is accomplished by dividing all four Stokes parameters by S0. The intensity dependent Stokes Parameters is usually referred as the un-normalized Stokes Parameters (or intensity dependent Stokes Parameters), which is the preferred way of representing the polarization in the present embodiment of the invention. In the following discussion, Stokes parameters should be assumed to refer to the un-normalized (or intensity dependent) version Stokes parameters. Where reference is to be made to Stokes parameters that are normalized, the context will refer to normalized Stokes parameters.

In one embodiment of the invention, the beam combiners 120 and 121 combine the incoming beams in a polarization insensitive way. A change in the phase difference between the two beams in the detection zone causes the output polarization properties of the combined beam to change. When the two beams are orthogonally polarized, a phase change between the two beams causes the intensity dependent Stokes vector to trace a circular arc as plotted (or otherwise encoded) on the Poincaré Sphere (a three dimensional plot of the Stokes parameter values). When the two combining beams are parallel polarized, a phase change between the two beams causes the intensity dependent Stokes vector to trace a line. When the two detection beams are arbitrarily polarized (e.g., somewhat parallel and somewhat orthogonal), a phase change between the two beams causes the intensity dependent Stokes vector to trace an ellipse.

According to an inventive aspect, the phase relationship between the two beams, even of arbitrary polarization, can be determined by analyzing the elliptical trajectory. For example the plotted (or otherwise encoded) values on the ellipse trajectory are projected or replotted (or otherwise encoded) as a circle. An angular difference can be determined between any plotted (or otherwise encoded) points representing states of polarization. The phase difference between the two beams can be obtained from that angular difference, except that there is a constant offset having a value dependent on the polarization mismatch between the two beams. The data can be processed, for example, to monitor for change in phase.

In general, according to one aspect of the invention, polarization dependent measurements need not be used to resolve a complete set of Stokes parameters. Other polarization measurement techniques can be employed in which only limited polarization related information is obtained, which information is nonetheless sufficient to encode the phase variations that occur for two counter-propagating beams.

In general, at least two polarization dependent intensity responses are obtained to resolve the phase relationship between the combining beams. This technique is generally useful as a phase measurement technique, and is particularly effective when used for both counter-propagating beam directions in the intrusion/disturbance detection system of the invention.

One example of obtaining at least two polarization dependent intensity responses comprises separately detecting the intensity of different polarization components (at least two) for one of two or more output signals from the beam combiner. It is also possible to detect the intensity response for two polarization components, one from each of two or more output ports. The different polarization components can be orthogonally polarized components, such as 0° and 90° linearly polarized components. Alternatively, the different components can be two other arbitrary polarization components, provided that the components are different and thus represent two independent variable responses that are related to phase.

In a case comprising measuring the intensity response of two polarization components, when the two combining beams are arbitrarily polarized, a phase change between the two beams causes the plotted (or otherwise encoded) relationship between the two detected intensities to trace an ellipse. A phase relationship between the two beams of arbitrary polarization can therefore be determined by analyzing the elliptical trajectory, for example by transforming the ellipse into a circle and calculating the relative angular difference between consecutive points on the circle. The phase difference between the two signals along different paths can be obtained from the rotation angle between the points, except for a constant offset value which is a dependent of the polarization mismatch between the two beams.

Other similarly applicable techniques for resolving phase relationships exist and now will be apparent to those skilled in the art. These and other techniques can be applied to each of the counter-propagating directions to determine the phase relationship between the signals on two signal paths in each direction. More particularly, the phase relationship is monitored over time, for example by sampling. A disturbance at some point in the detection zone alters the propagation conditions for at least one of the two beams along different signal paths in each of the two opposite directions. The disturbance thereby causes a time variation in the phase relationships between the two beams of both opposite signal pairs. The effect of the disturbance on the counter-propagating light signals is detected, after the light signals carrying the effect of the disturbance have propagated in opposite directions to the phase receivers. Depending on whether the disturbance occurred nearer to one end or another, the effect of the disturbance arrives sooner or later at one or the other phase receivers. The leading or lagging time shift and knowledge of the rate of signal propagation can be used in calculating the point at which the disturbance occurred. The use of the phase relationship between the members of the opposite signal pairs produces a similar and readily correlated phase-versus-time signature for the signal pairs in both opposite directions.

This technique is optimally free of polarization influences, even though polarization affects the oppositely propagating signals. If the states of polarization of two combining beams happen to be substantially parallel to each other, the resulting polarization trajectory can be highly eccentric, and possibly reduced into a straight line. This situation can be avoided by changing the input polarization by the use of the polarization controller 130 and 131, as shown in FIG. 2. Because polarization effects are partly a matter of wavelength, a tuning control can be included to permit a wavelength adjustment for repositioning the polarization transformation situations for the different light paths, such that the polarizations of the combining beams are made substantially different from one another instead of parallel.

In another embodiment, the beam combiners 120, 121 are polarization sensitive, combining orthogonal polarization components. This manner of beam combination results in a circular normalized Stokes Parameter trajectory on the Poincaré Sphere. A relative angular change of the polarization state in the trajectory plane is proportional to the phase difference between the two interfering beams. Therefore, according to an aspect of the invention, this change in polarization state can be detected and used as the parameter that is correlated for the counter-propagating signals. This technique likewise permits a disturbance in the detection zone 200 to be localized to the place at which the disturbance caused a change in optical propagation properties.

For a combination of orthogonal polarization components, the polarization trajectory can be circular but might not be a great circle on the Poincaré Sphere. The trajectory may have a diameter that is smaller than the diameter of the Sphere itself. The size of the circular trajectory on the Poincaré sphere is a function of the relative power between the orthogonal polarization components in the two beams that are being combined. If the intensities of the orthogonal polarization components being combined are equal to each other, then the circular polarization trajectory produced by a changing phase difference between the combining beams will be a great circle on the Poincaré Sphere. If these intensities become unequal, the circular trajectory is reduced in diameter compared to the full diameter of the Sphere. The angular position of points on the trajectory circle can still be determined, and such angular position provides a phase related variable.

According to an inventive aspect, the changes in polarization state around a trajectory on the Poincaré Sphere represent the parameter by which the location of the disturbance is resolved. The invention relies on this phase related variable and not on a variation in intensity produced by interference of the beams whose phase relationship is the variable of interest.

The precision with which a difference or change between polarization states can be resolved (namely the angular displacement between two points on the circle of polarization trajectory) is best when the trajectory circle has a large diameter. According to another aspect of the invention as explained below, the precision of the detection measurement can be maintained to an effectively high precision by taking steps to keep the trajectory circle large on the Poincaré Sphere, as obtained from changing polarization states. These steps, which are desirable but not necessary, include the effective management of the polarization controllers or the wavelength of the laser.

With counter-propagating beams, the same optical waveguide is interrogated from two different directions (or alternatively, coextensive plural optical waveguides can be interrogated). Constant offsets and/or slowly changing phase difference values might occur and be measured for one or both of the two counter-propagating directions, for example caused by environmental drift or the like. A steady state offset can be subtracted away and ignored, and a change in phase relationship that has a lower rate of change than the phase variation produced by the disturbance, can likewise be subtracted away in much the same way as an offset.

If a disturbance occurs somewhere along the length of the optical waveguide in detection zone 200, the time required to propagate to the two detectors or sensors 110, 111 in the counter propagating directions varies with the relative distances over which the respective counter-propagating beams propagate on, beyond the disturbance, to their respective phase detection sensors. This time difference can be measured by comparing the time varying angular change of the output polarization for the two counter propagating optical channels. The difference in propagation time thus can be measured. Knowing the velocity of light in the optical waveguide, it is a straightforward calculation from the time difference to the location of the disturbance along the waveguide in detection zone 200.

Figure 4:
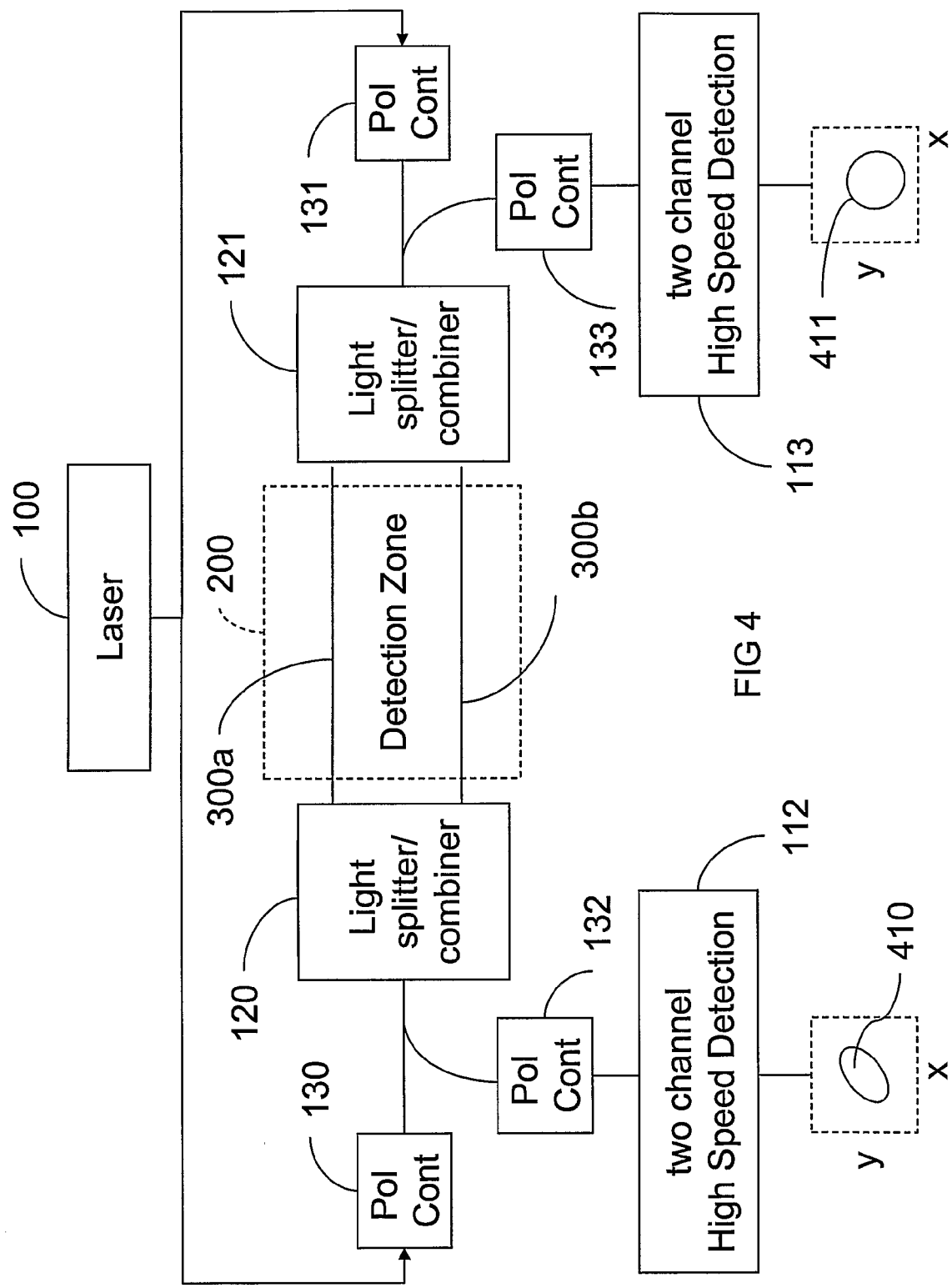
FIG. 4 is a block diagram of another arrangement of the distributed fiber sensor using polarization dependent phase responsive receiver, where the polarization receiver measures partial polarization information.

FIG. 4 is a block diagram, again using the same labels and reference numbers for elements already discussed, demonstrating certain alternative embodiments. Although the polarization response of the system can be detected by a polarimeter that is capable of measuring complete polarization properties (e.g., a full set of Stokes variables), a limited polarization sensitive detector is also possible. In FIG. 4, a detection system comprises two multiple channel high-speed detectors as the polarization sensors 112, 113.

In the following, two examples are discussed in detail to illustrate the principles of the inventive polarization based phase responsive receiver.

Example 1.1

Polarization Insensitive Beam Combiner

In this first example, light from the same source is launched into two fibers using a polarization insensitive light splitter. The output light is combined, using a polarization insensitive beam combiner. The combined output light is analyzed using a polarization measurement system (such as a high speed version of PS2300B polarization analyzer available from Optellios, Inc., Langhorne, Pa.) or using another polarization sensitive detector or detection scheme. A detected change of polarization provides information relating to the phase difference between the light signals that travel along the two signal paths for each of the opposite signal directions.

This approach does not require a particular state of polarization for light signals launched into the fiber(s). Nor is it necessary that the fiber have a particular amount of birefringence. The measurement generally is not influenced by different starting conditions (polarization states and birefringence conditions) or by long term changes that may occur such as changes in temperature. These effects can be ignored and/or distinguished from the short term changes that result from disturbances to be detected. As a result, this dual fiber system can be operated effectively in a bidirectional configuration in conjunction with a high-speed polarization analyzer or other polarization sensitive detection scheme, as a location resolving intrusion detection system.

For illustration purposes, a fiber optic coupler, preferably with an equal intensity-splitting ratio, is used as a non-limiting example in this part of the discussion. The input light signal is separated into at least two light beams with equal intensities. These beams, after traveling through the detection zone, are recombined with one another, using a polarization insensitive coupler. The intensity as well as the state of polarization of the resulting combined output light signal are affected by the phase relationship. However, the intensity response, as discussed previously, cannot produce substantially the same intensity-versus-time signature for both counter-propagating signals where there are differences in various polarization induced effects for the two propagating directions. Such a combined intensity response is only useful when a polarization controller is actively used to balance the polarization induced effects for both directions.

The time variation of the output polarization for the combined counter-propagating beams, characterized as the angular rotation of a phase trajectory on the Poincaré Sphere as described above, on the other hand, always has substantially the same shape for both counter-propagating beams. This occurs because the phase trajectory is a more direct representation of the changing phase difference caused by the disturbance, and the phase difference is substantially identical for both counter-propagating directions.

The phase difference of the combining beams can be calculated from the angular difference between consecutive plotted (or otherwise encoded) points on un-normalized polarization trajectory as projected onto a circular shape. Because the phase effects are substantially identical for both counter-propagating directions, the location can be determined from the resulting two phase responses for the two counter-propagating signals, measured by corresponding angular changes in the positions of points plotted (or otherwise encoded) for both counter-propagating directions.

The size and shape of the polarization trajectory represented by the Stokes parameters changes as a result of changes in the polarization relationship between the combining beams. According to the invention, however, the polarization trajectory can be processed to project the points onto a circle of a normalized unit diameter, and from which the angular position of each sampled set of data points is derived.

The resulting trajectory can become eccentric or small in diameter. It is possible to project a small or eccentric trajectory onto a unit circle. The accuracy in the measurement of the rotation angle of the sample points in most conditions is sufficient to enable correlation of the time signatures of the disturbance, namely to identify the effect of the disturbance as comparable changes in rotation angle versus time, for the two counter-propagating signal paths. Specific conditions can arise when the trajectory becomes so small or highly eccentric as to preclude a positive determination of the rotation angles of the sample points.

For example, if the diameter of a trajectory is made small, the resolution used in digitizing the position of a sample on the trajectory may become large relative to the size of the trajectory. If the small trajectory then is projected onto a larger diameter circle, the digitizing error is correspondingly larger. Similarly, as the eccentricity of a trajectory also affects the measurement accuracy. For example, the situation can arise that the beams become wholly parallel polarized, reducing the trajectory trace to a straight line.

It is relatively rare for polarization relationships in the real world to become or to remain so fully parallel or orthogonal as to preclude effective operation of the system as described herein. Nevertheless, the situation can be avoided by providing controls that are enabled to adjust the polarization relationships using one or more polarization controllers 130 and 131, shown in FIG. 3, when the trajectory size or eccentricity become extreme. All that is necessary is to displace the polarization relationships away from these specific states.

Because the beams are combined in a polarization insensitive manner, the polarization controller(s) can be placed outside the waveguide to adjust the relative relationship between the polarizations of the interfering beams.

The only situation wherein a polarization controller might be advantageous inside the waveguide is when the two light paths have substantially equal polarization transformation functions. That situation is unlikely for any practical system. Another method to avoid a small trajectory situation is to provide a control to tune the wavelength. As described previously, the polarization transformation is wavelength dependent. By adjusting the wavelength of the light beam, the relative polarization relationship can be adjusted. A wavelength adjustment or a displacement using the polarization controller(s) can be triggered by an output from a processor (not shown in FIG. 3) that processes the data from the phase receivers, in this case from polarization sensors 403, 404.

FIG. 4 demonstrates an arrangement with polarization controls 130, 131 in the signal insertion paths leading from source 100 into the splitter/combiners 120, 121. Also, polarization controls 132, 133 are provided from the combined beam outputs from splitter/combiners 120, 121, leading into the phase detectors that in this case comprise two-channel high speed polarization state detection units 112, 113. The detection units 112, 113 derive two phase related variables that are schematically shown in FIG. 4 as more or less eccentric plots of trajectories 410, 411 along which sample points fall. When projected onto a circle (not shown in FIG. 4), the sample points define rotation angles as described.

Figure 5:
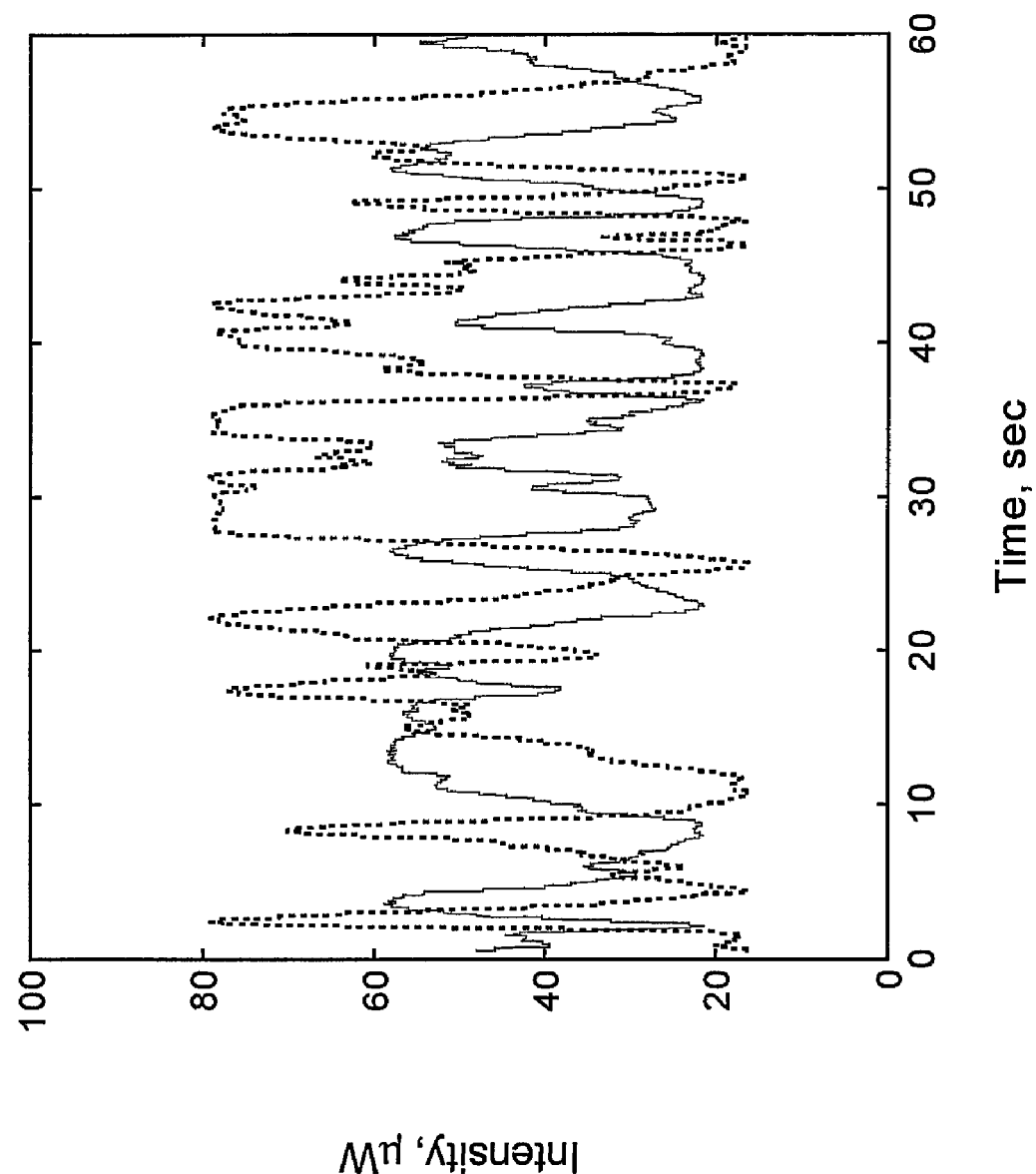
FIG. 5 is a long timescale plot of typical interference intensity traces comparing interference intensity variations for two counter-propagating directions, demonstrating relatively low signal correlation.

Experiments were conducted and data collected to test and demonstrate the concepts discussed above. FIG. 5 is a typical measurement of intensity traces versus time for the two channels. The two intensity traces shown are the intensities of the opposite combined pairs of signals for the two counter-propagating paths. Because of various polarization effects, the intensity responses have quite different time varying shapes as shown in this plot over a time scale of one minute.

FIG. 6 is a three dimensional isometric view showing corresponding non-normalized Stokes parameters trajectories. The trajectories each appear to represent the intersection of a plane and sphere. The sizes and orientations of the trajectories are different. However, repetitive samples of polarization parameters, taken over a time scale during which the intensity values may irregularly as shown in FIG. 5, are found to fall on these highly regular trajectory paths. An aspect of the invention is to regard these and similarly derived trajectories as projected phase relationship plots demonstrating a phase variation. The angular position of a sample on said trajectories demonstrates a phase difference between the two combining beams. A change in phase difference can be derived and calculated over time, providing a phase variation signature.

The phase variation time signatures derived by determining the relative angular positions of points on these trajectories, are substantially independent of polarization influences. Changes in polarization states may increase or decrease the size of the trajectory and may change the orientation at which the trajectory plane intersects a sphere defined by the unnormalized Stokes parameter values. However, the time varying phase relationships of points on these trajectories have been found to correlate closely.

Figure 7:
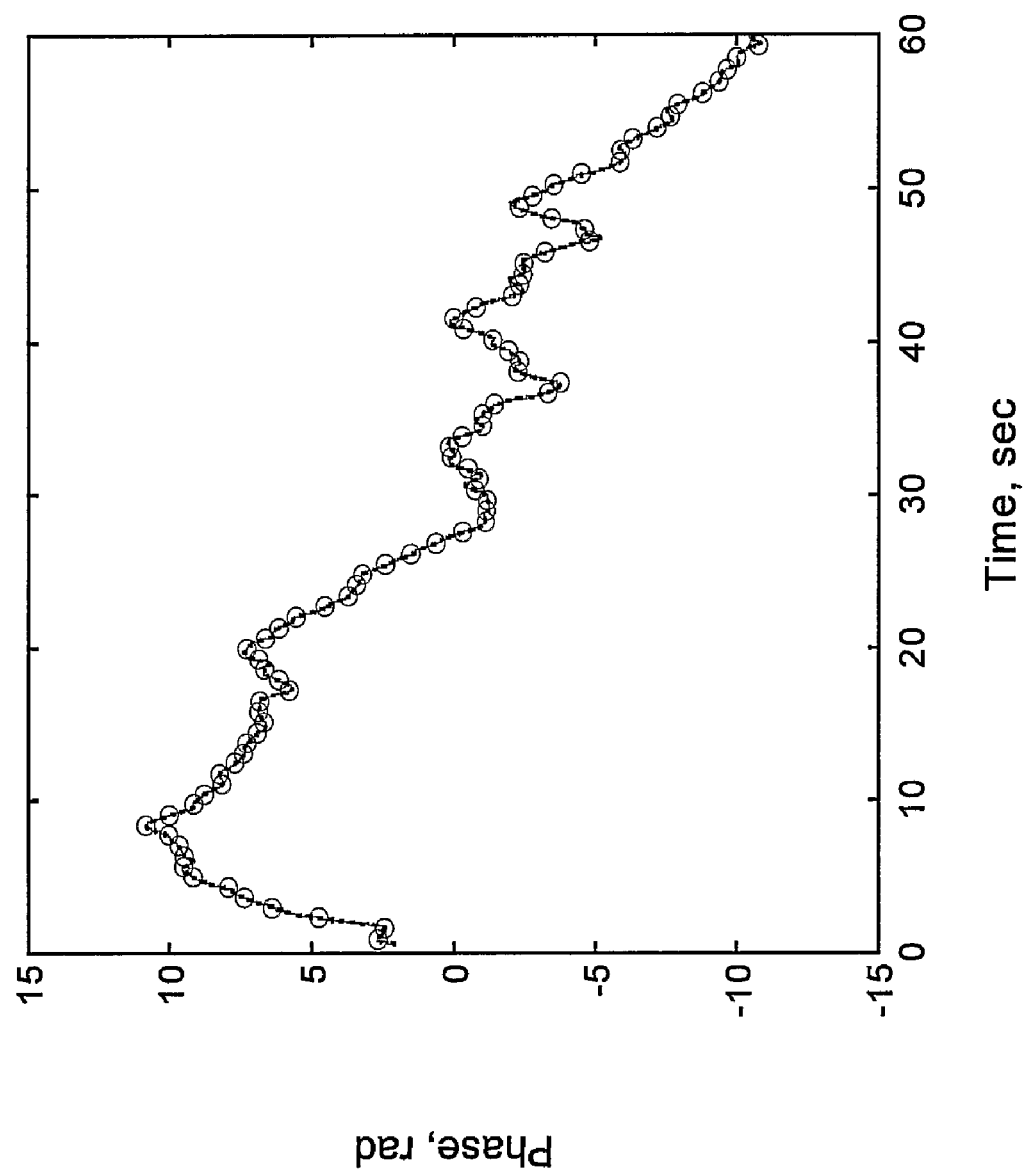
FIG. 7 is a time plot of typical phase traces calculated from the Stokes parameter trajectories in FIG. 6, for each propagating direction. One trace is shown as a solid line, the other marked by open circles. These traces demonstrate the high degree of correlation available according to the inventive concept of discriminating specifically for phase.

FIG. 7 is a dual plot showing the time varying phase relationships for two counter-propagating signal directions, determined from angular positions around trajectories as shown in FIG. 6, and at the same time scale as shown in the dual plot of intensity traces of FIG. 5. The very substantial correlation in the time varying signal shapes as shown in FIG. 7 enables the two signals to be used for various comparison techniques. These comparison techniques lend themselves readily to determining a lead or lag time of propagation of a phase variation caused by a local disturbance in the detection zone, to the appearance of corresponding variations at the phase receivers for the counter-propagating signal directions. The location of the disturbance can be resolved from the time difference.

Example 1.2

Polarization Sensitive Beam Combiner

In this second example, light from the same source is launched into two fibers using a polarization beam splitter, thereby creating two beams. The signal from the same light source can be used to create both counter-propagating beams. The light beams pass through the detection zone and are then combined, using a polarization beam combiner so as to analyze the orthogonal components of the beams in the two fibers. The combined signal is analyzed using a polarimeter or other polarization sensitive detection scheme. The change of polarization provides the information about the phase difference between the beams that travel along the two paths.

A schematic example demonstrating phase detection based on polarization change is shown in FIG. 8. Light is injected into two paths 300a and 300b by operation of a beam splitter 122 (element A). In the illustrated example, the beam splitter is a polarization beam splitter. Both beams are recombined using through a polarization beam combiner 123 (element B). If the polarization states for these two beams vary slowly, the intensity of the combined beam output from the polarization beam combiner 123 remains substantially constant over the time scale of interest. The state of polarization (SOP) of the output beam, on the other hand, can vary with the phase difference between the two beams. The output SOP varies as a function of the phase difference $\Delta\phi$ of the two beams as follows:

$$\vec{E} = E_{10}\hat{x} + E_{20} \cdot e^{\Delta\phi}\hat{y}$$

FIG. 9 illustrates another configuration for detection using polarization change. In this embodiment, the polarization beam splitter/combiner is replaced by a polarization displacer, for example comprising a birefringent crystal cut to the required dimensions. The birefringent crystal retards a polarization component that is parallel to one axis the crystal relative to the other axis.

These arrangements of FIGS. 8 and 9 each segregate and recombine polarization components as separate beams. A change in the relative phase difference $\Delta\phi$ between the beams corresponds to a change in the polarization state of the combined beam, which state is determined by the presence and relative power levels of such polarization components. In a case where the relative phase difference between the two signals along different paths in either FIG. 8 or FIG. 9 should change, and assuming that the intensities of the two polarization components for the two beams are equal, then the trajectory of the polarization evolution between plotted (or otherwise encoded) points will be an arc of a great circle on the Poincaré Sphere, representing the polarization state before and after the change in phase (and change in polarization state). The angular change of that polarization evolution, measured with respect to the center of the circular trajectory, is directly related to the phase difference between the two combining beams along different paths.

If the power is unequal for the two beams and the phase relationship changes, then the evolution is a circular arc trace on the Poincaré Sphere that represents a phase difference, but the size of the circular trajectory can vary. Nevertheless, the angular change of between the starting and ending polarization states plotted (or otherwise encoded) in this way, measured with respect to the center of the circle, is still equal to the changed phase difference between the two signals along different paths. The angular measurement of phase difference remains resolvable whether the circular trajectory is larger or smaller. Thus it can be seen that by determining and using the rotation angle around the trajectory, changes in phase angle can be discerned in a way that are free of certain complications associated with polarization.

Figure 11:
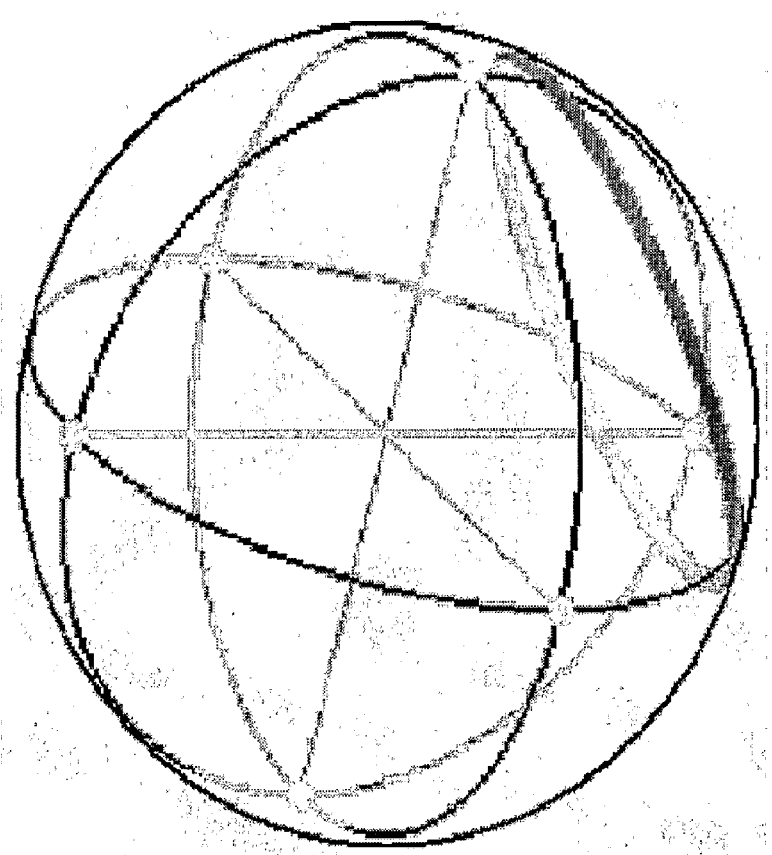
FIGS. 10 and 11 compare two circular trajectories on a Poincaré Sphere demonstrating an output state of polarization (SOP) evolution when combining orthogonal polarization components.
Figure 10:
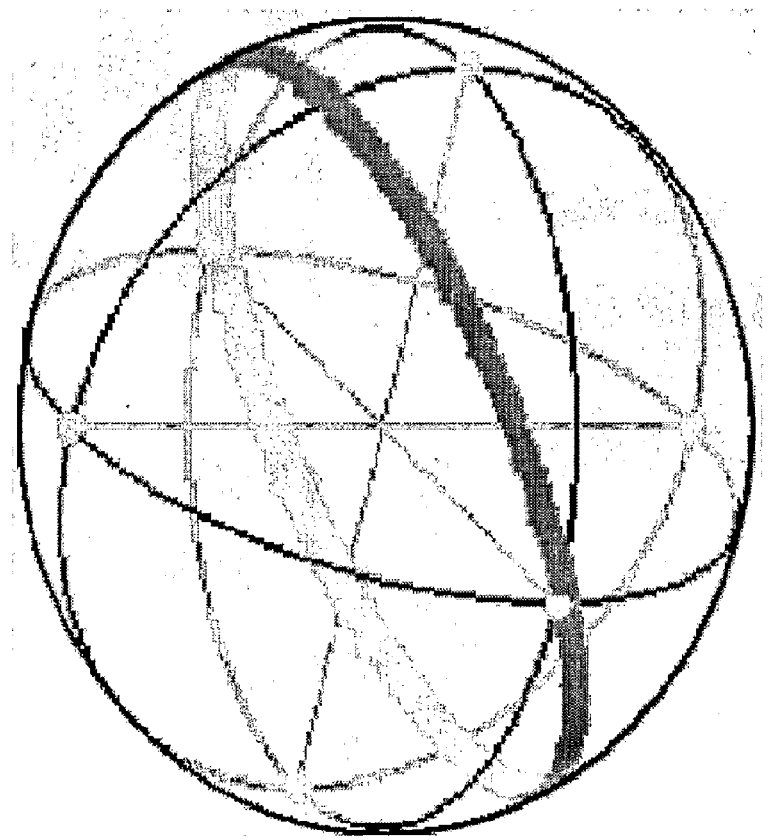

Experimental tests were conducted using the polarization sensitive beam separator and combiner shown in FIG. 9. The two paths 300a, and 300b were composed of single-mode optical fibers. The outputs of the combined beam for the two counter-propagating signals were analyzed using Optellios' PS2300B polarization analyzers. FIG. 10 shows an experimentally obtained circular SOP trajectory that resulted from the varying phase difference of two signals carried on different paths in one of two counter-propagating directions and FIG. 11 shows the SOP trajectory in the opposite direction. The variations in state of polarization (SOP) as shown were due to ambient phase fluctuations between the two fibers, 300a, and 300b.

It can be seen in the oblique isometric projections in FIGS. 10 and 11 that the SOP trajectories are circles on the Poincaré Sphere. According to an inventive aspect, the trajectory circles are used as a phase attribute of polarization state.

The location, size and orientation of the trajectory circles are different in FIGS. 10 and 11. At any given time, the positions of respective samples for the counter-propagating directions, plotted (or otherwise encoded) as points on either of the two trajectory circles, are different points on the Poincaré Sphere. It has been found, however, that the successive differences in phase angle as represented by the rotation angle around the depicted circles, is a measure of phase relationship that is reflected in the progress of samples for both counter-propagating directions.

In an embodiment as described with reference to polarization state, the phase relationship concerns the relative phase relationship of orthogonal polarization components in each of the counter-propagating directions, that relative phase relationship being reflected in the plotted (or otherwise encoded) polarization state on the Poincaré Sphere.

As visually shown by the trajectories in FIGS. 10 and 11, successively plotted points provide a way to determine relative phase differences from one sample to the next, as shown by angular rotation between that points at which the successively plotted (or otherwise encoded) samples fall on the trajectories. Although two opposite signal paths plot to different trajectories, for example when a power imbalance exists between the two channels (e.g., comparing the two traces in FIGS. 10 and 11), this technique can be employed to measure phase time changing phase relationships and to provide a signature of phase variation over time. The power imbalance and other particulars of the polarization state do not prevent the trajectories from plotting to circles from which angular position data can be derived, in particular changes in rotation angle versus time for successive samples, representing the changing phase relationship.

An optical fiber typically has some birefringence that differentially retards one polarization component relative to another. This alters the SOP of the light propagating in a fiber from an input to an output. The alteration is different in opposite directions. Differential retardation through a fiber results in some power loss at the polarization combiner 125. However, power fluctuations do not alter the angular difference in plotted (or otherwise encoded) positions around the polarization trajectory in FIGS. 10 and 11 when the polarization state changes. The parameter of interest, namely the angle at which a point plots around the trajectory circle, is not sensitive to power level.

Assuming that a SOP fluctuation causes an intensity mismatch, the trajectory circle is possibly moved on the Poincaré Sphere (e.g., compare the two examples in FIGS. 10 and 11), and it is possibly changed in size, but the phase difference of the two beams can still be measured using the changing SOP trajectory circle rotation angle as the operative parameter.

Although intensity fluctuation does not prevent measurement of an angle around a trajectory as a representation of phase, the same practical consideration discussed with respect to the previous embodiments apply to favor keeping the intensities equal if possible. If the intensities are equal, the trajectory has the full great circle diameter of the Poincaré Sphere. In other cases, the circular trajectory of the rotation of the SOP can be displaced (e.g., the trajectory in FIG. 11 is displaced downward compared to the example shown in FIG. 10). In an extreme case, the diameter of the trajectory on the Poincaré Sphere is reduced to an impractically small dimension. The situation can be avoided, and if desired the system can be optimized to maintain a power balance, by providing polarization controllers to adjust the beam polarization conditions when needed, or by triggering a controller operable to tune the operating wavelength of the laser or other light source.

If no light should be received along the path to the detector for one of the two paths, as illustrated schematically in FIG. 12, a phase difference measurement between the two beams obviously cannot be obtained. There may be some light along both paths, but if the transfer functions between the input SOP and one of the two outputs is such that the beams are not combined, then the rotation of SOP cannot be detected and the phase difference cannot be obtained. A way to avoid or correct for this situation, if necessary, is to provide one or more polarization controllers at some point in the path, so that the polarization of one or both of the two beams is altered to avoid the situation discussed above wherein one beam is effectively blocked. Another preferred technique is to tune the launch wavelength so as to alter the state of polarization of the light propagating through the fibers and in effect to control the power distribution in the two beams at the polarization combiner, which has a similar effect of opening two signal paths from which a phase measurement is possible. The polarization transformation is wavelength dependent. Especially for a long fiber, changing the wavelength will alter the propagation conditions sufficiently to relieve the special situation described above in most instances.

Figure 13:
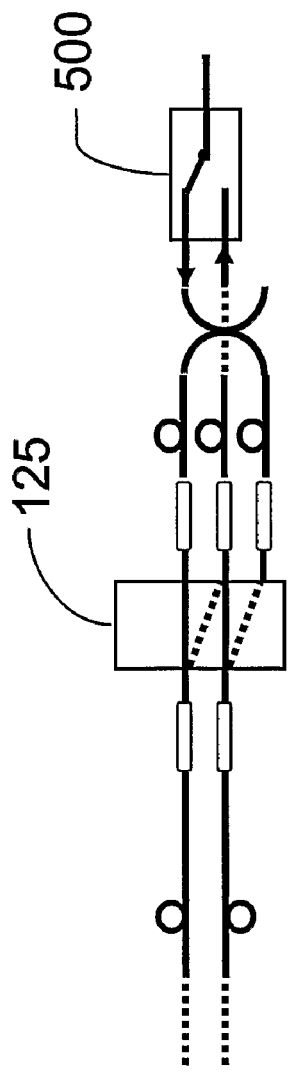
FIG. 13 schematically shows a switching configuration for phase detection using polarization.

Still another technique to avoid the problem is to use a switching configuration, for example as shown in FIG. 13, wherein a power mismatch in the two arms can be properly managed by using a 1×2 optical switch 500. In this configuration either of the two switch-selectable output ports can be used for monitoring the phase difference between the two detection signal paths. At any given time one or the other port can be selected using the switch 500. Switching from monitoring one port to the other can be triggered as a function of the detected size of the polarization circle trajectory on the Poincaré Sphere, using a control function of a programmed processor (not shown in FIG. 13) to toggle switch 500 if the polarization trajectory size should be reduced to some threshold minimum, thus establishing different polarization trajectory conditions.

Figure 14:
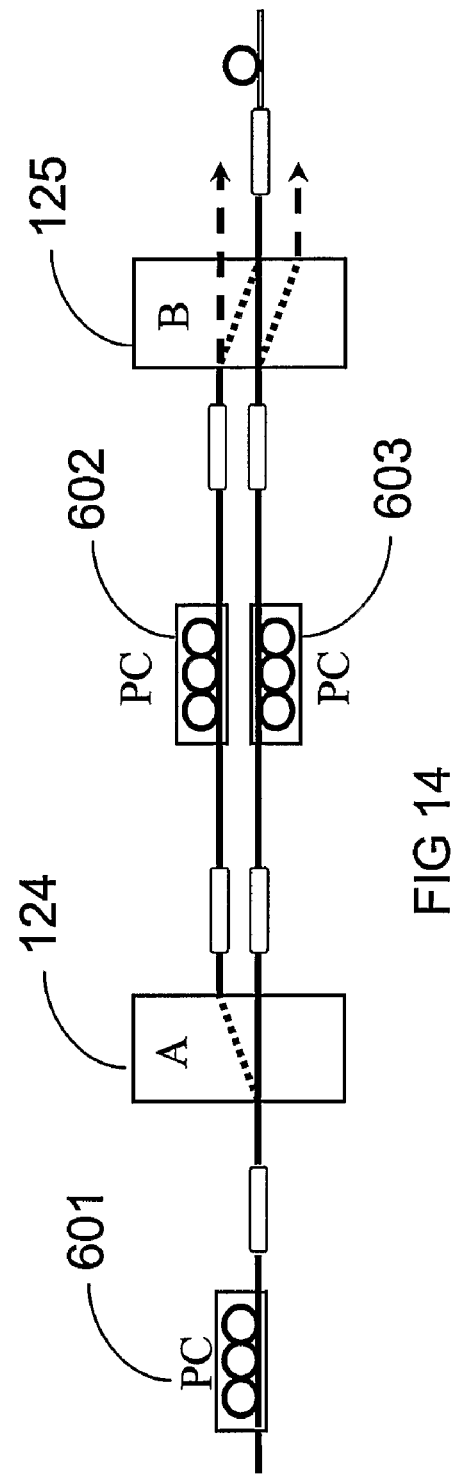
FIG. 14 schematically shows polarization based phase measurement including polarization controllers.

If a polarization controller is used in the system, there are several choices of configuration and operation. Some are now discussed. As shown in FIG. 14, a polarization controller 601 can precede a polarization splitter 124 to control the incident SOP. A polarization controller 602 and/or 603 can be placed between the polarization splitter 124 and a polarization combiner 125. Also the polarization splitter can be replaced by a polarization insensitive coupler, so as to provide for substantially equal intensity along the two paths.

In this discussion, a number of examples are detailed for handling two beams or two signals along different paths, the phase relationship of which is to be established and monitored over time. The invention relates to phase relationship measurements as such, and also to the advantageous use of such phase responsive measurement techniques in counter-propagating signal paths where paired-beam signal paths are established in opposite counter-propagating directions, and the phase measurements taken for both directions are correlated to resolve a lead/lag time accounting for the location of the disturbance that produces a signature variation of phase versus time.

According to another inventive aspect, phase effects can also be collected and analyzed with only a limited set of polarization related properties obtained using two polarization sensitive detectors, which will be described in more detail below.

By measuring the time difference between the two counter propagating directions using polarization measurements as described before, the location of an intrusion can be resolved by equating the observed time delay with a difference in propagation time between the location of the intrusion (or other disturbance) and the detectors. In the arrangement shown in FIG. 15, there is no need to adjust the SOP such that the relative SOPs relationship of the two beams are matched before the point at which two beams combine to produce an interference intensity for the two counter-propagating signals. As a result, the method and apparatus of the invention are more robust and less sensitive to system fluctuations.

In one embodiment, polarimeters are used to measure the state of polarization and to collect trajectories from the values of successive samples, being coupled to a data processor or the like to resolve and to correlate the changing phase difference between the two beams in each counter-propagating direction so as to determine the location of a disturbance. A simple detection arrangement is possible wherein less-complete polarization state related information will suffice.

An inventive aspect is to provide a circularly projected transform of the polarization evolution, for example as represented graphically (or otherwise) by a two dimensional projection of trajectory points on a Poincaré Sphere, in a direction whereby the result is a circle. The projection is two dimensional (i.e., on a plane if considered graphically). The projection can employ a set of two dimensional data points that form an eccentric (elliptical) pattern, but that pattern is normalized as a circular trace centered at an origin.

For example, the SOP of the output signal can be a great circle in the S1-S2 plane (i.e., S3=0). The angular change of the SOP can be calculated using the outputs of two detectors, the sampled values from which are independent variables that together define a point in a two dimensional space. FIG. 16 shows an embodiment in which detectors A and B are preceded by polarizers 801 and 802, oriented, for example, at 0° and 45°, respectively. In FIG. 16, the output signal is separated into two equal intensity paths by a polarization insensitive beam splitter 701. The first path passes through a 0° polarizer 801, before it is applied to an intensity or amplitude detector A. The second path passes through a 45° polarizer 802, before it is applied to detector B. This arrangement provides two intensity data channels.

The relation between these two intensity channels is such that as the input light signal changes in polarization state, the intensity responses vary. The power distribution between the two channels shifts. If the polarization characteristics vary over time through a full phase transition or period (i.e., $2\pi$), the intensity distribution shifts full cycle back to its original condition. The successively sampled data values fall at various points in a closed trajectory pattern. As the polarization state of the light signal varies, the changing intensity data points plot to points on an elliptical shape in two dimensions.

The shape of the SOP trace projection as thus obtained may be elliptical but it is possible accurately to determine a phase angle even though the trace is elliptical rather than circular. This generally amounts to re-mapping the elliptical pattern of the trajectory as a projected circle with an origin, whereupon an angle can be determined by the sine and cosine relationships of the X and Y coordinate values on the projected circle. The aspect ratio of the trajectory plot is corrected to render the trajectory circular.

In this disclosure, the graphic nature of the Poincaré Sphere, the elliptical shape of certain trajectory trace patterns obtained from samples of two independent variables and other aspects are discussed and explained with respect to graphic plots and patterns, i.e., the appearance of a graph that might be obtained if the data values were plotted (or otherwise encoded) in a coordinate system. It should be understood that such graphic explanations are to enable understanding. In an operational embodiment, there is no requirement for a graphic printout or display or the like. The point is simply that data points as represented by a set of values that may encompass a larger or smaller span and may be eccentric rather than substantially circular, regardless of whether the values are ever plotted, encoded or displayed, are processed according to the invention to derive a rotation angle in a circularly periodic trigonometric representation of phase data.

The size of the trajectory is determined by the power relationship between the two components that are combined by the polarization sensitive combiner and used for output SOP detection. The size of the trajectory can be controlled by polarization controllers, some examples being shown in FIG. 14.

The polarization controllers 601, 602 and 603 of FIG. 14 can be used to control the size of the trajectory. Polarization controller 601 establishes a polarization state before the light reaches the polarization sensitive beam splitter 124. Polarization controllers 602 and 603 control the polarization before the polarization sensitive combiner 125. (FIG. 14 shows a one-direction signal path with two signal legs, but in location detection embodiments as otherwise explained herein, counter-propagating signal paths are used the can be, for example, two signal paths as in FIG. 14, oriented in opposite directions.)

In the proposed location detection system, the location of the event or disturbance is detected directly from the phase responses obtained in the counter-propagating signals, specifically by their lead/lag timing. In this case, variations in polarization state, as discussed above, only affect the trace size and the projected trace shape. The phase relationship between signals along different signal paths for each opposite signal directions, and ultimately the event location, are determined by sampling values that correspond to the angular displacement of the point along the circularly projected trace.

As long as the trace is not so small or so eccentric that the resolution error is untenable, the rotation angle can be determined, independently of specific polarization values. This technique produces a robust and dependable parameter, whereby sampled values representing the same phase change time signature appears clearly in both counter-propagating signal directions, can be readily correlated over a lead/lag time, and allows a location to be inferred for the disturbance that caused the phase change.

Some further examples are also explained herein. In FIG. 17, polarization controllers functionally similar to devices 602 and 603 in FIG. 14, are implemented by two patterned Liquid Crystal (LC) tunable waveplates. These waveplates can be directly attached to the polarization sensitive beam combiner as manufactured. The LC cell contains a patterned electrode, such that polarization controls can be applied independently to the upper arm and the lower arm (distinguished in FIG. 17 by shading). With two patterned waveplates, it is always possible to generate a SOP trajectory that is a great circle. Even without such capability, because the measurement is insensitive to the size of the trajectory (and as long as the trajectory is not too small), accurate measurement can be achieved. Therefore, one patterned LC cell oriented at 45 degrees also will suffice.

An example of a two-beam combination is shown in FIG. 18. Two beams are combined, passing through 0° and 90° polarizers 128a. Other combinations of the angles may also be used. In this case, the polarization state for the combined beam depends on the phase difference of these two beams. Multiple beams also can be combined using a polarization sensitive beam splitter. One such example is shown in FIG. 19, where four beams are combined, each passing through a polarizer oriented at a specific angle. For combining more than two beams, as shown in FIG. 20, the polarization aspect of the combined beam can be somewhat complicated.

Figure 21:
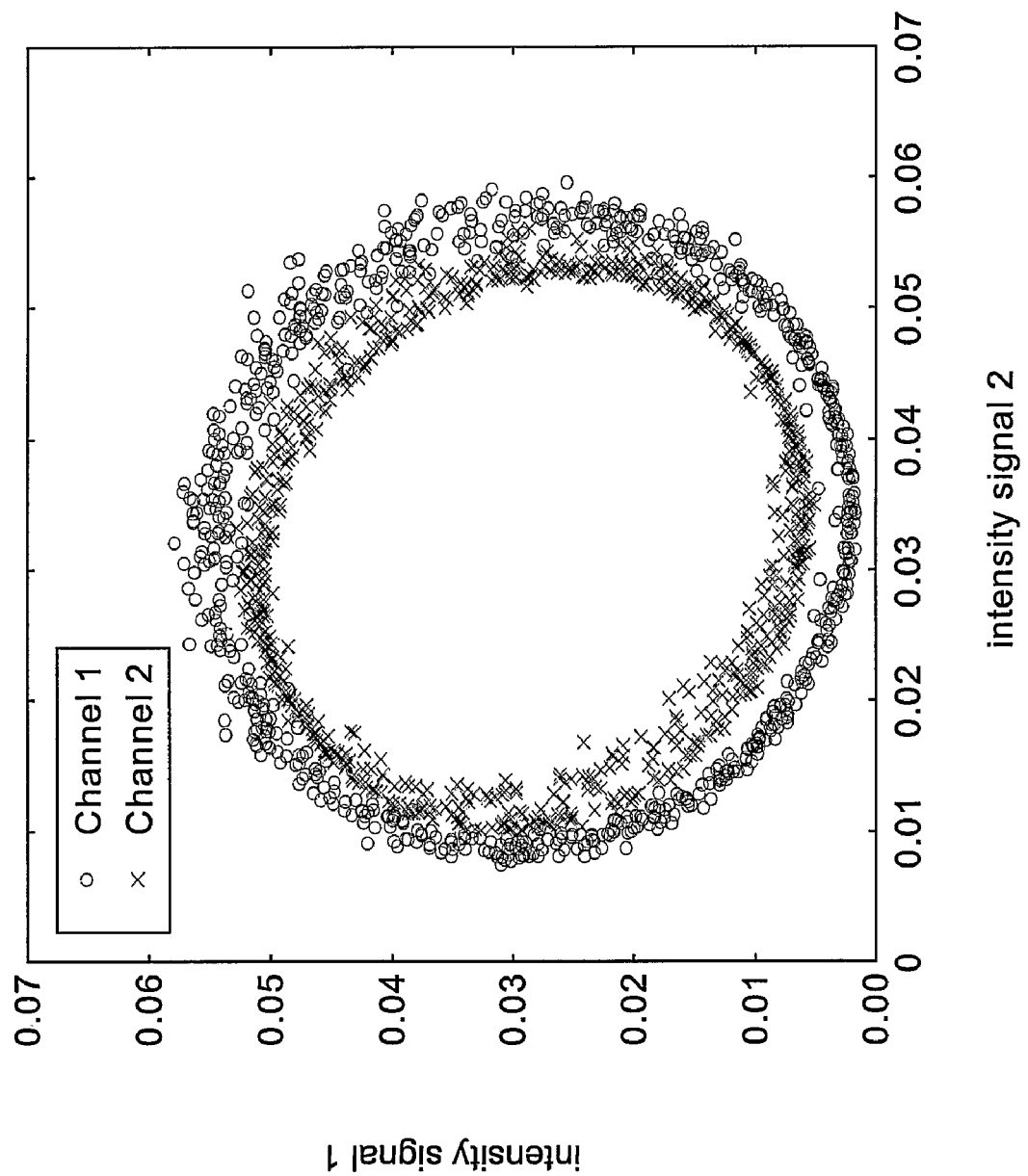
FIG. 21 is a two dimensional plot wherein the X and Y coordinate positions represent intensity values measured by sets of two polarization sensitive detectors according to the invention, one set being plotted (or otherwise encoded) for each propagating direction (Channels 1 and 2) and showing a population of many paired data samples.

Experiments were conducted to test and demonstrate these concepts. FIG. 21 is a plot of typical intensity measurements, wherein two detector values were obtained as independent variable values as described, namely by repetitive sampling of two detectors for each of two counter-propagating signal channels. The detector sample values are plotted in FIG. 21 on vertical and horizontal Cartesian coordinate plots, using X and O characters for the respective counter-propagating directions, each such character representing two contemporaneously sampled detector values in one of said directions. Sampling continued over a sufficient time to ensure phase changes that may exceed full $2\pi$ period. By comparing the change in angular positions from one sample point to the next, in repetitive samples of the two intensities of each of the two channels, the phase relationship of component beams can be determined over time.

Figure 22:
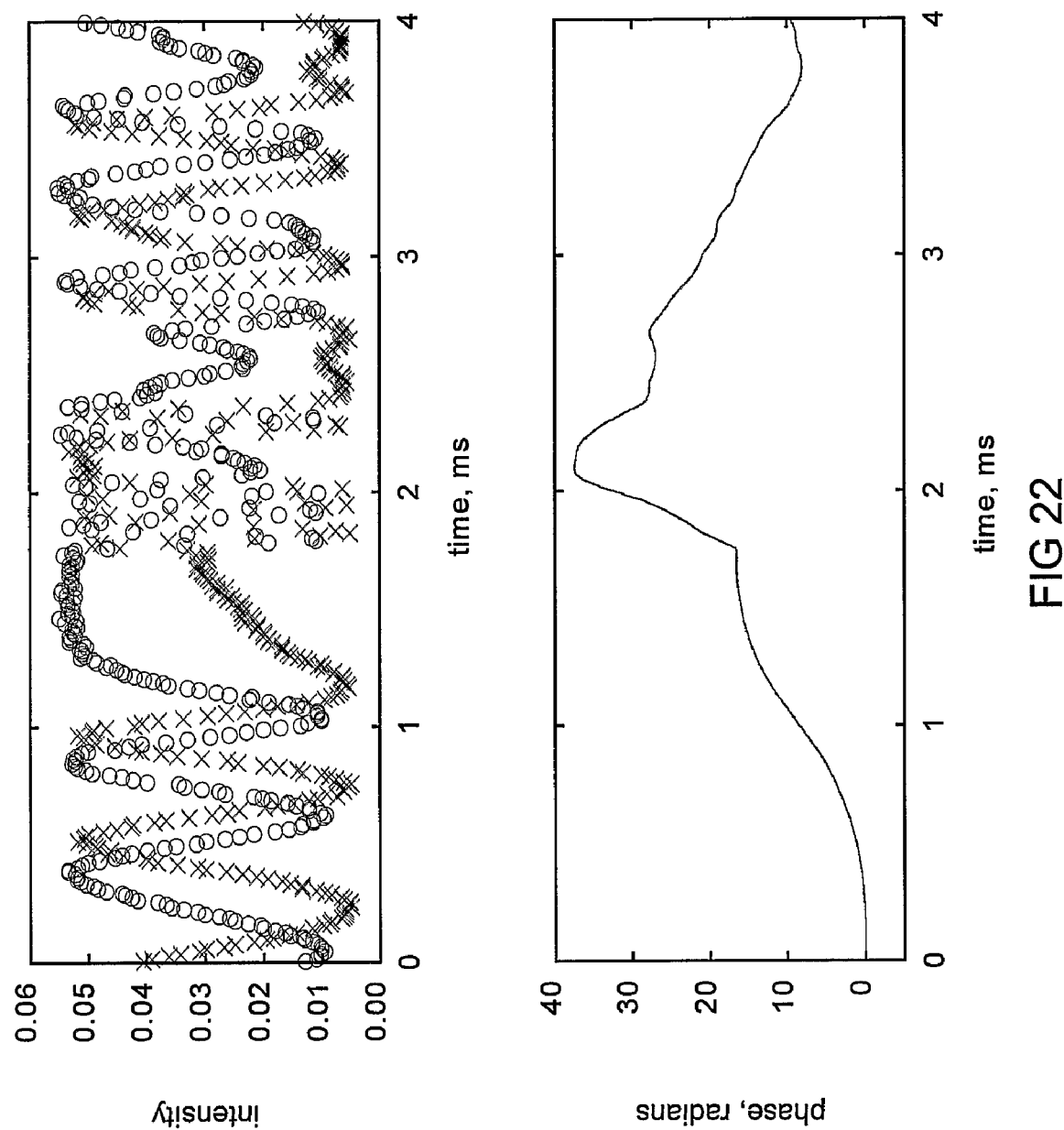
FIG. 22 is a time plot comparing a plot of two intensities for the same propagation direction versus time and the corresponding relative phase difference versus time, calculated from the intensities. The intensity as plotted is bounded. The phase is unbounded.

Corresponding intensity values for two detectors and the corresponding accumulating change in angular phase position are plotted (or otherwise encoded) over a short time scale in FIG. 22. As discussed, an object of an intrusion detection system or other system in which the location of a disturbance is to be calculated, is to correlate the time signature of corresponding responses in the counter-propagating beams. Specifically, the time changing phase relationship of plural beams is to be determined and correlated in counter-propagating beam pairs. Although the upper and lower plots in FIG. 22 represent the same phase change, the processed phase angle data is a cleaner and potentially more useful representation.

Figure 23:
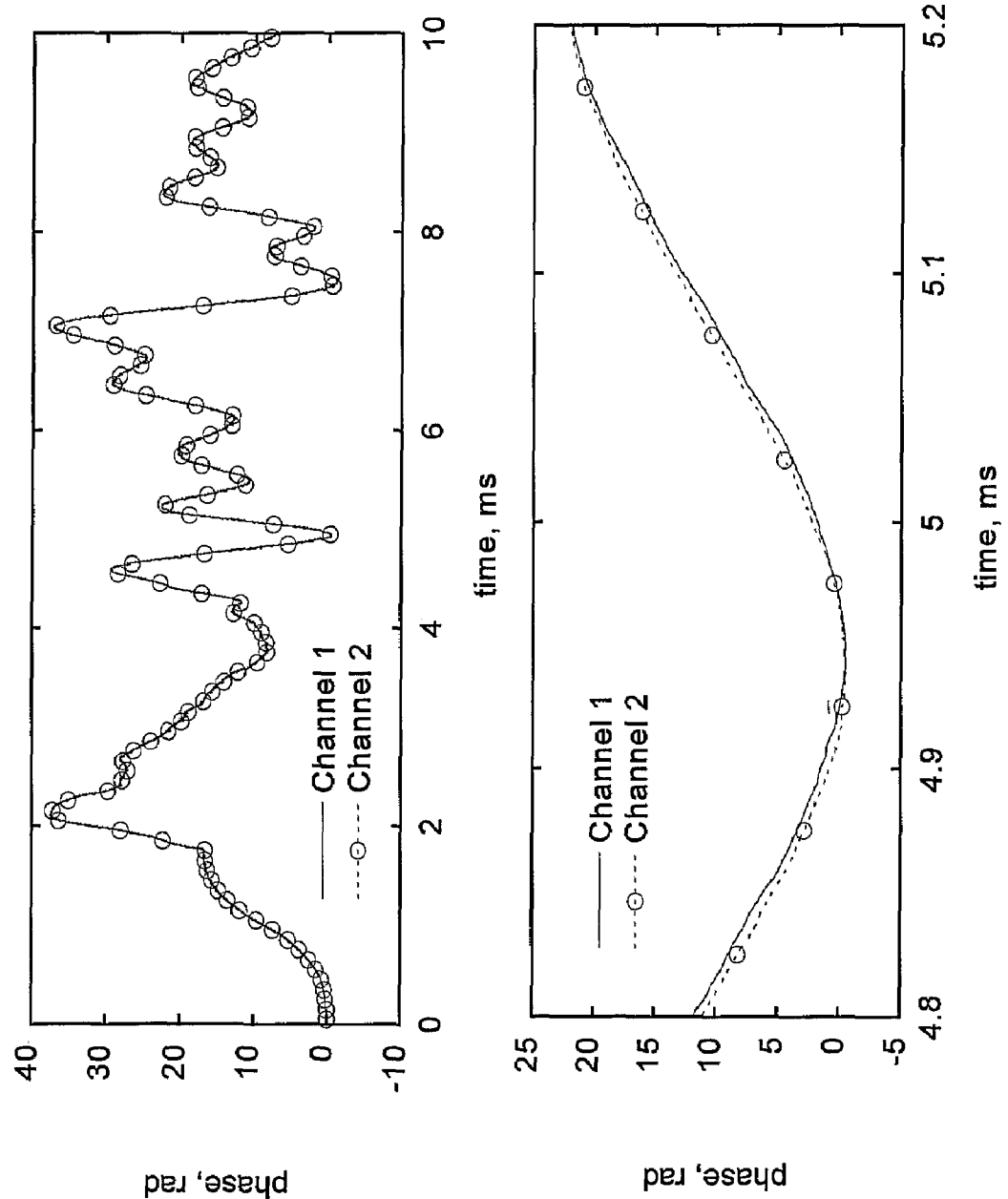
FIG. 23 is a pair of time plots comparing phase response signatures for two counter-propagating beams and showing the extent of divergence of such signatures over longer and shorter time scales.
Figure 24:
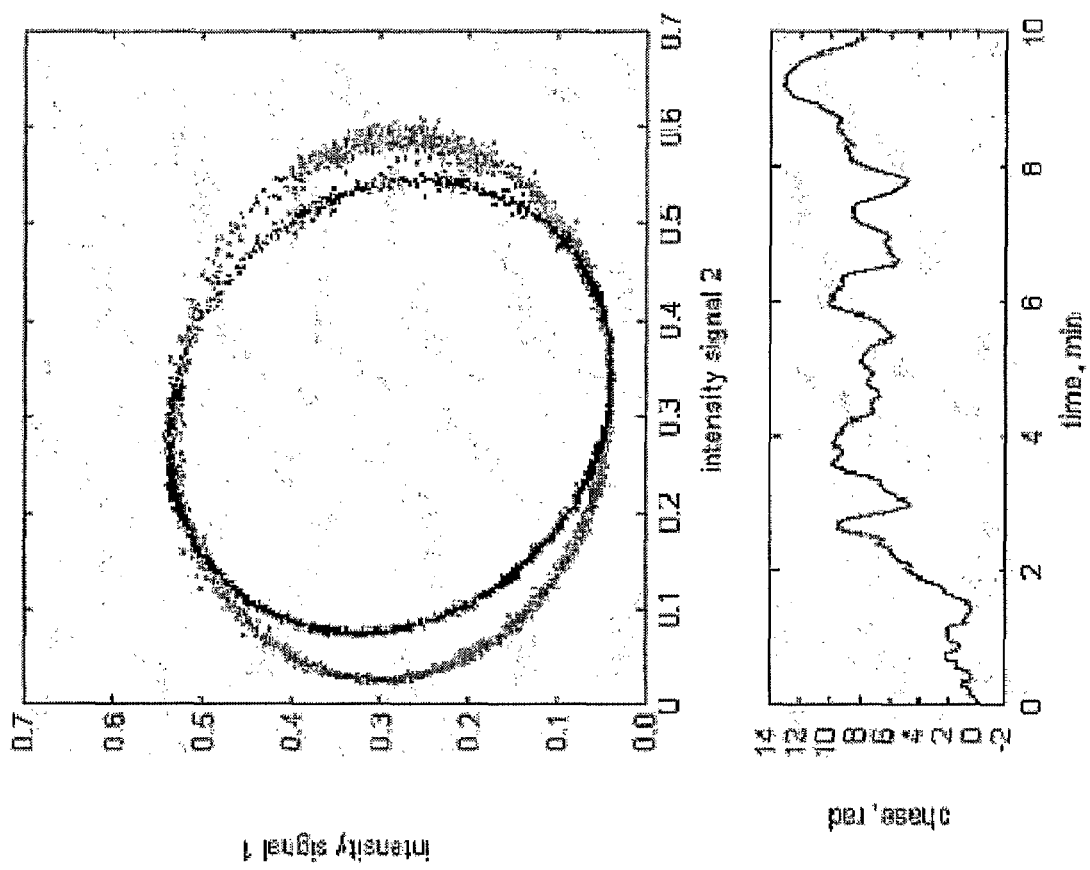
FIGS. 24($a$) through 24($e$) are sets of plotted channel intensity traces as in FIG. 21, together with time-phase plots, showing experimental results of detected signal values in the absence of disturbance, for polarization state trajectories having different circle sizes on a Poincaré Sphere, and demonstrating the effect of evolution of the trajectory to progressively smaller diameters down to a spot.
Figure 24:
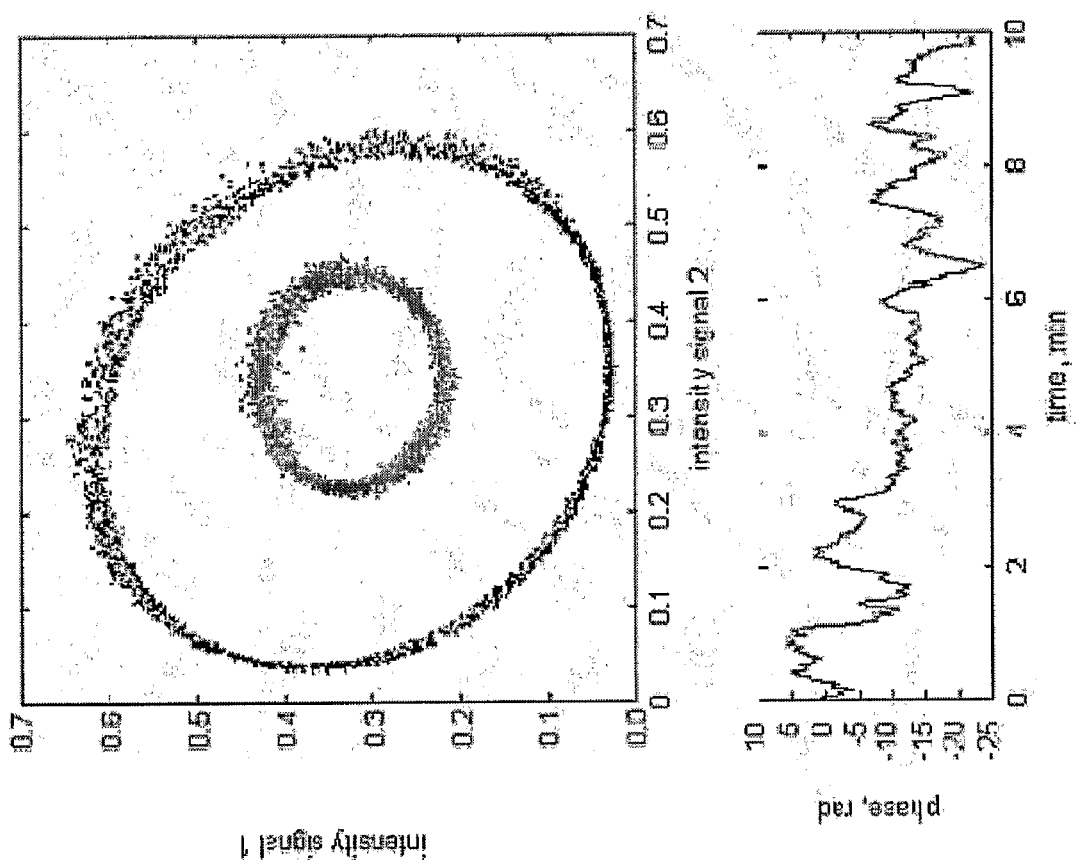
Figure 24:
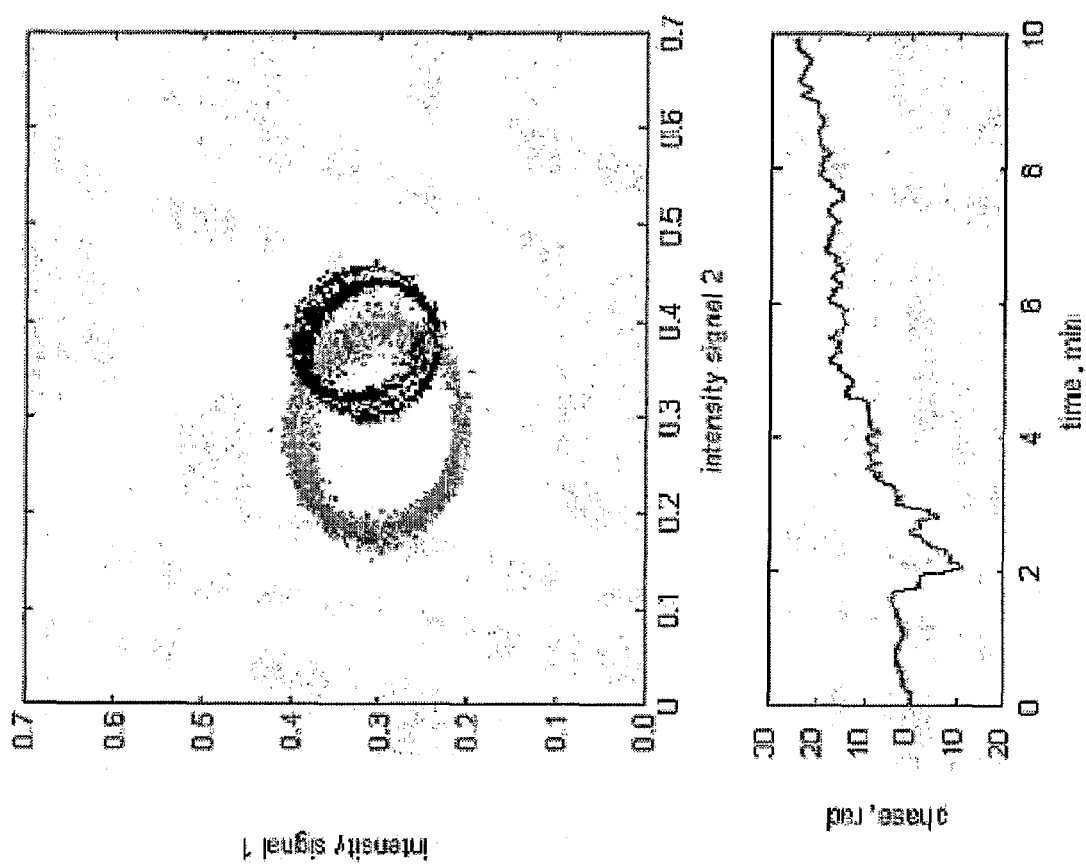
Figure 24:
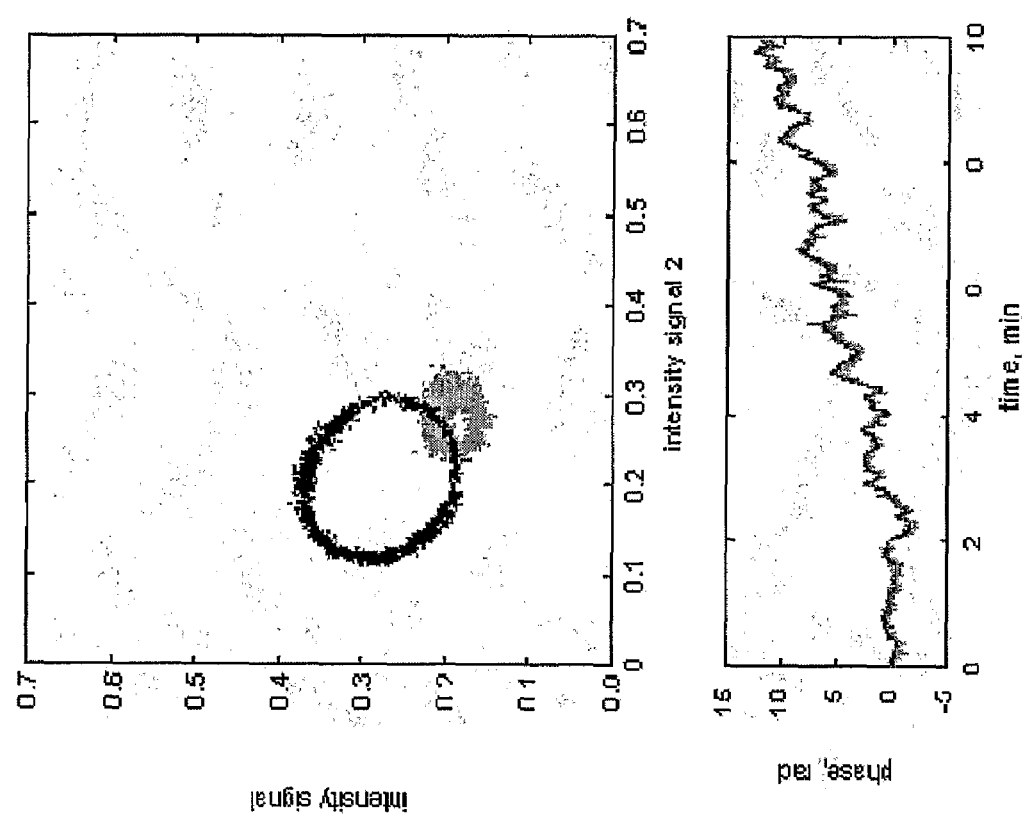
Figure 24:
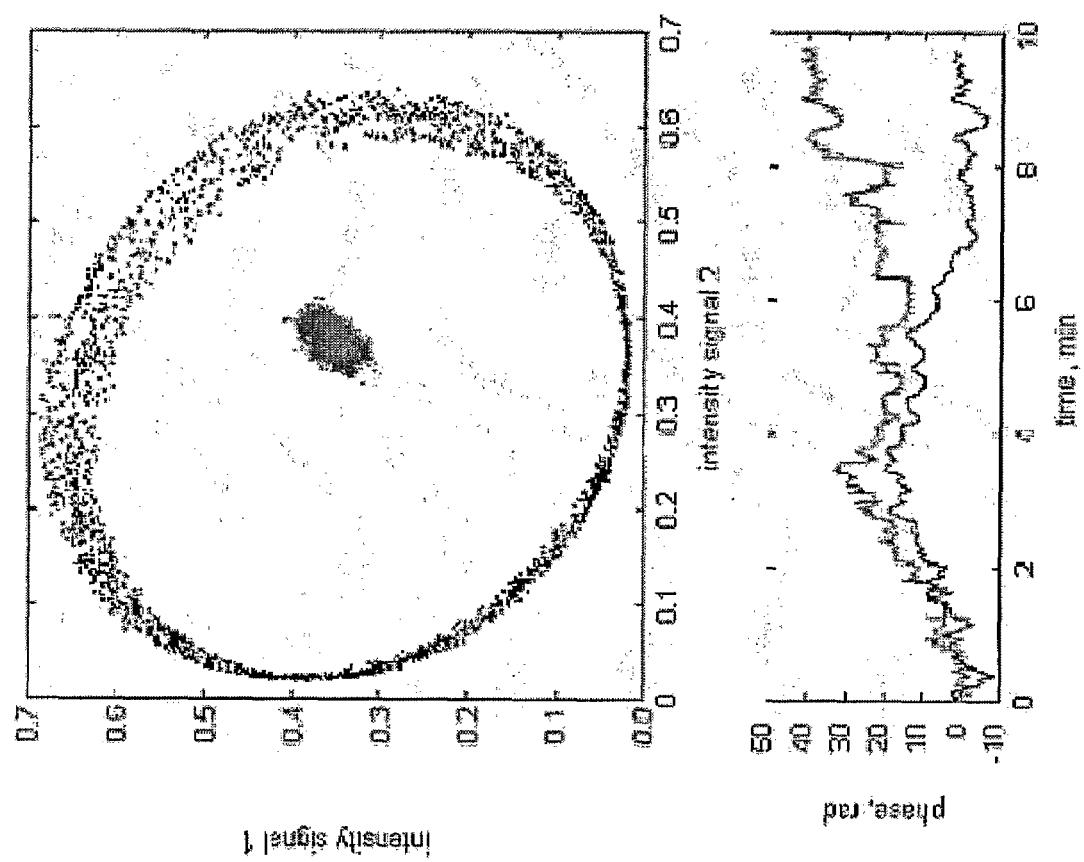

FIG. 23 shows precisely how closely the counter-propagating signals along different paths correlated as to processed phase angle data. The upper plot in FIG. 23 shows the close match between the shapes of the phase difference in the counter-propagating beams on a 10 mS time scale, showing that the traces track closely. In the event of a disturbance, as shown in the lower expanded time-scale plot, a time shift is shown between the responses of the two counter-propagating beams. This is due to the difference in propagation time for the occurrence of an event at a location in the detection zone that was closer to one phase receiver than the other, such that the phase variation arrived sooner. Channel 1 and Channel 2 in FIG. 23 refer to the two counter-propagating directions.

FIG. 24(a)-(e) compare the detector intensity trajectories and phase plots obtained in a range of different experimental conditions using a system as described herein. Two independent phase-related detector values were sampled repetitively over the time scales shown, producing trajectory data values and phase-time signatures that are plotted (or otherwise encoded) on the same graphic presentations in different shades. These data values were collected with no particular disturbance locally affecting the phase relationships, demonstrating a typical range of phase variation the beams from environmental drift and general ambient conditions. In the absence of a localized disturbance, the calculated phase differences in the counter-propagating directions should substantially overlap if the phase measurements are accurately obtained.

FIGS. 24(a) to (e) show various conditions in which the traces are larger or smaller and more or less eccentric. The phase measurements are insensitive to the shape and the size of the trajectory, as shown by the closely corresponding phase-time plots, except that the correlation becomes more noisy when the maximum-to-minimum intensity value spans become very small (i.e., the diameter of the trajectory shrinks) as in FIG. 24(d). The measurement technique becomes unworkable only if the size of the trajectory projection shrinks all the way to a point (FIG. 24(e)) or to a line (not shown).

Figure 25:
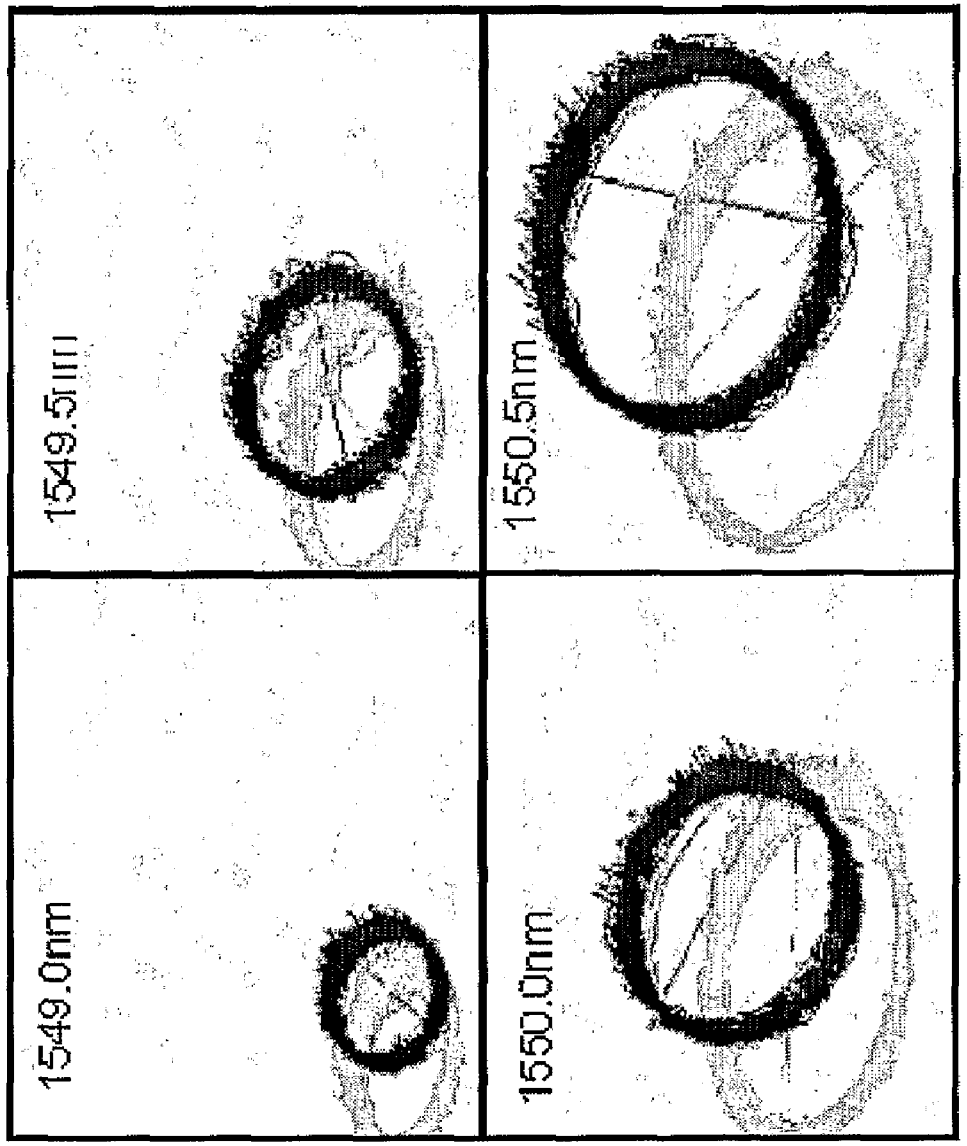
FIG. 25 is a comparative illustration of intensity plots as in FIG. 21, showing that the size of the circular trajectory is in part a function of wavelength, the data being collected for a 1 km fiber system.

FIG. 25 demonstrates that in the event that a trajectory projection becomes small, then without changing other aspects it is possible to increase the size of the projection by just a small change in wavelength. Because the polarization transformation through a fiber depends in part on wavelength, the intensity distribution in the orthogonal polarization components of the two beams being combined, and hence the size of the projected circles, can be adjusted by changing the operating wavelength. The wavelength dependent changes can be advantageously exaggerated by using birefringent components right after the light source. In FIG. 25, a change in wavelength of 1.0 nm generally doubled the circular trajectory size. This effect can be used advantageously to enhance the signal to noise ratio for measurement of the phase difference and detection of the disturbance location. The change can be a matter of switching between available wavelengths under control of a processor to correct a perceived reduction in signal to noise ratio, or the operational wavelength can be changed in a regular and repetitive manner during measurements.

Phase Detection Based on Fiber Optical Coupler with Three or More Output Ports

The light signal has a phase characteristic that can be used to provide a phase-time signature, and can be accurate if handled as described. The following examples concern applications of the idea of discerning a phase-time signature from two independent variable intensity values. However, according to further inventive arrangements, do not depend on time variations in polarization state. These embodiments further reduce the measurement to sensing and correlating time changing phase relationships for two counter-propagating signals.

As discussed in the prior art section, it is known to use two-by-two couplers at opposite ends of a two-fiber counter-propagating signal path, using the interference between the signals at a receiving end in an effort to develop a signal that is to be correlated at opposite ends to identify the location of a disturbance. As also described, the interference intensity of the two signals is not an effective signal for this purpose because of confounding polarization problems.

Moreover, a two-by-two coupler as in the prior art cannot alone produce two independent phase related intensity variables from which phase can be derived (at least not without polarization processing as well). In a two-by-two coupler, the sum of the two output intensities must equal the total input power. Assuming a given input power, the two output intensities are linearly dependent on each other. If one increases, the other must decrease, their sum being a constant so long as the input power is constant. In order to generate sufficient information to discern phase, one needs at least two independent variables that are related to phase. One method as described above is to respond to different polarization components. Additional methods are now presented, to illustrate the principle without reliance on polarization components. These methods are particularly useful, effective and inexpensive as well.

At least two independent intensities useful for discerning phase, can be obtained by the use of a coupler with three or more output ports, as the device that couples the combined signals from two or more signal paths, onto two or more detectors. In a disturbance locating system with counter-propagating dual beams, such as two optical fibers, such couplers are provided at both ends.

In the case of a coupler with at least three outputs (at least two of which are to be used as sources of independent variable data), the sum of all the output intensities still equals the input intensity. However, any two output intensities are independent from each other. According to an inventive aspect, the distribution of power among the two of at least three output ports of such a coupler, is arranged to depend at least partly on the phase relationship of at least two input beams, at least one of which traverses the detection zone, and which are both combined by the coupler.

Preferably, the coupler has equal power distribution among the outputs when only one input beam is present, and a power distribution that varies between two of the three outputs as a function of the relative phase differences between two input beams that are combined as inputs. Some alternatives embodiments are possible to achieve this arrangement. In the following discussion, a 3×3 coupler with equal output power distribution from one input is used as an illustrative example.

In this embodiment, two signal paths are combined by the use of a three-by-three coupler, and at least two of the three signal outputs are applied to photo-detectors and their intensities are sampled. These sampled intensities, or a linear combination of these intensities, such as their sum and the difference, produce two variables that are used for obtaining the phase relationship via multi-dimensional data analysis that is substantially similar to the polarization state trajectory analysis discussed above with reference to other embodiments. For purposes of illustration and explanation, the sum and difference values of the sampled two intensities, are interpreted by a processing algorithm as the X and Y coordinate values of sample points plotted (or otherwise encoded) on a two-dimensional trajectory curve. An eccentric elliptical progression is produced if the data is plotted graphically (or otherwise encoded) as a closed pattern (although as already discussed, the matter of graphic presentation is optional). The size of the elliptical progression or trajectory can vary, especially due to changes in the polarization conditions of the launched light signals. The position of a sample point on the trajectory is determined by the instantaneous phase relationship of the input beams.

The elliptical pattern can be normalized into a circular pattern for further processing similar to the technique described previously. This includes mathematically eliminating its eccentricity, defining a center origin and encoding the angular position around the origin as the phase varies. The angular position of each sampled point, with respect to the center of the circular trajectory, is interpreted as a phase variable associated with the two beams of the optical signal propagating in one of the two opposite directions at the sampled point in time. The process is carried out simultaneously and repetitively for both directions.

The foregoing technique optionally includes one or more polarization controllers to maximize the size of the circle that results from normalizing and plotting (at least in the processing logic) the sum and difference of detector sampling values on the x-axis and the y-axis. Such a polarization controller makes it possible to improve the signal to noise ratio of the measurement of phase change, by maintaining the swing or span of values at least to a desired threshold, namely by changing the polarization conditions if the size of the trajectory shrinks to a small span or even to a line or point.

There are phase effects associated with the polarization states of the dual beams of the counter-propagating signals, as described previously. The arbitrary polarization relation of multiple interfering beams introduces phase factors. Those factors do not depend on the location of the disturbance, but rather depend on the relative polarization relationships. According to an aspect of the present invention, a system can be configured with two 3×3 couplers that each have at least two out of three outputs coupled to detectors, so as to eliminate adverse polarization effects. As explained further below, and in a manner comparable to the polarization embodiments already discussed, when a disturbance affects the two counter-propagating optical signals, the effect at least comprises a temporal change in the phase relationships embodied in each of the signals. The invention seeks to focus directly on the phase variation as the operative parameter to be used for the location measurement, as opposed to parameters that may become complicated by polarization state issues.

The use of a 3×3 coupler for phase discrimination is proposed in K. P. Koo, A. B. Tveten, et. al., "Passive stabilization scheme for fiber interferometers using (3×3) fiber directional couplers", Appl. Phys. Lett., Vol. 41, No. 7, 1 Oct. 1992, p 616., as a technique applicable in one direction to deal with polarization fading. In another example, U.S. Pat. No. 5,313,266—Keolian et al. teaches a 3×3 coupler in a passive phase demodulator. According to an aspect of the present invention, a 3×3 coupler is employed as a signal launching and combining element in a location detection system with counter-propagating signal pairs, which is not found in the cited prior art. According to another aspect of the present invention, the outputs of 3×3 couplers are applied to novel data processing techniques as discussed herein, to discern time changing phase relationships from trajectory projections, which techniques are particularly effective for location determination in counter-propagating interferometer arrangements as disclosed and claimed.

According to the invention, output detector readings from two of three coupler outputs can be combined to collect trajectory progressions, that plot to closed trajectory loops.

This technique preferably employs the sum and difference of two detector readings on a selected two of at least three coupler outputs. If sample values processed as sum and differences are plotted (or otherwise encoded) in a Cartesian plot, the result is an ellipse. The X and Y axes are sine- and cosine-related variables representing a phase difference, particularly if the data is further processed to normalize the trajectory to a circle centered on an origin. The change in the phase relationship between two signals along different paths propagating in either of the two opposite directions can be calculated by measuring the relative angle around the normalized circular trajectory, as described below.

As described in Koo, supra, the output intensities for port 2 and 3 of a 3×3 coupler can be represented as follows, $$I_2 = B_1 + B_2 \cos \Delta\phi + B_3 \sin \Delta\phi$$

$$I_2 = B_2 + B_2 \cos \Delta\phi - B_3 \sin \Delta\phi$$

therefore the sine and cosine terms can be obtained by simple sum and difference of these two intensities:

$$I_s = I_2 + I_3 = 2B_1 + 2B_2 \cos \Delta\phi$$

$$I_d = I_2 - I_3 = 2B_3 \sin \Delta\phi$$

when we plot $I_d$ as a function of $I_s$, an elliptical trajectory results.

The phase difference $\Delta\phi$ can be readily obtained from the elliptical trace, for example, by renormalization of the elliptical trace into a circular trace, and calculation of the relative angle for each data point.

The time dependence of the phase difference can then be calculated by the following, which is discussed here as a non-limiting exemplary procedure, and it will be apparent that several other methods can be employed in a similar way.

The collected intensity data forms a closed loop on a two-dimensional x-y plane, which is first transformed to a circular loop. The origin of the circle is then shifted to (0,0). The angle with respect to the x-axis is calculated from the tangent of the X and Y values for each sample point, i.e., by taking $\theta(t) = \tan^{-1}(y(t)/x(t))$ for each point $(x(t),y(t))$ corresponding to a particular time t. The temporal phase dependence is $\theta(t)$. This procedure is repeated for the counter propagating channel and the value of $\theta'(t)$ is calculated. The location of the event is determined by calculating the value of $\tau$ for which the correlation between the two functions $\theta(t+\tau)$, and $\theta'(t)$ is the highest during a measurement interval. Incrementally different positive and negative values of $\tau$ can be tried, up to positive and negative values equal to half the signal propagation time through the detection zone, thereby testing for correlation at incremental locations throughout the detection zone. Knowing the velocity of the light in the waveguide medium, the location of the phase disturbance can be calculated from the value of $\tau$ at which the correlation is highest. Other techniques exists for calculating directly the correlation between the two functions $\theta(t+\tau)$, and $\theta'(t)$, to obtain the value of $\tau$.

Figure 26:
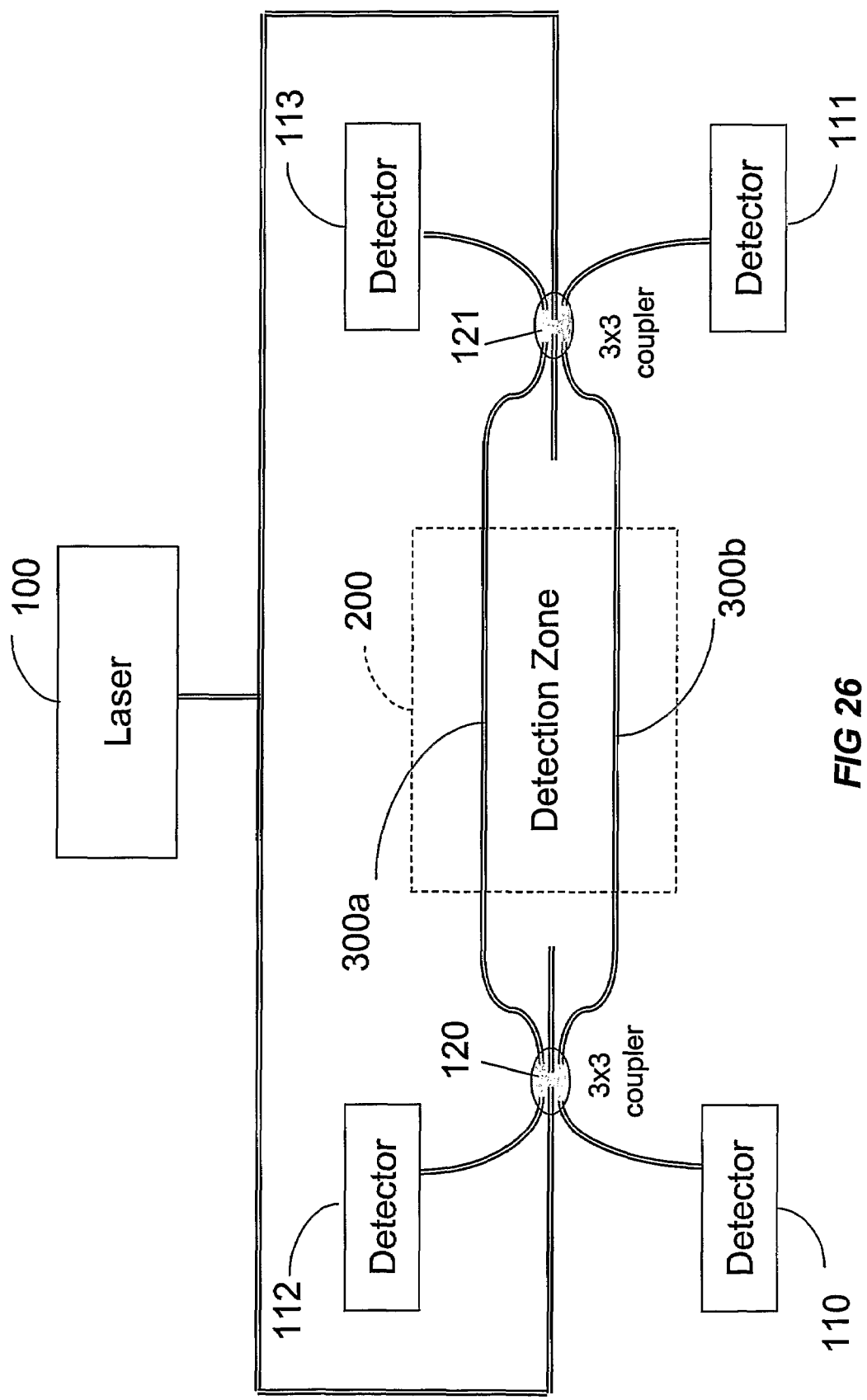
FIG. 26 is a block diagram of another arrangement of the distributed fiber sensor using a 3×3 fused fiber coupler.
Figure 27:
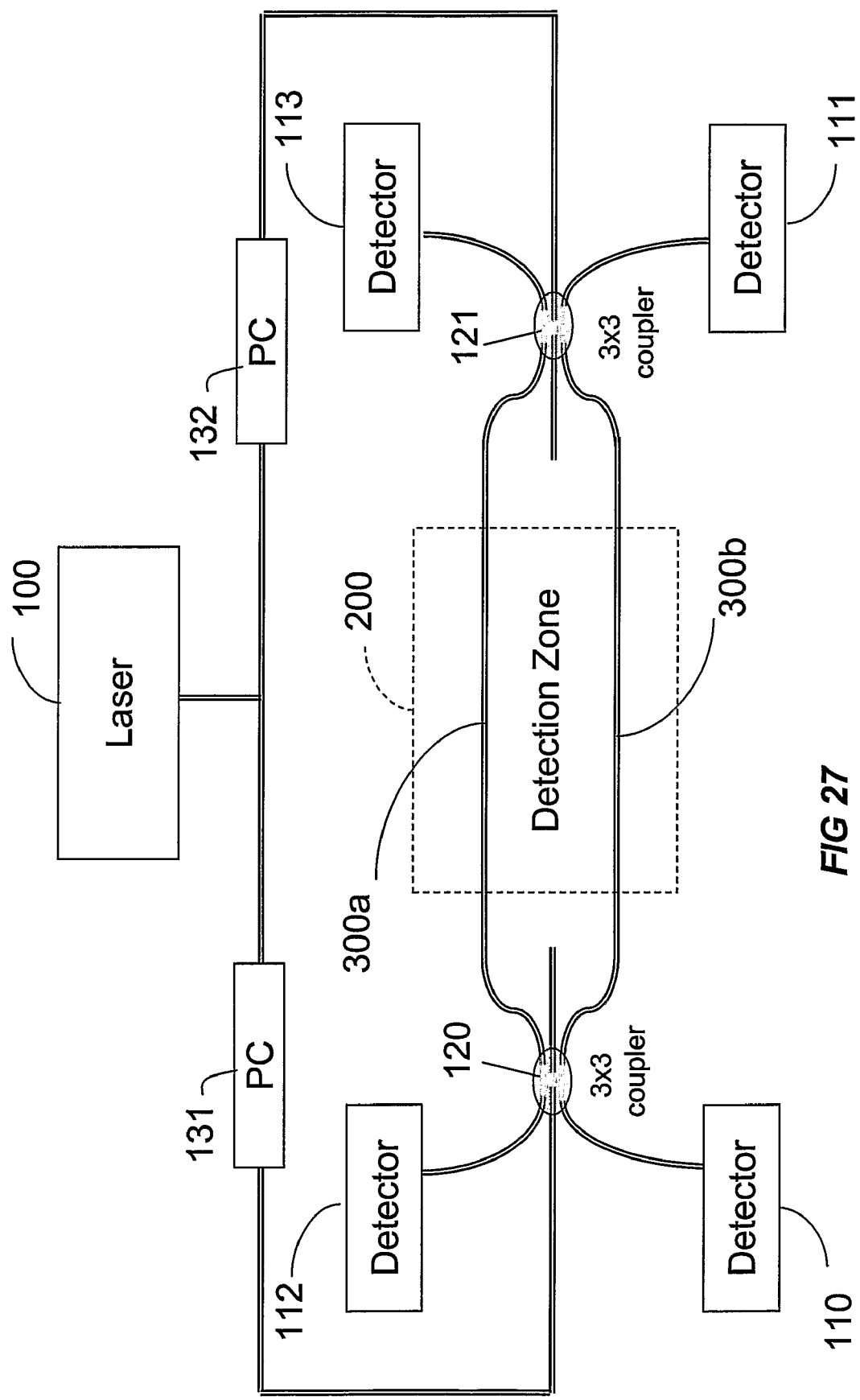
FIG. 27 is a block diagram of another arrangement of the distributed fiber sensor using a 3×3 fused fiber coupler, with individual polarization controllers for each of the counter-propagating signal directions.
Figure 28:
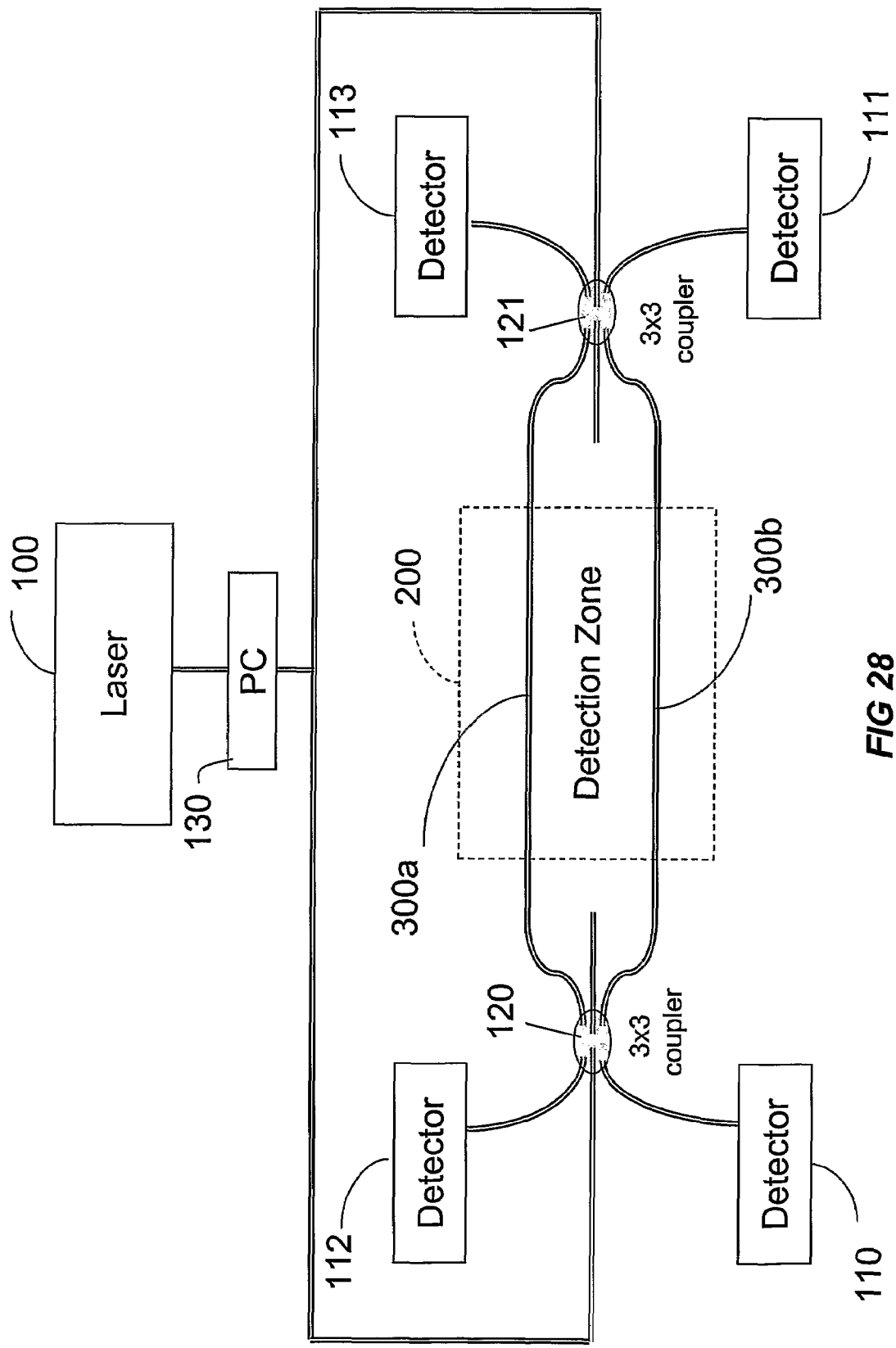
FIG. 28 is a block diagram of another arrangement of the distributed fiber sensor using 3×3 fused fiber coupler, with a polarization controller applied commonly for both of the counter-propagating signal directions.

FIG. 26 is a block diagram showing one arrangement of the remote distributed fiber sensing system of the invention based on three-by-three couplers. In this arrangement, light signals for the two optical channels are derived from the same light source 100. The light splitter/combiner 120 and 121 can be a commercial 3×3 fiber coupler and launches the signal into the two legs of the detection zone for its respective end. One or a plurality of polarization controllers 130, 131, 132 preferably but optionally is placed so as to advantageously control the optical signals from the laser source 100 into the light splitter/combiners 120, 121 as shown in FIG. 27 and FIG. 28. Alternatively, a wavelength tuner can be provided. The polarization control and/or tuner are optional in view of the rarity of the situation wherein the trajectory size shrinks so small as to be incapable of representing a phase angle, but in a given application such as a high security intrusion detection system, controls and tuners may be advantageous.

The optical signals that emerge from the splitter/combiners 121, 120 (now operating as combiners for their respective phase receiver ends) are coupled into the respective pairs of detectors 110, 112, and 111, 113. Each pair of detectors develops two variable values that change independently as the phase relationship of the combined pair of signals into the combiner coupler 121 or 120 varies, for example due to a disturbance. In the inventive method and apparatus, two detection beams are combined using optical couplers as elements 120, 121. This manner of combination of the detection beams causes the output of the pair of detectors after data processing to always fall at some point on a close loop formed by plotting on the x-axis and the y-axis a combination of the detector readings. This characteristic will be illustrated further below, including an explanation of how the close loop is transformed into a circle, and how it is possible and advantageous to maximize the circle.

The optical beam combiners 120, 121 combine the optical power from the two beams in the detection zone. The detector values vary with relative phase change, and the values are processed so that a progression through a period corresponds to a progression through a defined trajectory. That trajectory can be remapped (either graphically or simply as a matter of data value mapping) to provide the corresponding phase angles.

In the preferred arrangement the trajectory is obtained from sum and difference values and plots to an ellipse. The ellipse is normalized as a circle and centered. An elliptical trajectory is useful and if the character of the ellipse changes (e.g., its size), the trajectory can be adaptively mapped to a normalized circle. However, any trajectory that is traversed in conjunction with a phase swing through a full period of phase difference (e.g., zero to $2\pi$), and that repeats the same trajectory for the next period ($2\pi$ to $4\pi$, etc.), can be remapped onto a circle or into a succession of incremental phase angles, in a similar way.

The signal phase variation from one time sample to the next is proportional to the angular change between of the corresponding points on the remapped circle around the center origin (or to the incremental phase angles as otherwise remapped). Therefore, according to an aspect of the invention, the readings from a two pairs of detectors corresponding to the two counter propagating channels can be obtained and used as the parameter that localizes a disturbance in the detection zone 200 in which the disturbance causes a change in optical propagation properties.

The shape of the loop is generally determined by the optical characteristics of the light splitter/combiner, and the shape normally does not vary as a result of changes in the detection zone. However, since the signal in the two arms is subject to polarization changes, the size of the loop will change with the polarization state changes. The polarization changes are generally expected to be slow compared to the time scale of a disturbance (such as vibration at audible acoustic frequencies) so that polarization can be taken into account during the course of data processing. For example, readjustment of the size of the loop in calculating the angular change from the transformed circle that is derived from the loop can involve factors derived from a currently sensed trajectory size, and the size can be repetitively updated at some slower rate than the rate used for disturbance detection and applied as a constant.

This technique is generally sufficient but it is also possible adaptively to recalculate the trajectory size more frequently, which is advantageous if a detected disturbance can occur that markedly affects polarization on a short time scale, e.g., as the disturbance occurs, such as a disturbance that affects birefringence by twisting an optical fiber in the detection zone.

According to one inventive aspect, the changes in phase, derived from the angular change around a circle, represent the parameter by which the location of the disturbance is resolved. The precision with which the angular change between two points on the circular trajectory can be resolved is best when the trajectory circle is large because a larger diameter enables more precise resolution of the angle of a point than a smaller diameter, i.e., a better signal to noise ratio.

According to another aspect of the invention as explained below, the precision of the detection measurement can be maintained by taking certain steps to keep the circle large. These steps can include polarization state management using polarization controllers and/or tuning of the wavelength of the laser.

FIG. 26 is a block diagram demonstrating a preferred embodiment involving multiple bidirectional fiber signals and couplers arranged to combine the signals at the phase receiver end and to develop two independent phase related variables using two detectors at each receiver end. Whereas the optical beam combiner and splitter can be chosen from a variety of configurations, a 3×3 fiber optic fused coupler is preferred. In FIG. 26, two 3×3 couplers 120 and 121 are used in combinations with two pairs of detectors 111, 113 and 110, 112.

FIG. 27 and FIG. 28 are further embodiments that further include polarization controllers 130, 131 and 132 to enhance the signal to noise ratio by maintaining a maximum or otherwise optimal diameter for the phasor trajectory ellipses (or normalized circles), or avoiding the collapse of the same, as described above. The accuracy or resolution in discriminating a location for a disturbance is smallest when the trajectories are large, namely when a substantial proportion of the full scale span of digitizers in the detectors is used to obtain values from the detectors 110 to 113. In these configurations, the state of the polarization controllers can be adjusted by using the radius of the circle used to determine the phasor values as a feedback parameter.

A numerical data processing method is now described, as an exemplary but non-limiting technique for executing the procedures discussed. This method is explained in association with data plots (or other representation) showing examples and experimental results.

Figure 29:
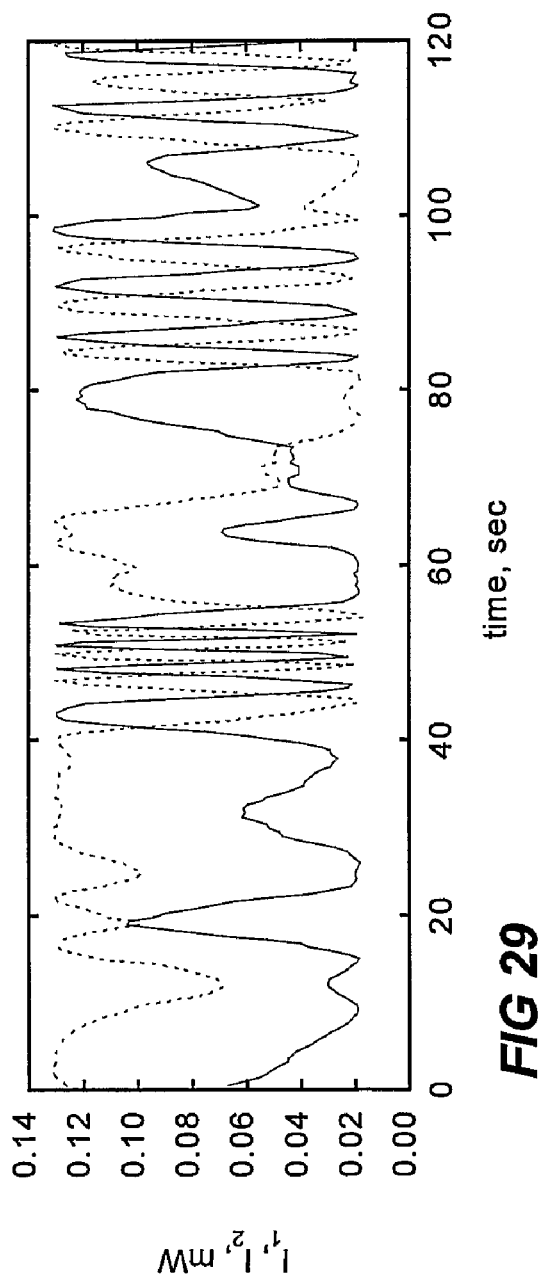
FIG. 29 is a time plot of the two intensities values measured by two detectors for the same propagation direction.
Figure 30:
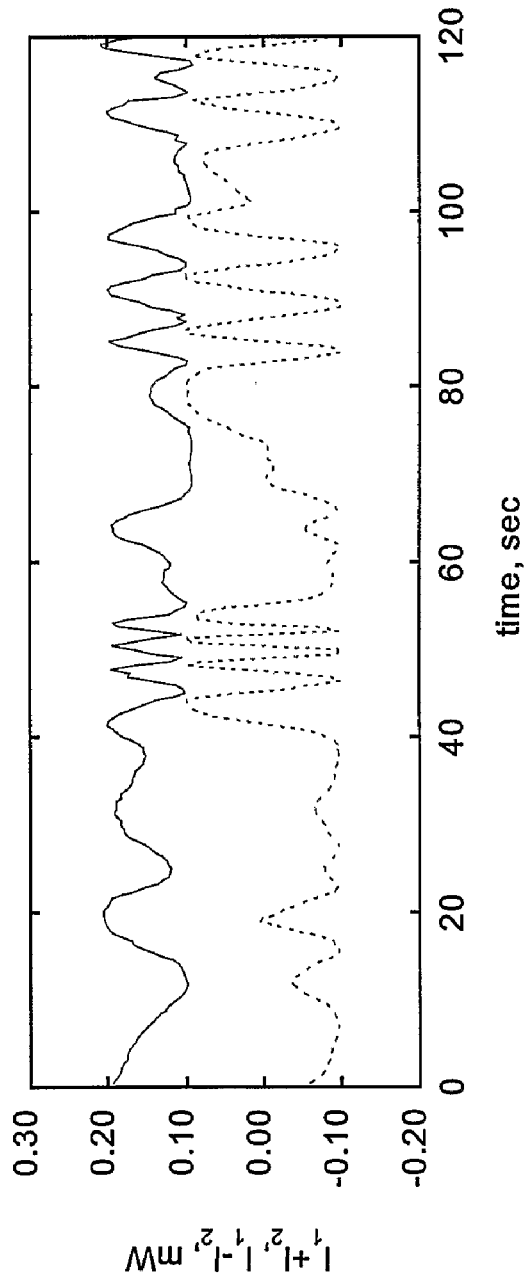
FIG. 30 is a time plot of the sum and difference of the two intensities values measured by two detectors for the same propagating direction as separately plotted in FIG. 29.
Figures 31A, 31B:
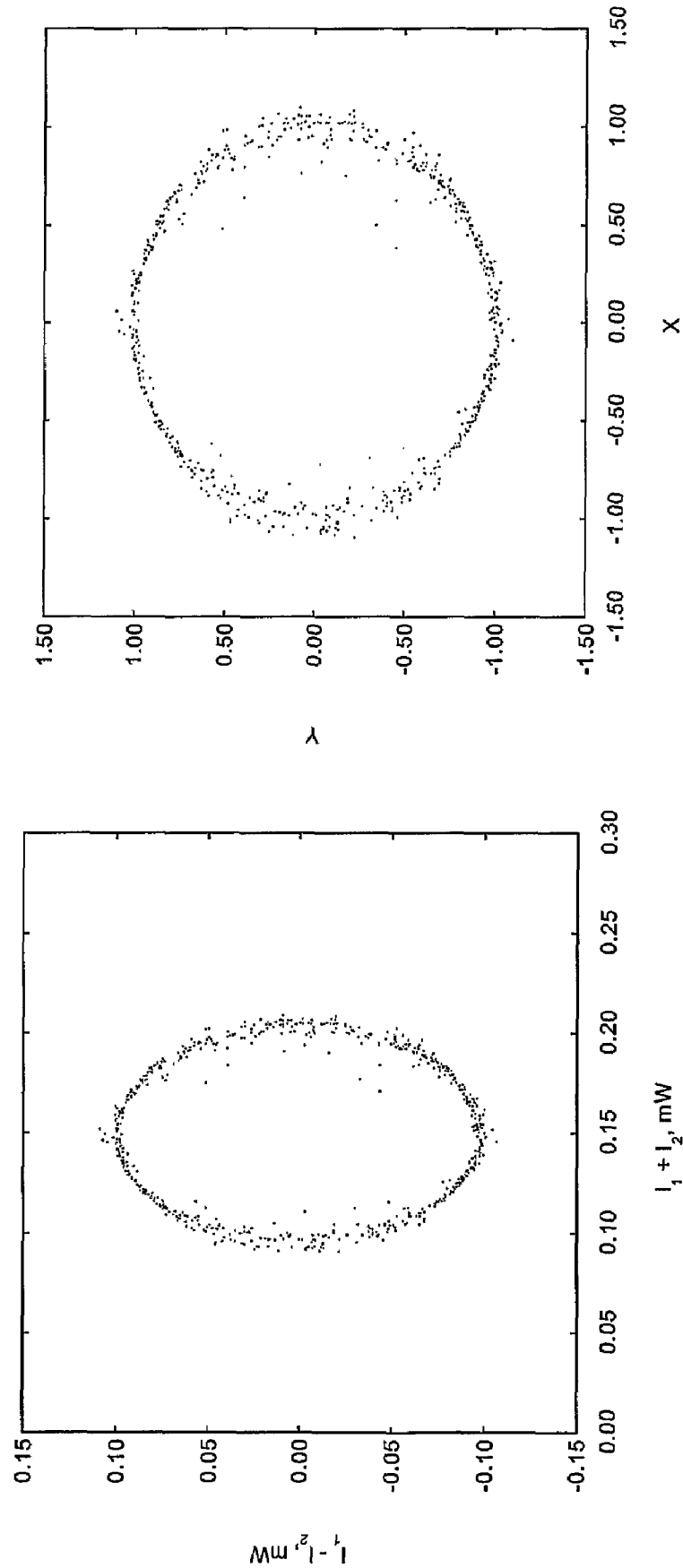
FIG. 31 is a comparison plot showing (a) an elliptical relation between the sum and difference of the two intensities values from FIG. 30, and (b) a normalized and centered circular trajectory of the values, as used according to the invention for relative phase calculations.

Raw intensity data signals from a pair of detectors monitoring the outputs of two of the three output ports of a 3×3 coupler at one phase receiver end of the detection system, are plotted (or otherwise encoded) as two time traces in FIG. 29. Similar data is generally observed for the pair of detectors for the opposite end, i.e., for the opposite counter-propagating signal. The readings from the two detectors are sampled, digitized and numerically or otherwise combined to obtain a value for their sum and a value for their difference. The sum and difference values are plotted in FIG. 30 as a function of time, showing the same data shown in FIG. 29. This same data is replotted (or otherwise encoded) as a succession of time samples in FIG. 31a, but without the time scale shown. In this plot, each point is shown as a mark placed at the point where the sum and difference values correspond to the positions along the x-axis and the y-axis, respectively. This results in a trajectory wherein the data values plot to points falling in a closed loop. The closed loop shown in FIG. 31 is a collection of data points over a time and number sufficient to infer that the data points represent a span of phase values. The trajectory figure shown in FIG. 31a, which in general forms an elliptical trace. A particular point in FIG. 31 corresponds to a particular instance in time, and to a particular phase relationship. It is not apparent in the plot as to which plotted (or otherwise encoded) angle corresponds to which phase angle, but this is not important because the succession of phase changes is the function that will be correlated between data values collected for the counter-propagating signals. The position of any sample plotted (or otherwise encoded) as a point on the closed loop trajectory in FIG. 31a can be characterized as a radial line of some length and angular orientation relative to a center of the trajectory pattern. The aspect ratio of the pattern is altered to transform the elliptical trace in FIG. 31a into a circular trajectory as shown in FIG. 31b, for example by equalizing the radial lengths, thereby stretching the lateral dimensions of the elliptical trajectory to the extent necessary to produce a circular one. The phase angle of a sample is now represented by the angle of its radius in FIG. 31b.

Figure 32:
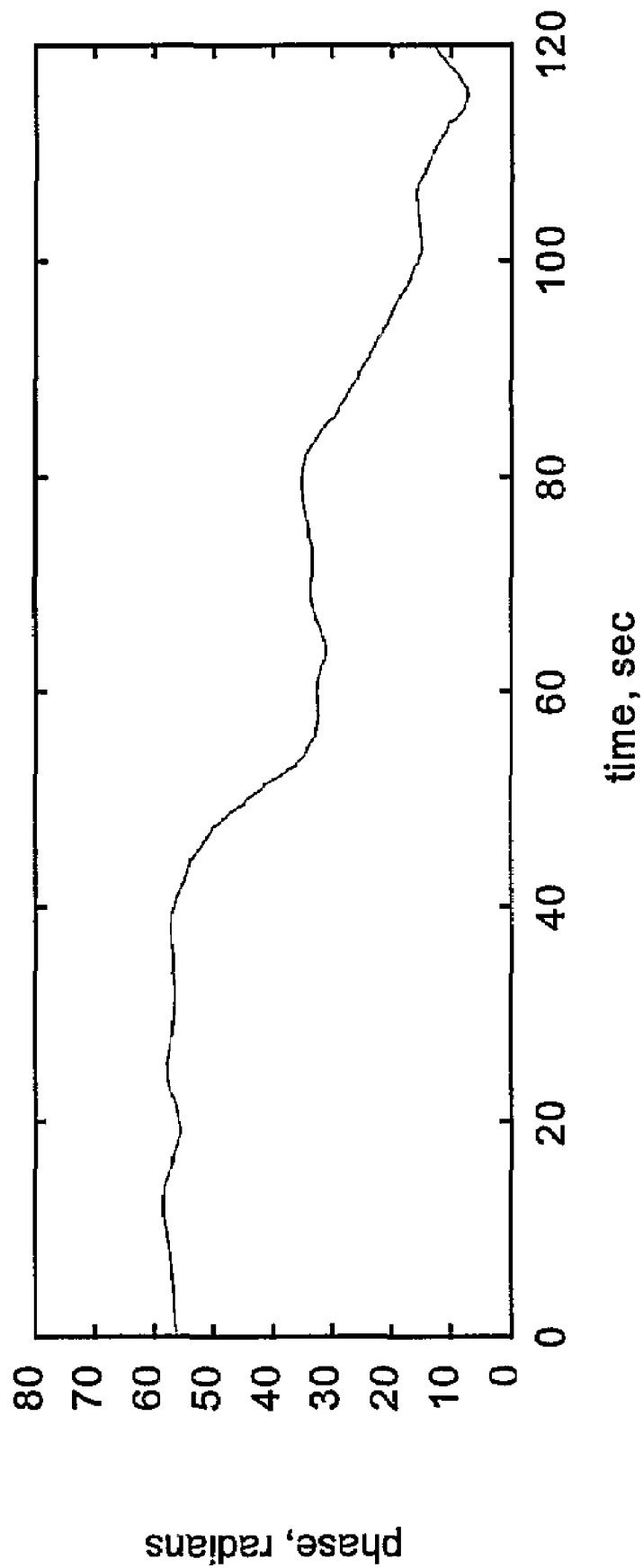
FIG. 32 is a time plot showing typical drift of relative phase calculated over a long time scale as labeled, for one of the counter-propagating light signals.
Figure 33A:
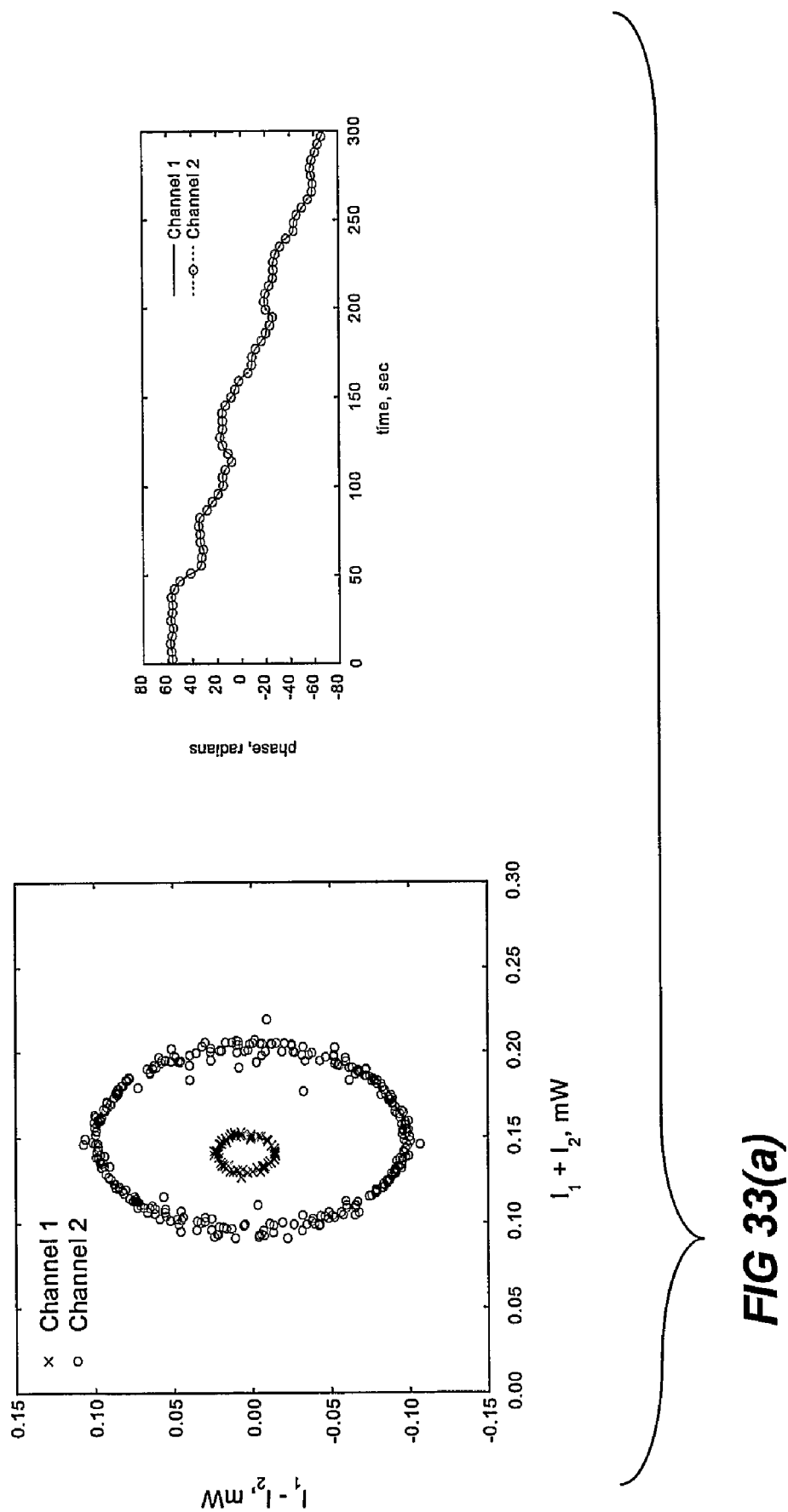
FIG. 33 ($a$-$d$) are sets of plotted elliptical relations between the sum and difference of the two intensities values and the corresponding calculated phase values for the two counter-propagating light signals.
Figure 33B:
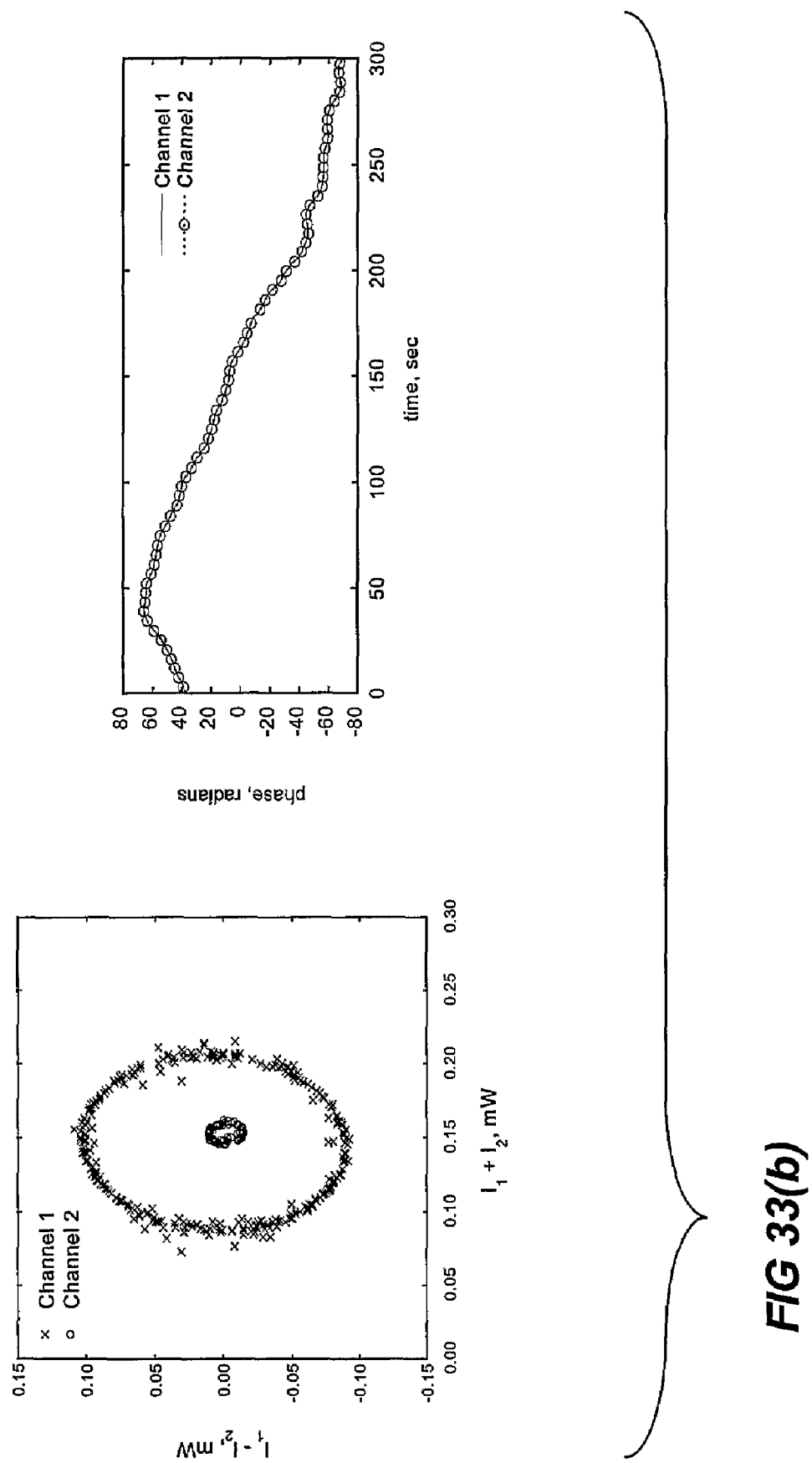
Figure 33C:
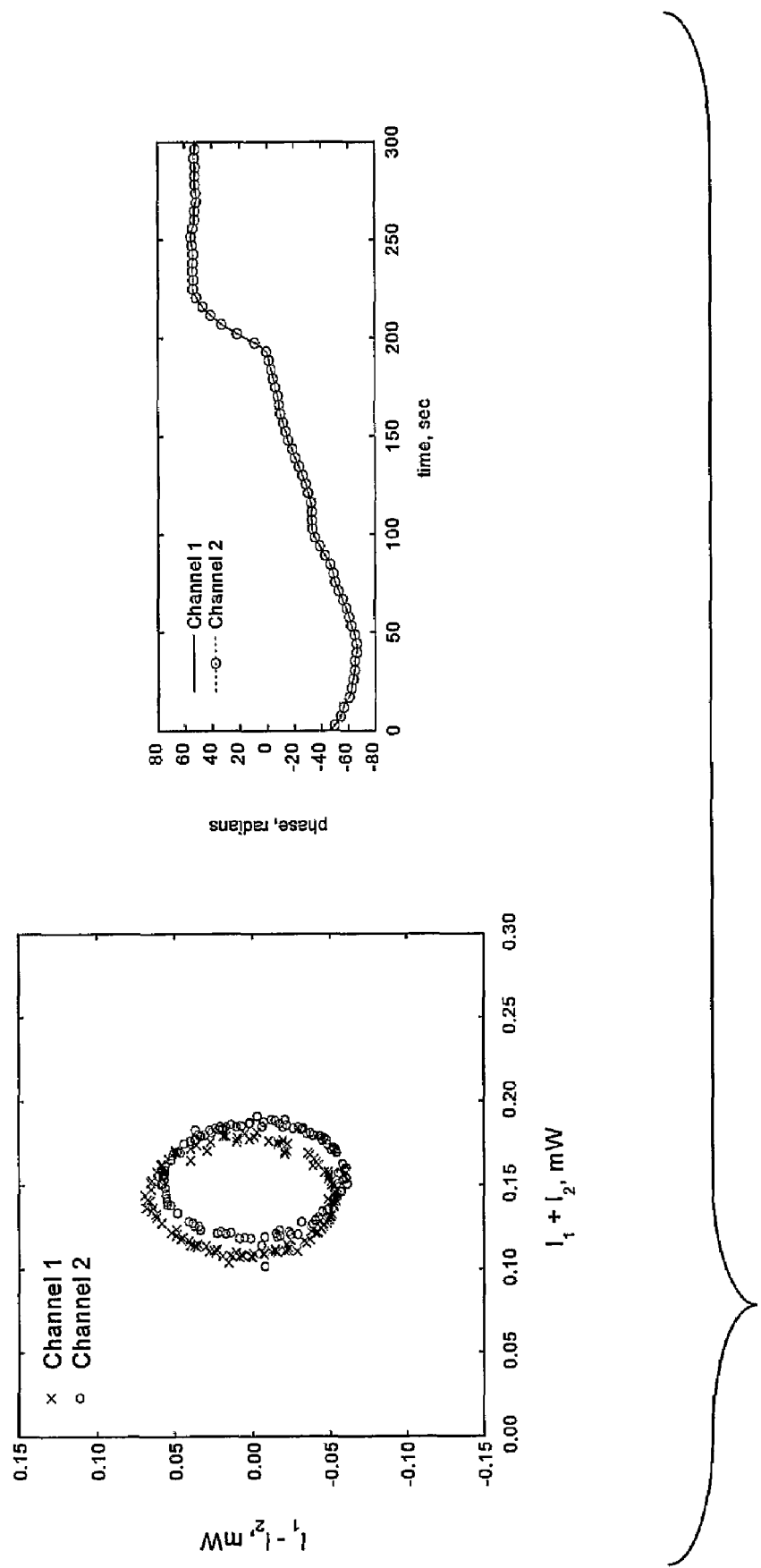
Figure 33D:
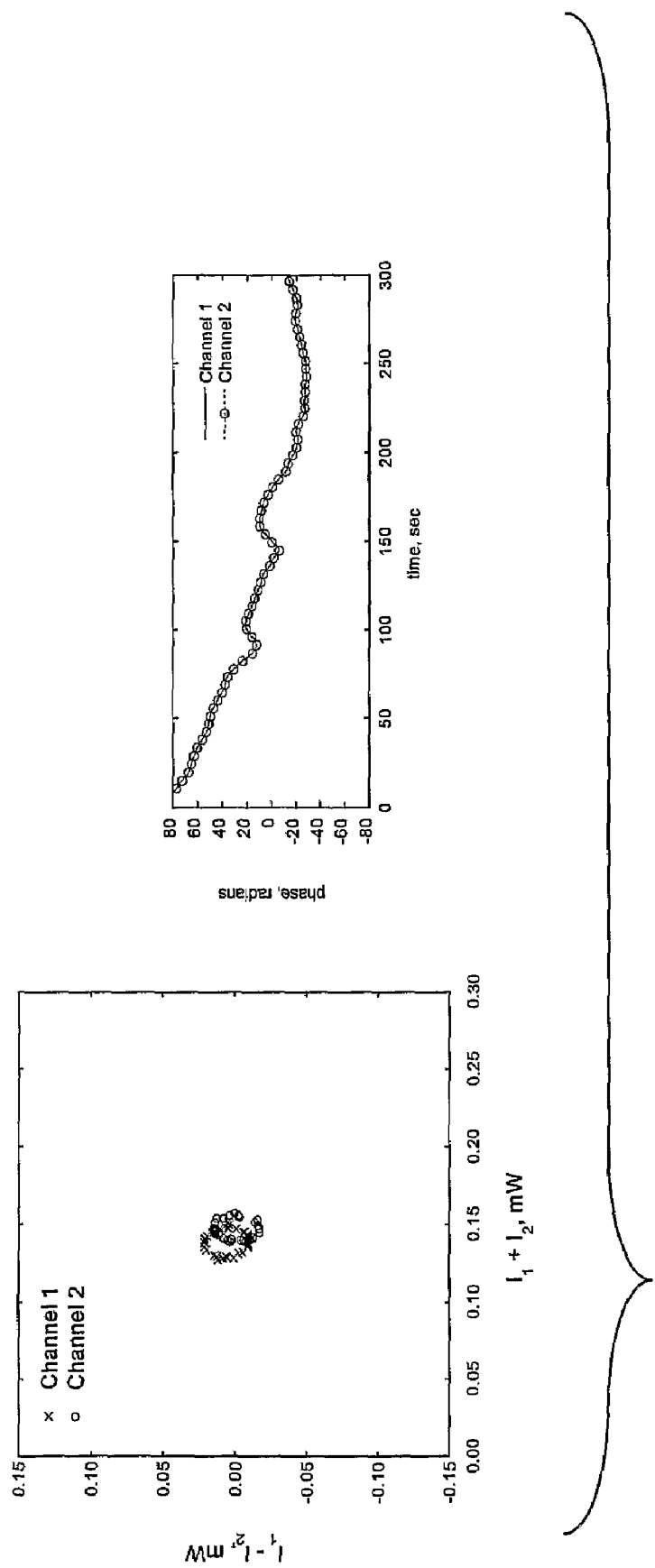

FIG. 32 illustrates a time plot of the calculated and accumulated phase angles in radians obtained by starting at a first sample and adding the phase angle change from that sample to the next sample, repetitively to integrate the change in phase angle over a time (two minutes in this example). The integrated value of the currently integrated phase compared to the starting phase value can be termed the "phasor."

FIG. 33(a) through (d) plot the phasor change results calculated based on the above described method. FIGS. 33a through 33d each show an example in which the trajectories and phasors versus time are plotted (or otherwise encoded) for both counter-propagating optical channels. The size of the trajectories can be seen to vary. The corresponding phasor change values substantially overlap. One can conclude that the polarization of the launch signal can be changed but there is no material effect on the measured and accumulated value of phase change of the system for the two counter propagating signals other than an possible polarization induced phase offset.

The signal to noise ratio can be advantageously improved by using polarization controllers, but the problem with trajectory size is specific to rarely occurring and short-lived polarization conditions, so that polarization management is not necessary for most users.

The phasor values correspond to the accumulated phase change. The absolute value of the relative phase angle is not needed because only the change is of interest for this example. On the time scale of seconds the two traces overlap because the phase change for the two counter-propagating signals is the same.

If a polarization controller is used in the system, there are several choices of configuration and operation. As shown in FIGS. 27 and 28, a polarization controller 132 can precede the power splitter 121 to control the incident SOP. A polarization controller 131, can be placed in front of the power splitter 120. Configuration of the polarization controller such as that shown in FIG. 28 is preferred when an acceptable signal-to-noise ratio, rather than the maximum one, is sufficient. Any one or more of the polarization controllers can be provided. The polarization controllers can be tuned to optimize the trajectory size, or simply switched when necessary to bump the polarization conditions away from a state at which the trajectory is too small for effective calculations. The change in wavelength, as discussed before may also be used to improve the signal to noise of the phasor measurements.

Figure 34:
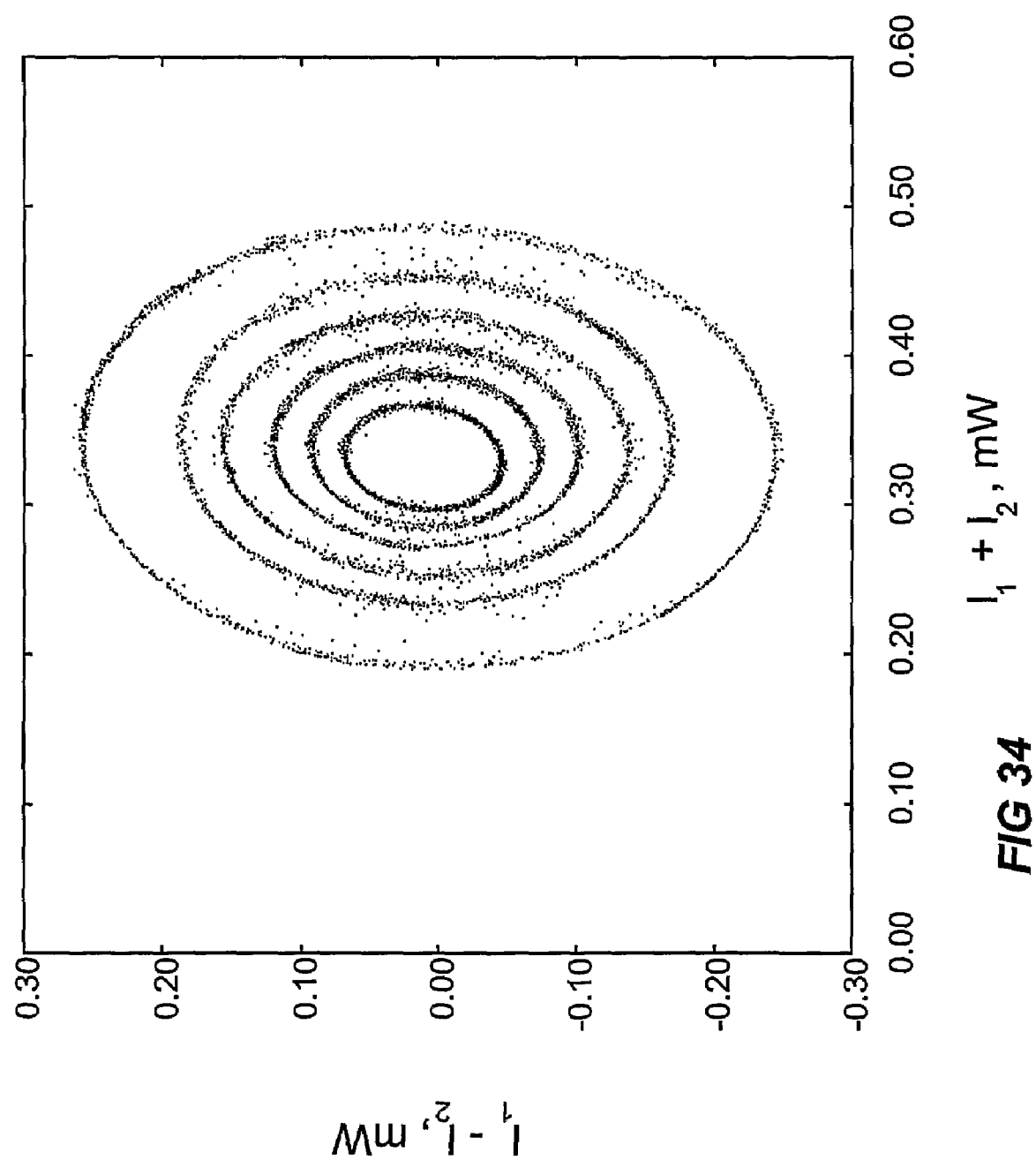
FIG. 34 contains overlaid plots for successive samples showing changes in the plot that occur when polarization of the combining beam is progressively changed.

One polarization related effect is the size of the trace. Because the interference effect is polarization dependent, if the polarizations of the interfering beams are not parallel to each other, only those polarization components that are parallel will interfere, resulting in a smaller change in the intensity of the signals coupled through to the detectors. This will further cause the size of the trajectory of the phasor change to be smaller, an example of a succession of different polarization states being shown in FIG. 34. However, the size of the trace does not prevent or affect the phasor calculation, provided that the trace has a nonzero diameter from which an angle can be found. The configurations with polarization controllers, shown in FIGS. 27 and 28, are non-limiting examples. Other configurations exist.

Figure 35:
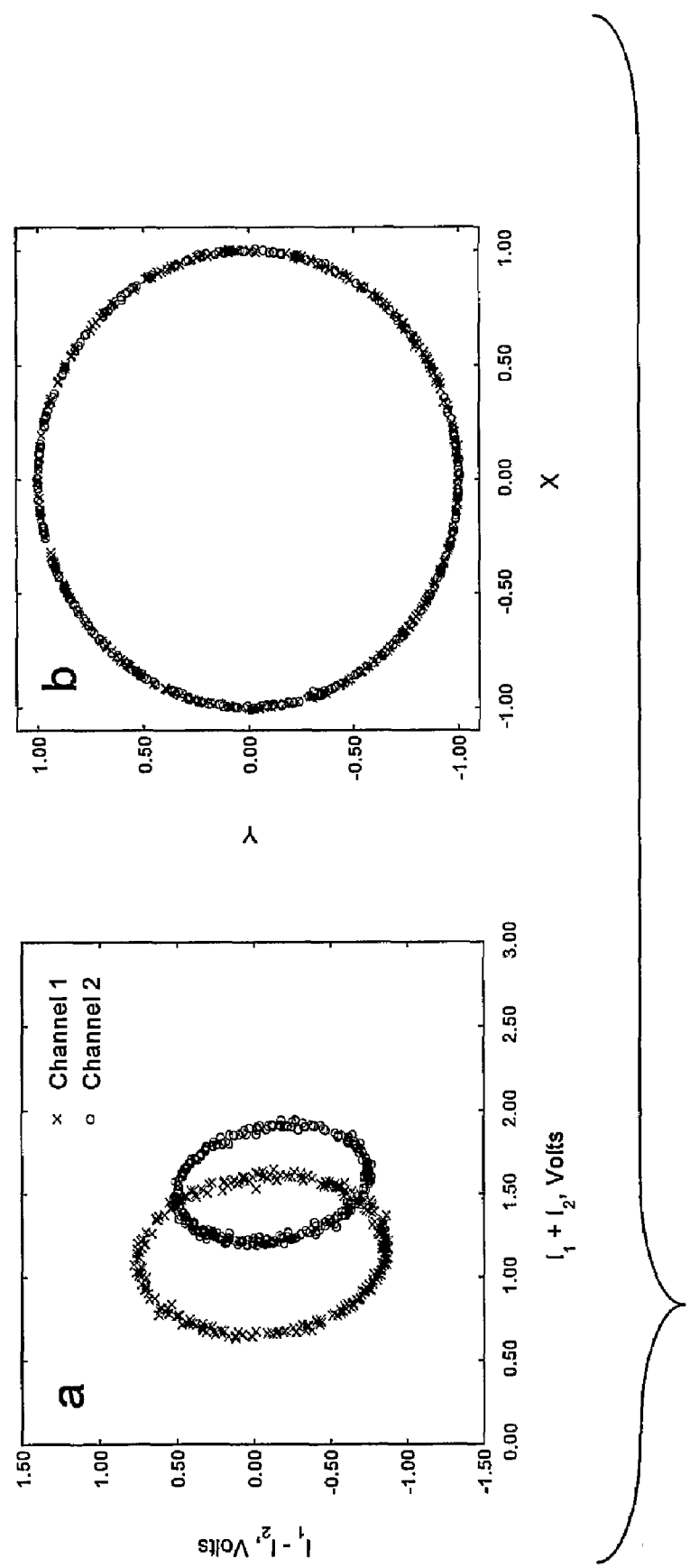
FIG. 35 shows experimental plot data for (a) an elliptical relation between the sum and difference of the two intensities values measured by sets of two detectors for each of the two propagating directions and (b) the normalized circular trajectory for phase calculation. The relative angle of each plotted point from a reference angle around the center of the circle as an origin is regarded as the instantaneous phase.
Figure 36:
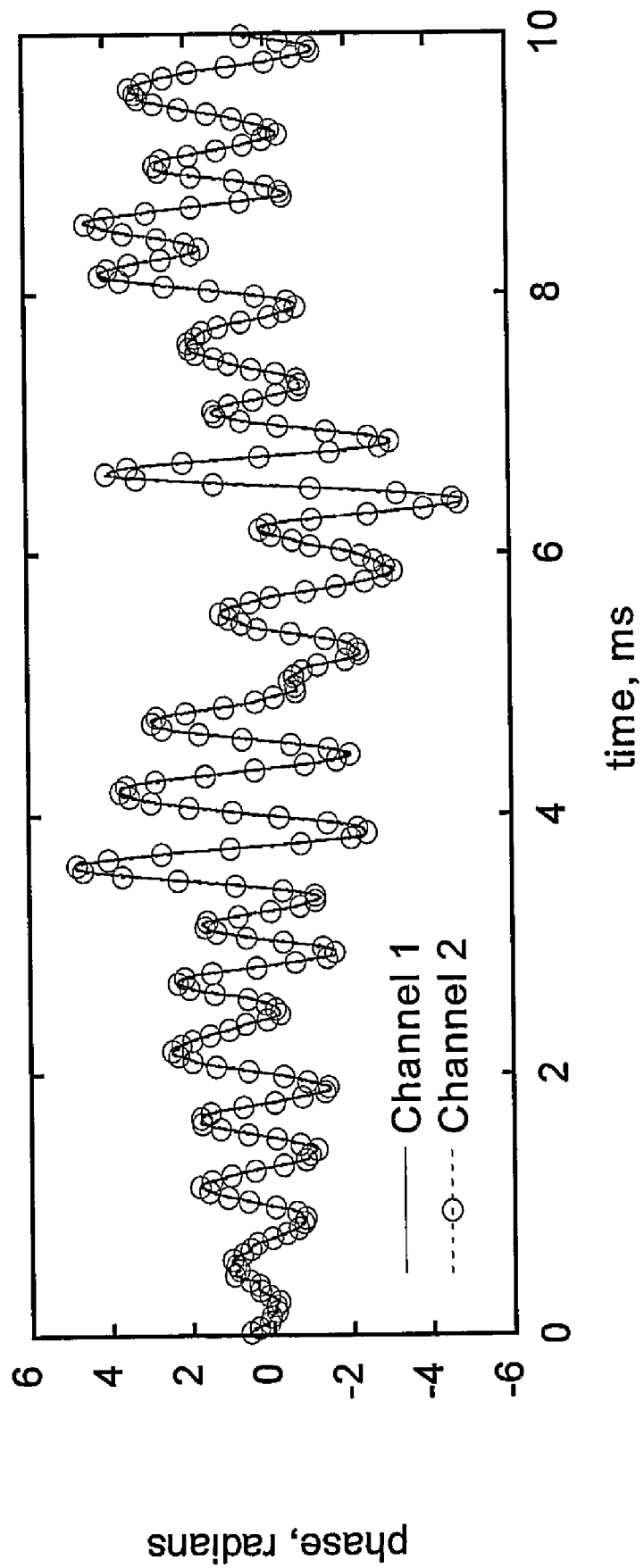
FIG. 36 is a time plot of relative phase versus time, showing the data from FIGS. 35($a$) and ($b$), showing the time difference over a short term representing the signature of a disturbance. This plot shows the high correlation of the phase-time signatures of the two counter-propagating signals according to the inventive technique.
Figure 37:
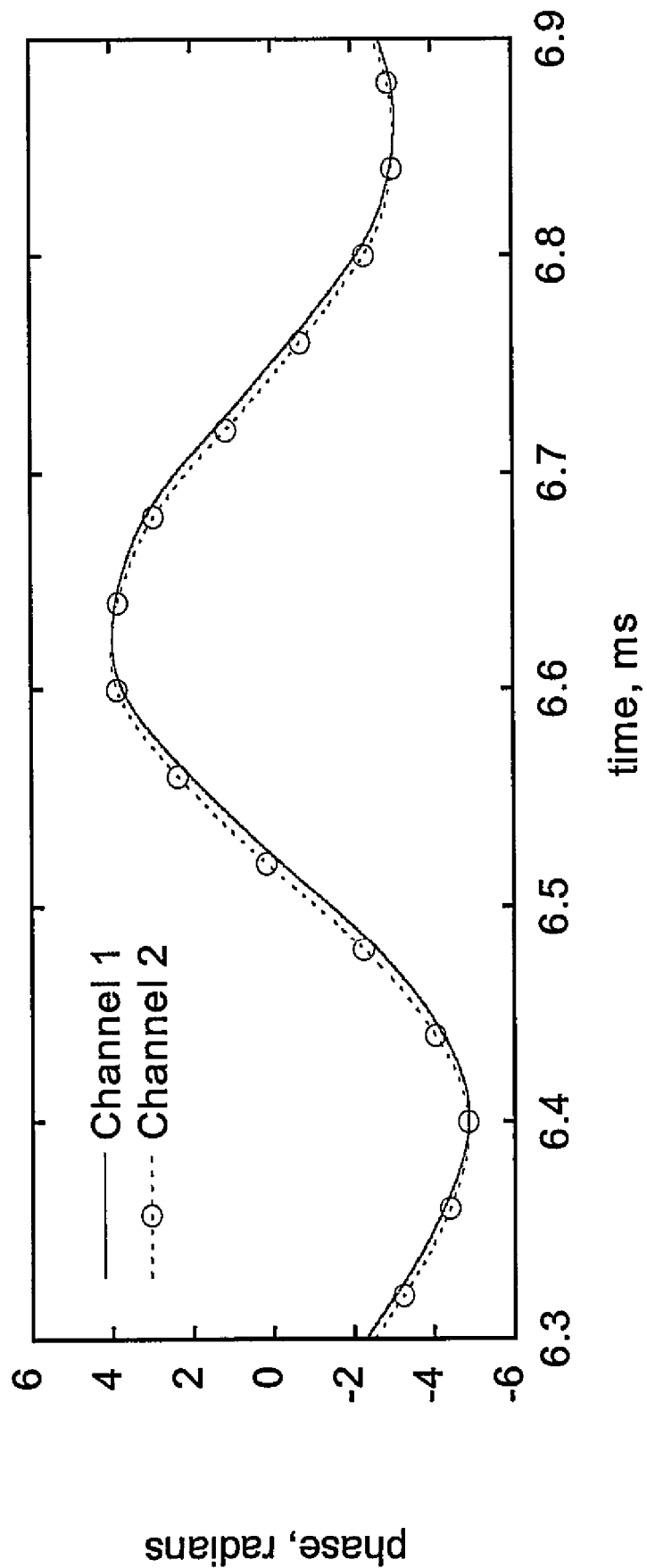
FIG. 37 is a plot showing a time slice from FIG. 36 over an expanded time scale, showing that there is a readily measurable time lag between the signatures of the disturbance in the counter-propagating signals. This time lag is due to the difference in signal propagation time between the location of the disturbance and the respective detectors, and is used to determine the location of the disturbance.

Experiments testing these concepts, using the configuration shown in FIG. 28, are demonstrated by data plotted in FIGS. 35-37. FIG. 35(a) shows raw trajectory plots of sum and difference detector output values. FIG. 35(b) shows the same data transformed and normalized.

The data in FIGS. 35-37 represent integrated phasor results for two counter-propagating channels during a phase disturbance event. The good signal to noise ratio and the appearance of a single closed loop for each channel indicate that the polarization states have not changed substantially over the time scale of the event. The amplitude of the raw trajectory data at about one third to one half of the detector encoding span was more than sufficient to determine angular phasor data and in the normalized trajectory graph, the two channels overlap. The phasor data correlated very closely over the 10 mS span shown in FIG. 36.

Although the data appear overlap exactly in the phasor time plot of FIG. 36, there is a detectable temporal shift shown clearly in FIG. 37, arising from the difference in time of arrival of the signals. This difference in time is used to calculate the location of the source of disturbance by correlating the two signals as discussed previously.

Figure 38:
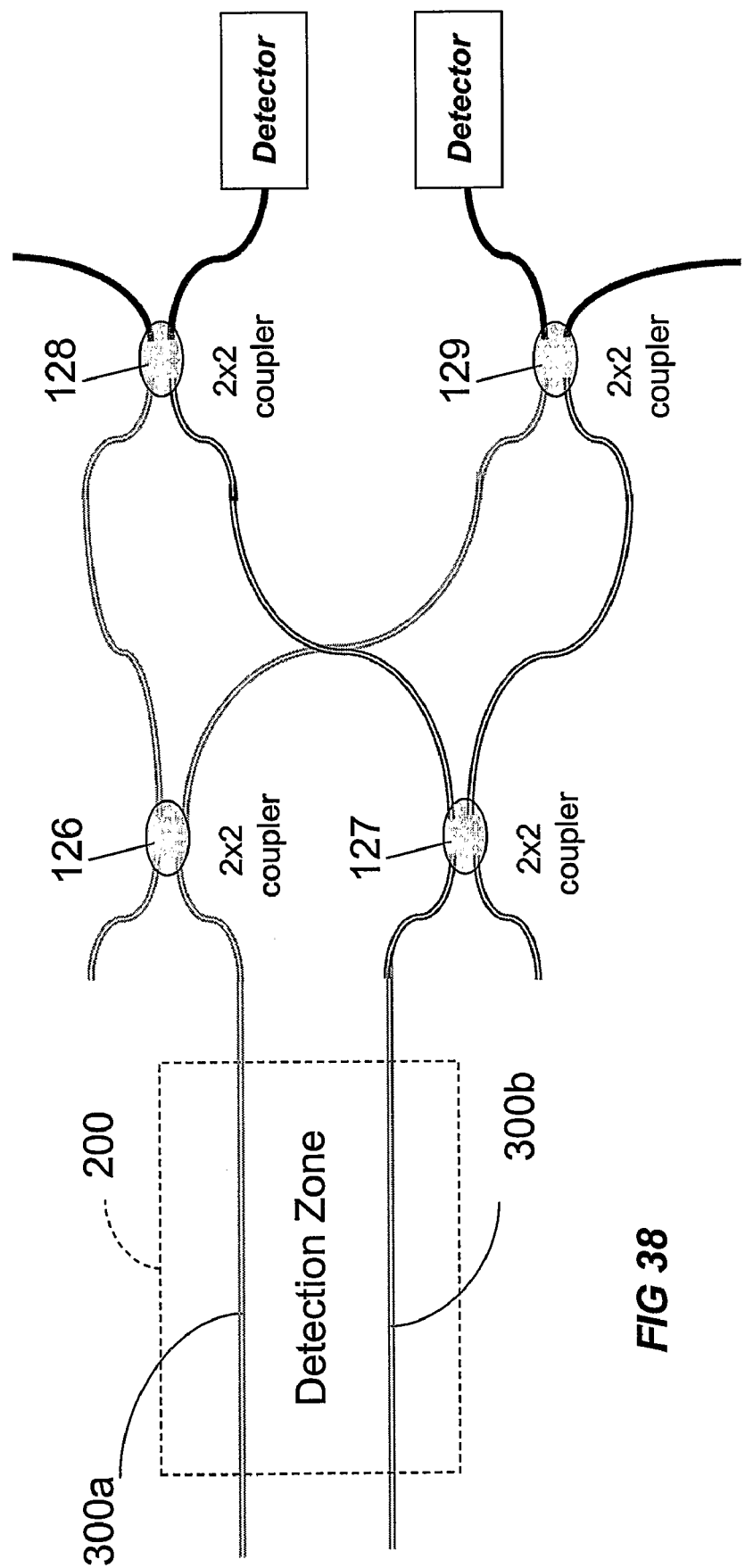
FIG. 38 is a block diagram of another arrangement of the distributed fiber sensor using multiple cascaded 2×2 fused fiber couplers.

FIG. 38 shows another embodiment of the invention, demonstrating that it is not necessary to use 3×3 couplers specifically to obtain two independent phase related variable values from which a trajectory can be derived. In this embodiment, the 3×3 couplers of previous embodiments are functionally replaced by cascaded 2×2 couplers. This arrangement also results in independently varying phase related signals at the detectors. Other configurations also exist and will be known or apparent to those skilled in the art seeking to apply the invention.

Because the inventive system measures the phase relationship directly for each counter-propagating direction, different events actually are distinguishable as to the type of event concerned (in addition to its location), provided the events have characteristic distinct phase responses. The shape of the phase response during a disturbance has been found to depend in part on the way that the fiber was disturbed. A particular type of event may have a recognizable phase variation waveform over time due to the physical changes that affect the fiber, such as vibrating parts, lateral or longitudinal stress, bending, torque (twisting), etc. An event may also produce a greater or lesser stress. These phasor shapes may be useful in characterizing the nature of the disturbances.

Figure 39:
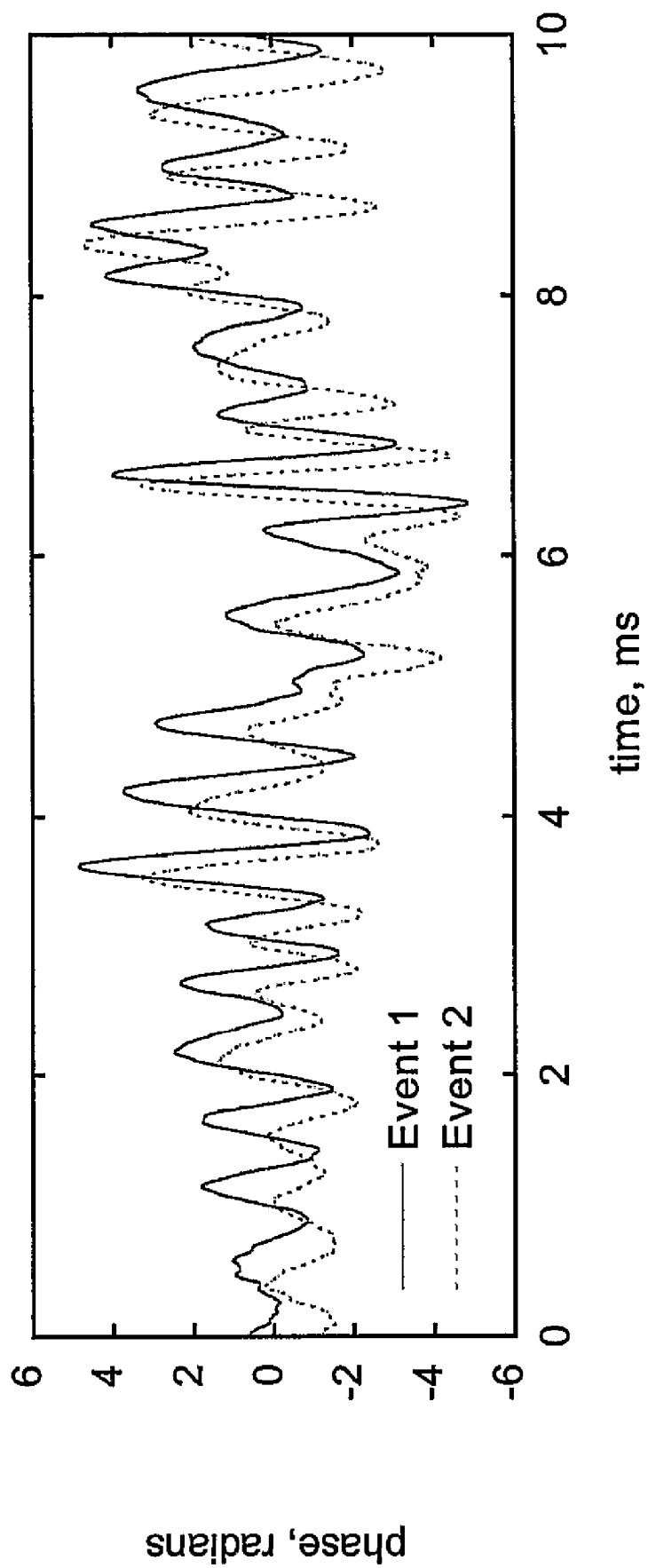
FIG. 39 is the time plot of the calculated phase produced to demonstrate similar signature, in which a disturbance (a recorded sound) was repeated.

FIG. 39 shows an event with an exemplary set of deflection and ringing aspects. Signature phase variations as shown in FIG. 39 can be matched to received waveforms and may help to characterize some types of events as known and non-threatening. An example is a recurring natural event (such wind pressure on a fence), to be distinguished from vibration of a person climbing the fence. Another example is a low level event (such as the movement of a small animal, etc.) for which it may be undesirable to trigger an alarm except during times of particularly high security.

Several advantageous embodiments have been discussed as examples, and other arrangement are also apt for certain needs. The proposed technology is useful for a distributed sensor associated with a fiber-carrying fence, or a perimeter defense system with in-ground fiber. A fiber can also be integrated into a wall or other structure. A fiber can be routed along a series of doors, windows and other portals. A fiber can be routed laterally across a path to detect a crossing event or longitudinally to assess progress along the path. Apart from security applications, the same sort of location sensing can be useful in industrial positioning, counting, level control and robotic motion applications. The invention also is applicable to traffic control systems. Numerous other possibilities should now be apparent from this disclosure.

According to another inventive aspect, a disturbance detecting and locating system as discussed can be used in a secure communication system, particularly in conjunction with optical fibers that are used for communication and detection at the same time. If an attempt is made to tap the optical fiber, or if other activities in proximity with the fiber even disturb the fiber, a phase disturbance occurs that can be detected in the same manner as detection of an event in an intrusion control system.

In such an embodiment, the optical communication channel may be carried over the same fibers as the sensing system or may simply be laid in proximity with the sensing fiber. For example, in a multi-fiber optical cable, a certain number of fibers can function as intrusion sensing fibers while using the rest of the fibers for data communications. As another example, the same fiber can be used both for the intrusion detection and carrying data, in a time division or wavelength division multiplexed manner. In that case multiple data channels can be carried over the same fiber while using one channel (or any number) for detection of intrusion, disturbance or the like.

The invention has been described in connection with a number of advantageous embodiments, but it should be appreciated that the invention is also applicable to other embodiments that are encompassed within the scope of the appended claims. Reference should be made to the claims rather than the foregoing description in order to assess the scope of exclusive rights claimed.

What is claimed is:

1. A detection apparatus comprising:
   at least one signal source, coupled to ends of a waveguide at least partly defining two signal paths for carrying signals in each of two counter-propagating directions, wherein at least one of said signal paths for each of the two counter-propagating directions traverses a detection zone;
   wherein a disturbance to be detected and located, occurring at a point in the detection zone that can be nearer to one or another of opposite ends of the detection zone can cause a time change in a phase relationship between the signals of said two signal paths, for each of said directions, originating at the point of disturbance and propagating over a distance toward opposite ends of said two signal paths, which distance can be longer or shorter depending on a distance between the point of the disturbance and respective said opposite ends;
   a phase responsive receiver coupled to each end of said signal paths, comprising at least one beam combiner for combining said two signals for a respective said end, and a detection device coupled to said beam combiner for each said end, wherein said detection device derives at least two mutually independent detector signals, wherein the detector signals developed by the detection device are further processed to obtain the phase relationship between said two signals for each of said two opposite directions;

a processor coupled to the said phase responsive receivers, operable to determine a time difference between receptions at said phase responsive receivers for said two opposite directions of said time change in said phase relationship, said time difference varying with a location of the point of the disturbance, which time difference identifies said point in the detection zone at which the disturbance occurred.

2. The apparatus of claim 1, wherein a respective said beam combiner for each of said opposite directions also serves as a beam splitter for an opposite one of said directions.

3. The apparatus of claim 1, wherein at least one of said two signals for each of the two counter-propagating directions traverses said detection zone along the same signal path, in opposite directions.

4. The apparatus of claim 1, further comprising at least one polarization state altering device coupled to at least one of the signal source, the waveguide and the phase responsive receiver, wherein the polarization state altering device affects a polarization aspect of at least one of the signals.

5. The apparatus of claim 4, wherein the polarization state altering device is disposed outside the waveguide so as to affect said two signal paths.

6. The apparatus of claim 4, wherein the polarization state altering device is disposed so as to affect at least one of said signal paths individually.

7. The apparatus of claim 4, wherein the polarization state altering device is operably placed at least one of: outside of the waveguide and inside the waveguide, so as to affect at least one of: the signal source, one of the signal paths, and both of the signal paths.

8. The apparatus of claim 4, wherein the polarization state altering device is coupled to the light source so as to affect said polarization aspect for both said counter-propagating signals.

9. The apparatus of claim 1, further comprising a beam splitter coupled to separate a signal from the at least one signal source into two signals, the beam splitter being coupled to apply counter propagating signals to said waveguide.

10. The apparatus of claim 1, wherein the signal source comprises a substantially coherent light source.

11. The apparatus of claim 1, wherein the light source comprises two distinct light sources for said counter-propagating directions.

12. The apparatus of claim 11, wherein said two light sources have substantially equal wavelengths.

13. The apparatus of claim 1, wherein the signal source comprises a light source with a changeable wavelength, and further comprising a control for tuning the wavelength of said light source.

14. The apparatus of claim 1, wherein the said waveguide comprises at least one optical fiber.

15. The apparatus of claim 14, wherein the optical fiber is single-mode fiber.

16. The apparatus of claim 1, wherein said waveguide is one of structured and installed to at least partly isolate the waveguide from at least one form of physical stress.

17. The apparatus of claim 16, wherein the waveguide comprises at least one optical fiber enclosed in a jacket, wherein the jacket has a hardness that limits said stress.

18. The apparatus of claim 1, wherein the waveguide is placed to dispose said detection zone in operative relation to at least one of an above ground structure, a building, a fence, a perimeter, an underground structure, an infrastructure element, a transmission line for one of signals and power, a pipeline, a road, a path, a bridge, a succession of spaced detection points, and an array encompassing one, two or three dimensions in space.

19. The apparatus of claim 1, wherein the at least one beam combiner in the phase responsive receiver comprises at least three output ports.

20. The apparatus of claim 19, wherein the beam combiner comprises a fused three-by-three fiber coupler.

21. The apparatus of claim 20, wherein the three-by-three fiber coupler is characterized by a substantially equal power distribution relationship between an input beam and the three output ports, when a single said input beam is presented.

22. The apparatus of claim 1, wherein the beam combiner comprises at least two cascaded fused fiber couplers.

23. The apparatus of claim 1, wherein at least one of the said the beam combiners in said phase responsive receiver is polarization sensitive.

24. The apparatus of claim 23, wherein the beam combiner is operative to combine orthogonal polarization components.

25. The apparatus of claim 1, wherein the detection device in said phase responsive receiver comprises at least two polarization sensitive detectors.

26. The apparatus of claim 25, wherein said polarization sensitive detectors detect signal responses that are at least partly related to different polarization components reflecting said phase relationship.

27. The apparatus of claim 26, wherein said at least two polarization sensitive detectors in the phase responsive receiver produce values from at least one output ports of the beam combiner, reflecting said phase relationship.

28. The apparatus of claim 26, wherein said polarization sensitive detectors are capable of completely characterizing a state of polarization.

29. The apparatus of claim 1, wherein said detection device in the phase responsive receiver produces values from two output ports of the beam combiner reflecting said phase relationship.

30. The apparatus of claim 1, wherein said phase responsive receiver further comprises a lead link coupled between said beam combiner and said detection device.

31. The apparatus of claim 30, wherein said lead link comprises at least one an optical fiber.

32. The apparatus of claim 1, wherein the processor comprises at least one processing unit operable for at least one of:
    deriving the mutually independent detector signals from the detectors,
    calculating the phase relationship between the combining beams by processing said detected and mutually independent detector signals,
    correlating a time signature of the disturbance in the phase relationship for the opposite directions,
    determining the time difference,
    determining the location of the point of the disturbance, and
    signaling and indication representing the point of the disturbance.

33. The apparatus of claim 32, wherein said processing unit comprises at least one of a computer, a digital signal processor and a field programmable gate array.

34. The apparatus of claim 32, where in the counter-propagating directions use different processing units.

35. The apparatus of claim 1, wherein the processor is programmed to affect a multi-dimensional data analysis technique by which the said mutually independent detector signals derived from the detectors are analyzed and combined to represent said phase relationship.

36. The apparatus of claim 35, wherein the processor is operable as a part of the data analysis technique to process the trajectories by at least one of remapping a trajectory to a circle, remapping a trajectory with respect to at least one of radius and eccentricity, applying the trajectory to an offset defining one of a center origin and a reference angle around an origin, and determining an angular difference between successive data samples.

37. The apparatus of claim 1, wherein the processor comprises at least one processing unit operable for deriving from the detectors a combination of values representing a linear combination of detector signals from the detectors, and for deriving from the linear combination a phase angle for each of the two opposite directions.

38. The apparatus of claim 37, wherein the linear combination comprises at least one of a sum and a difference of values.

39. The apparatus of claim 1, further comprising at least one additional detection apparatus having at least one waveguide and corresponding phase responsive detectors, and wherein said apparatus and the additional detection apparatus share at least one of a light source and a processor.

40. The apparatus of claim 1, wherein said waveguide comprises at least one signal path useful for one of communications and information transmission.

41. The apparatus of claim 40, above, wherein said signal path is integrated with a security system comprising at least one surveillance device.

42. The apparatus of claim 1, wherein said waveguide comprises at least one additional signal path useful for one of communications and information transmission.

43. A detection apparatus, comprising:
a laser;
a beam splitter coupled to the laser, providing at least two signals;
a fiber Mach-Zehnder interrerometer comprising at least two fibers through which said at least two signals are coupled in counter-propagating directions through a bidirectional splitter/combiner at each end of said fibers, the splitter/combiner comprising a coupler and having three inputs and three outputs;
at least two detectors on each of the ends of said fibers, each of the detectors coupled to generate detector signals for two outputs of a respective one of said couplers;
a processing unit operable to collect data from the detectors and to effect a data analysis technique comprising developing data samples containing at least two independent variables for each of said counter-propagating directions, deriving a phase relationship between the signals from said data samples for each of said counter-propagating directions, correlating the phase relationships for said counter-propagating directions and obtaining the time difference between said two phase relationships, wherein the processing unit derives a location corresponding to a point along the fibers at which a difference in times of propagation of the signals in opposite directions equals said time difference, and providing an output based thereupon.

44. A method for discriminating phase over time, comprising the steps of:
providing at least two signal paths having at least two signals propagating in at least one direction, a phase relationship of the beams at a receiving end of the signal path defining a phase variation to be discriminated;
combining said at least two beams and generating from the combined beams at least two detector signal outputs;
repetitively sampling from the detector signal outputs at least two signal levels that vary independently of one another according to the phase variation, thereby providing for each sample a pair of variable values defining a point in a numerical variable space;
processing the variable values to map a trajectory of the variable values to points on a circle;
determining an angular difference for points for two of the respective samples; and,
encoding said angular difference as a corresponding change in the phase relationship of the signals over time.

45. The method of claim 44, wherein the at least two detector signal outputs are deriving from at least portions of distinct polarization components of said combined beams.

46. The method of claim 45, wherein the at least two detector signal outputs are selecting orthogonal polarization components of the said combined beams.

47. The method of claim 44, wherein the at least two beams comprising light signals propagating in at least two optical fibers.

48. The method of claim 47, where the said at least two beams are combing using a fiber coupler.

49. The method of claim 48, wherein the said fiber coupler is polarization sensitive.

50. The method of claim 48, wherein the said fiber coupler is polarization insensitive.

51. The method of claim 48, wherein said fiber coupler comprises a coupler having at least three outputs, and wherein the paired variable values that correspond to the phase relationship are derived from detector signal levels at two of the three outputs of the coupler.

52. The method of claim 51, comprising operating said method for each of two counter-propagating signal directions by applying said light signals in counter-propagating direction and deriving the paired variable values from said coupler having at least three outputs for each opposite end of the counter-propagating signal directions.

53. The method of claim 52, comprising three-by-three couplers at each said opposite end and further comprising launching the light signals for the counter-propagating directions oppositely inwardly onto two of three lines of each coupler coupled to at a launching end to direct the lights signals onto at least two signal paths, at least one of which passes through a detection zone, and combining light signals from the at least two signal paths using two of three lines of each coupler on a receiving end.

54. The method of claim 52, wherein the coupler for each opposite end comprises a three-by-three fused fiber coupler.

55. The method of claim 52, wherein the coupler for at least one of the opposite ends comprises a cascade of at least two couplers.

56. The method of claim 44, comprising operating said method for each of two counter-propagating signal directions, thereby deriving said pairs of variable values for two counter-propagating signal paths with plural beams, for both of said counter-propagating directions, and thereby deriving two said phase relationships versus time.

57. The method of claim 56, further comprising correlating in the two phase relationships versus time a signature variation representing a phase effect of a physical disturbance affecting both beams in at least one of the signal paths, the signature variation being correlated at a lead/lag time in a case of the physical disturbance occurring over a longer or shorter propagation distance between the disturbance and opposite ends of the signal paths.

58. The method of claim 57, further comprising calculating a position of the disturbance from the lead/lag time.

59. The method of claim 44, wherein the paired variable values that correspond to the phase relationship at least partly reflect a projection in a two dimensional plane of a polarization state, wherein the projection is variable in at least one of eccentricity and size in remapping the values to said circle.

60. The method of claim 59, further comprising adjusting at least one of a polarization state of said beams as injected into said signal path, a polarization transfer function of the signal path, and a wavelength, for altering at least one of the eccentricity and the size.

* * * * *